(12) United States Patent
Li et al.

(10) Patent No.: US 12,016,694 B2
(45) Date of Patent: Jun. 25, 2024

(54) ELECTROCARDIOGRAM PROCESSING SYSTEM FOR DELINEATION AND CLASSIFICATION

(71) Applicant: KONINKLIJKE PHILIPS N.V., Eindhoven (NL)

(72) Inventors: Jia Li, Paris (FR); Romain Pomier, Paris (FR); Chiara Scabellone, Paris (FR); Cyril Gaudefroy, Paris (FR); Benjamin Barre, Suresnes (FR); Julien Fontanarava, Paris (FR); Christophe Gardella, Paris (FR); Mathieu Sornay, Paris (FR); Thomas Bordier, Paris (FR); Karen Prior, Jouy-les-Reims (FR); Marie-Albane De Saint Victor, Paris (FR)

(73) Assignee: CARDIOLOGS TECHNOLOGIES SAS, Paris (FR)

(*) Notice: Subject to any disclaimer, the term of this patent is extended or adjusted under 35 U.S.C. 154(b) by 0 days.

(21) Appl. No.: 17/390,714

(22) Filed: Jul. 30, 2021

(65) Prior Publication Data
US 2022/0031223 A1 Feb. 3, 2022

Related U.S. Application Data

(63) Continuation of application No. PCT/IB2020/050850, filed on Feb. 3, 2020, which is
(Continued)

(51) Int. Cl.
*A61B 5/366* (2021.01)
*A61B 5/00* (2006.01)
(Continued)

(52) U.S. Cl.
CPC ............ *A61B 5/366* (2021.01); *A61B 5/0006* (2013.01); *A61B 5/308* (2021.01); *A61B 5/339* (2021.01);
(Continued)

(58) Field of Classification Search
CPC ......... A61B 5/366; A61B 5/339; A61B 5/308; A61B 5/0006; A61B 5/7264; A61B 2560/02; G06N 3/02
(Continued)

(56) References Cited

U.S. PATENT DOCUMENTS 5,024,225 A 6/1991 Fang
5,239,494 A 8/1993 Golbeck
(Continued)

FOREIGN PATENT DOCUMENTS

CA 2466848 A1 6/2003
CN 101268938 A 9/2008
(Continued)

OTHER PUBLICATIONS

Alfonso, et al., ECG Beat Detection Using Filter Banks, IEEE Transactions on Biomedical Engineering, 46(2):192-202 (Feb. 1999).
(Continued)

*Primary Examiner* — Erin M Piateski

(57) ABSTRACT

Systems and methods are provided for analyzing electrocardiogram (ECG) data of a patient using a substantial amount of ECG data. The systems receive ECG data from a sensing device positioned on a patient such as one or more ECG leads. The system may include an application that communicates with an ECG platform running on a server(s) that processes and analyzes the ECG data, e.g., using neural networks for delineation of the cardiac signal and classification of various abnormalities, conditions and/or descriptors. The ECG platform may further process and analyze the
(Continued)

ECG data using neural networks and/or algorithms for embedding and grouping. The processed ECG data is used to generate a graphic user interface that is communicated from the server(s) to a computer for display in a user-friendly and interactive manner with enhanced accuracy.

21 Claims, 54 Drawing Sheets

Related U.S. Application Data a continuation-in-part of application No. 16/267,380, filed on Feb. 4, 2019, now Pat. No. 10,959,660.

(51) Int. Cl.
  *A61B 5/308* (2021.01)
  *A61B 5/339* (2021.01)
  *G06N 3/02* (2006.01)

(52) U.S. Cl.
  CPC ............. *A61B 5/7264* (2013.01); *G06N 3/02* (2013.01); *A61B 2560/02* (2013.01)

(58) Field of Classification Search
  USPC ........................................................ 600/517
  See application file for complete search history.

(56) References Cited

U.S. PATENT DOCUMENTS

| | | |
|---|---|---|
| 5,533,511 A | 7/1996 | Kaspari et al. |
| 5,619,991 A | 4/1997 | Sloane |
| 5,623,935 A | 4/1997 | Faisandier |
| 5,819,007 A | 10/1998 | Elghazzawi |
| 5,907,291 A | 5/1999 | Chen et al. |
| 5,966,692 A | 10/1999 | Langer et al. |
| 6,024,699 A | 2/2000 | Surwit et al. |
| 6,157,850 A | 12/2000 | Diab et al. |
| 6,507,753 B1 | 1/2003 | Xue et al. |
| 6,612,985 B2 | 9/2003 | Eiffert et al. |
| 6,656,125 B2 | 12/2003 | Misczynski et al. |
| 6,694,177 B2 | 2/2004 | Eggers et al. |
| 7,142,907 B2 | 11/2006 | Xue et al. |
| 7,289,844 B2 | 10/2007 | Misczynski et al. |
| 7,941,207 B2 | 5/2011 | Korzinov |
| RE43,767 E | 10/2012 | Eggers et al. |
| 8,332,017 B2 | 12/2012 | Tarassenko et al. |
| 8,668,644 B2 | 3/2014 | Ong et al. |
| 8,684,900 B2 | 4/2014 | Tran |
| 8,818,496 B2 | 8/2014 | Dziubinski et al. |
| D717,955 S | 11/2014 | Bishay et al. |
| 8,903,479 B2 | 12/2014 | Zoicas |
| 8,932,220 B2 | 1/2015 | Ong et al. |
| 8,951,193 B2 | 2/2015 | Ong et al. |
| D744,659 S | 12/2015 | Bishay et al. |
| 9,241,650 B2 | 1/2016 | Amirim |
| 9,254,095 B2 | 2/2016 | Galloway et al. |
| 9,295,429 B2 | 3/2016 | Ong et al. |
| 9,339,202 B2 | 5/2016 | Brockway et al. |
| 9,345,414 B1 | 5/2016 | Bardy et al. |
| 9,351,652 B2 | 5/2016 | Dziubinski et al. |
| 9,364,155 B2 | 6/2016 | Bardy et al. |
| 9,408,545 B2 | 8/2016 | Felix et al. |
| 9,408,551 B2 | 8/2016 | Bardy et al. |
| 9,420,957 B2 | 8/2016 | Ong et al. |
| D766,447 S | 9/2016 | Bishay et al. |
| 9,433,367 B2 | 9/2016 | Felix et al. |
| 9,433,380 B1 | 9/2016 | Bishay et al. |
| 9,468,386 B2 | 10/2016 | Braojos Lopez et al. |
| 9,504,423 B1 | 11/2016 | Bardy et al. |
| 9,545,204 B2 | 1/2017 | Bishay et al. |
| 9,545,228 B2 | 1/2017 | Bardy et al. |
| 9,554,715 B2 | 1/2017 | Bardy et al. |
| 9,615,763 B2 | 4/2017 | Felix et al. |
| 9,619,660 B1 | 4/2017 | Felix et al. |
| 9,642,537 B2 | 5/2017 | Felix et al. |
| 9,655,537 B2 | 5/2017 | Bardy et al. |
| 9,655,538 B2 | 5/2017 | Felix et al. |
| 9,700,227 B2 | 7/2017 | Bishay et al. |
| D793,566 S | 8/2017 | Bishay et al. |
| 9,717,432 B2 | 8/2017 | Felix et al. |
| 9,717,433 B2 | 8/2017 | Felix et al. |
| 9,730,593 B2 | 8/2017 | Felix et al. |
| 9,730,641 B2 | 8/2017 | Felix et al. |
| 9,737,211 B2 | 8/2017 | Bardy et al. |
| 9,737,224 B2 | 8/2017 | Bardy et al. |
| D801,528 S | 10/2017 | Bardy et al. |
| 9,775,536 B2 | 10/2017 | Felix et al. |
| 9,788,722 B2 | 10/2017 | Bardy et al. |
| 9,808,206 B1 | 11/2017 | Zhao et al. |
| 9,820,665 B2 | 11/2017 | Felix et al. |
| 9,901,274 B2 | 2/2018 | Bishay et al. |
| 9,936,875 B2 | 4/2018 | Bardy et al. |
| 9,955,885 B2 | 5/2018 | Felix et al. |
| 9,955,888 B2 | 5/2018 | Felix et al. |
| 9,955,911 B2 | 5/2018 | Bardy et al. |
| 10,004,415 B2 | 6/2018 | Bishay et al. |
| 10,045,709 B2 | 8/2018 | Bardy et al. |
| 10,052,022 B2 | 8/2018 | Bardy et al. |
| D831,833 S | 10/2018 | Bishay et al. |
| 10,111,601 B2 | 10/2018 | Bishay et al. |
| 10,123,703 B2 | 11/2018 | Bardy et al. |
| 10,154,793 B2 | 12/2018 | Felix et al. |
| D838,370 S | 1/2019 | Bardy et al. |
| 10,165,946 B2 | 1/2019 | Bardy et al. |
| 10,172,534 B2 | 1/2019 | Felix et al. |
| 10,251,575 B2 | 4/2019 | Bardy et al. |
| 10,251,576 B2 | 4/2019 | Bardy et al. |
| 10,264,992 B2 | 4/2019 | Felix et al. |
| 10,265,015 B2 | 4/2019 | Bardy et al. |
| 10,271,755 B2 | 4/2019 | Felix et al. |
| 10,271,756 B2 | 4/2019 | Felix et al. |
| 10,278,603 B2 | 5/2019 | Felix et al. |
| 10,278,606 B2 | 5/2019 | Bishay et al. |
| 10,426,364 B2 | 10/2019 | Rapin et al. |
| 10,492,730 B1 | 12/2019 | Mehta |
| 10,568,570 B1 | 2/2020 | Sherpa |
| 10,758,139 B2 | 9/2020 | Rapin et al. |
| 10,779,744 B2 | 9/2020 | Rapin et al. |
| 10,827,938 B2 | 11/2020 | Fontanarava et al. |
| 10,959,660 B2 | 3/2021 | Li et al. |
| 11,134,880 B2 | 10/2021 | Rapin et al. |
| 11,147,500 B2 | 10/2021 | Li et al. |
| 11,331,034 B2 | 5/2022 | Rapin et al. |
| 2001/0029338 A1 | 10/2001 | Krishnamachari |
| 2002/0169487 A1 | 11/2002 | Graindorge |
| 2003/0176795 A1 | 9/2003 | Harris et al. |
| 2004/0147840 A1 | 7/2004 | Duggirala et al. |
| 2004/0230105 A1 | 11/2004 | Geva et al. |
| 2004/0260192 A1 | 12/2004 | Yamamoto |
| 2005/0101873 A1 | 5/2005 | Misczynski et al. |
| 2005/0113706 A1 | 5/2005 | Prystowsky et al. |
| 2005/0171448 A1 | 8/2005 | Korzinov et al. |
| 2005/0182334 A1 | 8/2005 | Korzinov et al. |
| 2005/0222508 A1 | 10/2005 | Moreno et al. |
| 2005/0256413 A1 | 11/2005 | Astrom |
| 2006/0020219 A1 | 1/2006 | Zinser, Jr. et al. |
| 2006/0173369 A1 | 8/2006 | Kaski |
| 2007/0129642 A1 | 6/2007 | Korzinov |
| 2007/0191723 A1 | 8/2007 | Prystowsky et al. |
| 2007/0244402 A1 | 10/2007 | Brockway et al. |
| 2008/0004904 A1* | 1/2008 | Tran ..................... A61B 5/411 340/286.07 |
| 2008/0082016 A1 | 4/2008 | Kohls et al. |
| 2008/0103403 A1 | 5/2008 | Cohen |
| 2008/0132799 A1 | 6/2008 | Xue |
| 2008/0167567 A1 | 7/2008 | Bashour et al. |
| 2009/0112110 A1 | 4/2009 | Zhang |
| 2009/0192394 A1 | 7/2009 | Guttag et al. |
| 2010/0030302 A1 | 2/2010 | Blowers et al. |
| 2010/0056940 A1 | 3/2010 | Moorman et al. |
| 2010/0076331 A1 | 3/2010 | Chan et al. |

(56) References Cited

U.S. PATENT DOCUMENTS

| | | |
|---|---|---|
| 2010/0217144 A1* | 8/2010 | Brian .................... G16H 50/30 600/523 |
| 2010/0268103 A1 | 10/2010 | McNamara et al. |
| 2011/0184297 A1 | 7/2011 | Vitali et al. |
| 2011/0224565 A1 | 9/2011 | Ong et al. |
| 2011/0257548 A1 | 10/2011 | Dong et al. |
| 2011/0282225 A1 | 11/2011 | Anderson et al. |
| 2011/0301435 A1 | 12/2011 | Albert et al. |
| 2012/0110226 A1 | 5/2012 | Vlach et al. |
| 2012/0203491 A1 | 8/2012 | Sun et al. |
| 2012/0278099 A1 | 11/2012 | Kelly et al. |
| 2013/0116585 A1 | 5/2013 | Bouguerra |
| 2013/0184599 A1 | 7/2013 | Friedman et al. |
| 2013/0237776 A1 | 9/2013 | Ong et al. |
| 2014/0005988 A1 | 1/2014 | Brockway |
| 2014/0073486 A1 | 3/2014 | Ahmed et al. |
| 2014/0107493 A1 | 4/2014 | Yuen et al. |
| 2014/0128758 A1 | 5/2014 | Galloway et al. |
| 2014/0148714 A1 | 5/2014 | Mamaghanian et al. |
| 2014/0187988 A1 | 7/2014 | Ong et al. |
| 2014/0188770 A1 | 7/2014 | Agrafioti et al. |
| 2014/0228665 A1 | 8/2014 | Albert |
| 2014/0275840 A1 | 9/2014 | Osorio |
| 2014/0330147 A1 | 11/2014 | Ousdigian et al. |
| 2015/0008802 A1 | 1/2015 | Fukuda |
| 2015/0018702 A1 | 1/2015 | Galloway et al. |
| 2015/0051505 A1 | 2/2015 | Rossi |
| 2015/0088020 A1 | 3/2015 | Dreisbach et al. |
| 2015/0088024 A1 | 3/2015 | Sackellares et al. |
| 2015/0105640 A1 | 4/2015 | Friedman et al. |
| 2015/0119725 A1 | 4/2015 | Martin et al. |
| 2015/0164349 A1 | 6/2015 | Gopalakrishnan et al. |
| 2015/0190067 A1 | 7/2015 | Prystowsky et al. |
| 2015/0223759 A1* | 8/2015 | Ong ....................... G16Z 99/00 600/301 |
| 2015/0238151 A1 | 8/2015 | Sitzman et al. |
| 2015/0248534 A1 | 9/2015 | Krzywicki et al. |
| 2015/0257668 A1 | 9/2015 | Braojos Lopez et al. |
| 2015/0282726 A1 | 10/2015 | Grube et al. |
| 2015/0289112 A1 | 10/2015 | Gilbert et al. |
| 2016/0051157 A1 | 2/2016 | Waydo |
| 2016/0058318 A1 | 3/2016 | Borjigin et al. |
| 2016/0085927 A1 | 3/2016 | Dettinger et al. |
| 2016/0085937 A1 | 3/2016 | Dettinger et al. |
| 2016/0086297 A1 | 3/2016 | Dettinger et al. |
| 2016/0098536 A1 | 4/2016 | Dettinger et al. |
| 2016/0098537 A1 | 4/2016 | Dettinger et al. |
| 2016/0098538 A1 | 4/2016 | Dettinger et al. |
| 2016/0135706 A1 | 5/2016 | Sullivan et al. |
| 2016/0150989 A1 | 6/2016 | Felix et al. |
| 2016/0183827 A1 | 6/2016 | Xue et al. |
| 2016/0183829 A1 | 6/2016 | Friedman et al. |
| 2016/0192850 A1 | 7/2016 | Gregg et al. |
| 2016/0192853 A1 | 7/2016 | Bardy et al. |
| 2016/0235319 A1 | 8/2016 | Albert |
| 2016/0242665 A1 | 8/2016 | Galloway et al. |
| 2016/0249823 A1 | 9/2016 | Galloway et al. |
| 2016/0262646 A1 | 9/2016 | Bardy et al. |
| 2016/0321430 A1 | 11/2016 | Eckman et al. |
| 2016/0345854 A1 | 12/2016 | Bardy et al. |
| 2016/0345909 A1 | 12/2016 | Felix et al. |
| 2016/0367187 A1 | 12/2016 | Ahmed et al. |
| 2017/0014037 A1 | 1/2017 | Coppola et al. |
| 2017/0095153 A1 | 4/2017 | Bardy et al. |
| 2017/0098047 A1 | 4/2017 | Young |
| 2017/0105683 A1 | 4/2017 | Xue |
| 2017/0112401 A1* | 4/2017 | Rapin .................. A61B 5/7267 |
| 2017/0135579 A1 | 5/2017 | Bardy et al. |
| 2017/0177811 A1 | 6/2017 | Mcfarland et al. |
| 2017/0188872 A1 | 7/2017 | Hughes et al. |
| 2017/0238833 A1 | 8/2017 | Felix et al. |
| 2017/0251948 A1 | 9/2017 | Felix et al. |
| 2017/0258358 A1 | 9/2017 | Bishay et al. |
| 2017/0340206 A1 | 11/2017 | Bardy et al. |
| 2017/0340290 A1 | 11/2017 | Felix et al. |
| 2017/0357764 A1 | 12/2017 | Fauss et al. |
| 2017/0367609 A1 | 12/2017 | Bardy et al. |
| 2018/0020939 A1 | 1/2018 | Albert |
| 2018/0028144 A1 | 2/2018 | Chen et al. |
| 2018/0060522 A1 | 3/2018 | Petterson et al. |
| 2018/0146875 A1 | 5/2018 | Friedman et al. |
| 2018/0177423 A1 | 6/2018 | Bishay et al. |
| 2018/0206752 A1 | 7/2018 | Bardy et al. |
| 2018/0242876 A1 | 8/2018 | Hughes et al. |
| 2018/0279956 A1 | 10/2018 | Waydo et al. |
| 2018/0289274 A1 | 10/2018 | Bahney et al. |
| 2018/0296118 A1 | 10/2018 | Bishay et al. |
| 2018/0310892 A1 | 11/2018 | Perschbacher et al. |
| 2018/0344189 A1 | 12/2018 | Dusan |
| 2018/0344191 A1 | 12/2018 | Bardy et al. |
| 2018/0353071 A1 | 12/2018 | Bardy et al. |
| 2018/0368715 A1 | 12/2018 | Xue et al. |
| 2018/0374576 A1 | 12/2018 | Dettinger et al. |
| 2019/0034050 A1 | 1/2019 | Williams et al. |
| 2019/0038149 A1 | 2/2019 | Gopalakrishnan et al. |
| 2019/0059763 A1 | 2/2019 | Shakur et al. |
| 2019/0069794 A1 | 3/2019 | Bardy et al. |
| 2019/0069798 A1 | 3/2019 | Bardy |
| 2019/0069800 A1 | 3/2019 | Bardy et al. |
| 2019/0076023 A1 | 3/2019 | Bardy et al. |
| 2019/0090769 A1 | 3/2019 | Boleyn et al. |
| 2019/0099105 A1 | 4/2019 | Felix et al. |
| 2019/0104951 A1 | 4/2019 | Valys et al. |
| 2019/0104961 A1 | 4/2019 | Felix et al. |
| 2019/0117068 A1 | 4/2019 | Thomson et al. |
| 2019/0117099 A1 | 4/2019 | Bardy et al. |
| 2019/0117107 A1 | 4/2019 | Felix et al. |
| 2019/0133444 A1 | 5/2019 | Bardy et al. |
| 2019/0133483 A1 | 5/2019 | Xue et al. |
| 2019/0133486 A1 | 5/2019 | Felix et al. |
| 2019/0167141 A1 | 6/2019 | Duckert et al. |
| 2019/0167143 A1 | 6/2019 | Li et al. |
| 2019/0223739 A1 | 7/2019 | Rapin et al. |
| 2019/0259496 A1 | 8/2019 | Pemberton et al. |
| 2019/0267139 A1 | 8/2019 | Hutchins et al. |
| 2019/0272920 A1 | 9/2019 | Teplitzky |
| 2019/0274563 A1 | 9/2019 | Soli et al. |
| 2019/0274574 A1 | 9/2019 | Hughes et al. |
| 2019/0282118 A1 | 9/2019 | Kaski |
| 2019/0298204 A1 | 10/2019 | Fontanarava et al. |
| 2019/0357794 A1 | 11/2019 | Bardy et al. |
| 2020/0013507 A1 | 1/2020 | Braun et al. |
| 2020/0015694 A1 | 1/2020 | Rapin et al. |
| 2020/0022591 A1 | 1/2020 | Drakulic et al. |
| 2020/0022604 A1 | 1/2020 | Scabellone et al. |
| 2020/0029911 A1* | 1/2020 | Chakravarthy ...... A61B 5/6802 |
| 2020/0060563 A1 | 2/2020 | Boleyn et al. |
| 2020/0118673 A1 | 4/2020 | Dettinger et al. |
| 2020/0155025 A1 | 5/2020 | Smith et al. |
| 2020/0178825 A1 | 6/2020 | Lu et al. |
| 2020/0205745 A1 | 7/2020 | Khosousi et al. |
| 2020/0237317 A1 | 7/2020 | Newberry et al. |
| 2020/0242763 A1 | 7/2020 | Bhuiyan et al. |
| 2020/0273567 A1 | 8/2020 | Petterson et al. |
| 2020/0289014 A1 | 9/2020 | Park et al. |
| 2020/0289033 A1 | 9/2020 | Sivertsen et al. |
| 2020/0289063 A1 | 9/2020 | Mehta |
| 2020/0297286 A1 | 9/2020 | Costa et al. |
| 2020/0397313 A1 | 12/2020 | Attia et al. |
| 2020/0401684 A1 | 12/2020 | Vath et al. |
| 2021/0000344 A1 | 1/2021 | Dreisbach et al. |
| 2021/0000365 A1 | 1/2021 | Rapin et al. |
| 2021/0076960 A1 | 3/2021 | Fornwalt et al. |
| 2021/0150693 A1 | 5/2021 | Fornwalt et al. |
| 2021/0204859 A1 | 7/2021 | Moll |
| 2021/0271847 A1 | 9/2021 | Courtiol et al. |

FOREIGN PATENT DOCUMENTS

| | | |
|---|---|---|
| CN | 101766484 A | 7/2010 |
| CN | 102188240 A | 9/2011 |
| CN | 102379694 A | 3/2012 |
| CN | 102779234 A | 11/2012 |
| CN | 103038772 A | 4/2013 |

(56) References Cited

FOREIGN PATENT DOCUMENTS

| | | | |
|---|---|---|---|
| CN | 103110417 A | 5/2013 | |
| CN | 103284702 A | 9/2013 | |
| CN | 103417209 A | 12/2013 | |
| CN | 104463326 A | 3/2015 | |
| CN | 104970789 A | 10/2015 | |
| CN | 106778685 A | 5/2017 | |
| DE | 60127354 T2 | 12/2007 | |
| EP | 0465241 A2 | 1/1992 | |
| EP | 0465241 B1 | 11/1998 | |
| EP | 1179319 A1 | 2/2002 | |
| EP | 1503664 A2 | 2/2005 | |
| EP | 2030565 A1 | 3/2009 | |
| EP | 2534597 A2 | 12/2012 | |
| EP | 3144851 A1 | 3/2017 | |
| EP | 2534597 B1 | 10/2018 | |
| JP | 2002172096 A | 6/2002 | |
| JP | 2013524865 A | 6/2013 | |
| KR | 20150020955 A | 2/2015 | |
| WO | WO-9738626 A1 | 10/1997 | |
| WO | WO-03045224 A2 | 6/2003 | |
| WO | WO-03045224 A3 | 11/2004 | |
| WO | WO-2006048881 A2 | 5/2006 | |
| WO | WO-2011115576 A2 | 9/2011 | |
| WO | WO-2012140559 A1 | 10/2012 | |
| WO | WO-2016110804 A1 | 7/2016 | |
| WO | WO-2016145392 A1 | 9/2016 | |
| WO | WO-2017072250 A1 | 5/2017 | |
| WO | WO-2019038435 A1 | 2/2019 | |
| WO | WO-2019089830 A1 | 5/2019 | |
| WO | WO-2019147180 A1 | 8/2019 | |
| WO | WO-2020086865 A1 | 4/2020 | |
| WO | WO-2020161605 A1 | 8/2020 | |

OTHER PUBLICATIONS

Almeida, et al., Multilead ECG Delineation Using Spatially Projected Leads From Wavelet Transform Loops, IEEE Transactions On Biomedical Engineering, 56(8):1996-2005 (Aug. 2009).

Badilini, et al., ECGScan: A Method for Conversion of Paper Electrocardiogramtouts to Digital Electrocardiogramas, Journal of Electrocardiology, 38:310-318 (Oct. 2005).

Bishop, Pattern Recognition and Machine Learning, Springer, Information Science and Statistics, 2006, ISBN-10: 0-387-31073-8, New York, NY, USA.

Boichat, et al., Wavelet-Based ECG Delineation on a Wearable Embedded Sensor Platform, Proceedings of Wearable and Implantable Body Sensor Networks, *2009 Sixth International Workshop on Wearable and Implantable Body Sensor Networks*, IEEE (pp. 256-261) (Jun. 2009).

Chazal, et al., A Patient-Adapting Heartbeat Classifier Using ECG Morphology and Heartbeat Interval Features, IEEE Transactions on Biomedical Engineering, 53(12):2535-2543 (Dec. 2006).

Chazal, et al., Automatic Classification of Heartbeats Using ECG Morphology and Heartbeat Interval Features, IEEE Transactions on Biomedical Engineering, 51(7):1196-1206 (Jul. 2004).

Chebil, et al., A Novel Method for Digitizing Standard ECG Papers, Proceedings of the International Conference on Computer and Communication Engineering 2008, May 13-15, 2008, Kuala Lumpur, Malaysia (pp. 1308-1312).

Choi, et al., Development of ECG Beat Segmentation Method by Combining Lowpass Filter and Irregular R-R Interval Checkup Strategy, Expert Systems with Applications, 37:5208-5218 (Jul. 2010).

Coast, et al., An Approach to Cardiac Arrhythmia Analysis Using Hidden Markov Models, IEEE transactions on biomedical engineering, 37(9):826-836 (Sep. 1990).

Cybenko, Approximation by Superpositions of a Sigmoidal Function, *Mathematics of Control, Signals and Systems*, 2(4):303-314 (Dec. 1989).

Donahue et al., Long-term Recurrent Convolutional Networks for Visual Recognition and Description, arXiv:1411.4389v3, (pp. 1-13) (Feb. 2015).

Dubois, et al., Automatic ECG Wave Extraction in Long-Term Recordings using Gaussian Mesa Function Models and Nonlinear Probability Estimators, *Computer Methods and Programs in Biomedicine*, 88:217-233 (Mar. 2007).

European Search Report dated Apr. 13, 2016 in EP Patent Appl. Serial No. 15191769.7 (0230).

Extended EP Search Report dated Apr. 12, 2021 in EP Patent Application Serial No. 20211449.2 (0431).

Extended European Search Report dated Jul. 20, 2021 in EP Patent Appl. Serial No. 21167613.5 (0331).

Extended European Search Report dated Oct. 15, 2018 in EP Patent Appl. Serial No. 18305376.8 (0530).

Fiorina, AI-Based Strategy Enables Faster Holter ECG Analysis With Equivalent Clinical Accuracy Compared to a Classical Strategy, EP Europace, vol. 22, Issue Supplement 1, Abstract 222 (Jun. 2020).

Fiorina, et al., Artificial Intelligence Based Platform Enables Faster Ambulatory Electrocardiogram Analysis With Equivalent Clinical Accuracy Compared to Traditional Solution, Circulation, vol. 140, Issue Suppl. 1, Abstract 9825 (Nov. 2019).

Fukushima., Neocognitron: A Self-organizing Neural Network Model for a Mechanism of Pattern Recognition Unaffected by Shift in Position, *Biological Cybernetics*, 36:193-202 (1980).

Hughes, et al., Markov Models for Automated ECG Interval Analysis, Proceedings of Neural Information Processing Systems, 2004, Oxford, UK, (pp. 611-618).

Ieva, et al., Multivariate Functional Clustering for the Morphological Analysis of Electrocardiogramal of the Royal Statistical Society: Series C (Applied Statistics), 62(3):401-418 (May 2013).

International Search Report & Written Opinion dated Aug. 1, 2019 in Int'l PCT Patent Appl. No. PCT/IB2019/052517 (0510).

International Search Report & Written Opinion dated Nov. 21, 2018 in Int'l PCT Patent Appl. Serial No. PCT/EP2018/072912 (0410).

International Search Report & Written Opinion dated Jun. 4, 2020 in PCT Patent Appl. Serial No. PCT/IB2020/050850 (0710 PCT).

International Search Report & Written Opinion dated Jan. 24, 2017 in Int'l PCT Patent Appl. Serial No. PCT/EP2016/075972 (0310).

Jin, et al., Deep Learning Research on Clinical Electrocardiogram Analysis, Science China Press, 45(3):398-416 (2015), English abstract provided.

Johnson, et al., R-Peak Estimation using Multimodal Lead Switching, *Computing in Cardiology 2014*, IEEE, pp. 281-284 (Sep. 2014).

Kaur et al., Comparison of Different Approaches for Removal of Baseline Wander From ECG Signal, *Proceedings of the International Conference & Workshop on Emerging Trends in Technology*, (pp. 30-36) (Feb. 2011).

Kiranyaz, et al., Convolutional Neural Networks for Patient-Specific ECG Classification, *2015 37th Annual International Conference of the IEEE Engineering in Medicine and Biology Society (EMBC)*, IEEE (pp. 2608-2611) (Aug. 2015).

Kiranyaz, et al., Real-Time Patient-Specific ECG Classification by 1-D Convolutional Neural Networks, *IEEE transactions on Biomedical Engineering*, 63(3):664-675 (Aug. 2015).

Krizhevsky, et al., ImageNet Classification with Deep Convolutional Neural Networks, Advances in neural information processing systems, 25:1097-1105 (2012).

Laguna, et al., A Database for Evaluation of Algorithms for Measurement of QT and Other Waveform Intervals in the ECG, *Computers in Cardiology 1997*, 24:673-676.

Lecun, et al., Backpropagation Applied to Handwritten Zip Code Recognition, *Neural Computation*, 1(4):541-551 (Dec. 1989).

Li, et al., Deep neural networks Improve Atrial Fibrillation Detection in Holter: first results, European Journal of Preventive Cardiology, Abstract, 23 (2S) (Oct. 2016).

Li, et al., Detection of ECG Characteristic Points Using Wavelet Transforms, *IEEE Transactions on Biomedical Engineering*, 42(1):21-28 (Jan. 1995).

Lin et al., Beat-to-beat p. and T Wave Delineation in ECG Signals using a Marginalized Particle Filter, *2012 Proceedings of the 20th European Signal Processing Conference (EUSIPCO)*, (pp. 479-483) (Aug. 2012).

Lin, et al., P. and Twave Delineation And Waveform Estimation in ECG Signals Using a Block Gibbs Sampler, *2011 IEEE Interna-*

(56) References Cited

OTHER PUBLICATIONS tional Conference on Acoustics, Speech and Signal Processing (ICASSP), (pp. 479-483) (May 2011).

Lin et al., P- and T-Wave Delineation in ECG Signals Using a Bayesian Approach and a Partially Collapsed Gibbs Sampler, IEEE Transactions on Biomedical Engineering, 57(12):2840-2849 (Sep. 2010).

Long, et al., Fully Convolutional Networks for Semantic Segmentation, Proceedings of The IEEE Conference On Computer Vision and Pattern Recognition, (pp. 3431-3440) (2015).

Maille, et al., Smartwatch Electrocardiogram and Artificial Intelligence for Assessing Cardiac-Rhythm Safety of Drug Therapy in the COVID-19 Pandemic. The QT-logs study, International Journal of Cardiology, 331:333-339 (May 2021).

Martinez et al., A Wavelet-Based ECG Delineator: Evaluation on Standard Databases, IEEE Transactions on Biomedical Engineering, 51(4): 570-581 (Mar. 2004).

Matan, et al., Multi-Digit Recognition Using a Space Displacement Neural Network, Neural Information Processing Systems, 2:488-495) (Jan. 1991).

Meghriche, et al., On the Analysis of a Compound Neural Network for Detecting Atrio Ventricular Heart Block (AVB) in an ECG Signal, International Journal of Biological and Medical Sciences, 1(1):1-11 (Mar. 2008).

Megriche, et al., On the Analysis of a Compound Neural Network for Detecting Atrio Ventricular Heart Block (AVB) in a ECG Signal, International Journal of Medical, Health, Biomedical, Bioengineering and Pharmaceutical Engineering, 2(3):68-78 (2008).

Mittal, et al., AI Filter Improves Positive Predictive Value of Atrial Fibrillation Detection by an Implantable Loop Recorder, JACC: Clinical Electrophysiology, available online Feb. 10, 2021, https://doi.org/10.1016/j.jacep.2020.12.006.

Mittal, et al., An Artificial Intelligence-based Solution To Reduce False Positive Detections of Atrial Fibrillation By An Implantable Loop Recorder, available at https://cslide-us.ctimeetingtech.com/hrs20/attendee/eposter/file/195#1 (retrieved Jul. 23, 2021).

Mnih, et al., Recurrent Models of Visual Attention, arXiv:1406.6247v1:1406.6247(Jun. 2014).

"Neural Nets and Noise Filtering", Dr. Dobb's Journal, pp. 32 (Jan. 1989).

Noda, et al., Audio-Visual Speech Recognition using Deep Learning, Applied Intelligence, 42(4):722-737, (Jun. 2015).

Nowlan, et al., A Convolutional Neural Network Hand Tracker, Advances in Neural Information Processing Systems7, (pp. 901-908) (Jan. 1995).

Pan, et al., A Real-Time QRS Detection Algorithm, IEEE Transactions on Biomedical Engineering, 3:230-236 (Mar. 1985).

Pigoli, et al., Wavelets in Functional Data Analysis: Estimation of Multidimensional Curves and their Derivatives, Computational Statistics & Data Analysis, 56(6):1482-1498 (Jun. 2012).

Portet, F., P Wave Detector with PP Rhythm Tracking: Evaluation in Different Arrhythmia Contexts, Physiological Measurement, 29(1):141-155 (Jan. 2008).

Prineas et al., The Minnesota Code Manual of Electrocardiographic Findings, Springer, Second Edition, ISBN 978-1-84882-777-6, 2009, Minneapolis, Minnesota, US.

Ravichandran, et al., Novel Tool for Complete Digitization of Paper Electrocardiogra Data, IEEE Journal of Translational Engineering in Health and Medicine, Medical Imaging and Diagnostic Radiology, 1:1800107 (Jun. 2013).

Rodrigues, et al., A Neural Network Approach to ECG Denoising, arXIV preprint arXiv:1212-5217 (Dec. 2012).

Rosenblatt, The Perceptron: A Probabilistic Model for Information Storage and Organization in the Brain, Psychological Review, 65(6):386-408 (Nov. 1958).

Russakovsky, et al., "ImageNet Large Scale Visual Recognition Challenge", International Journal of Computer Vision, 115(3):211-252 (Dec. 2015).

Saini, et al., Automated ECG Delineation using Machine Learning Algorithms, International Congress on Electrocardiology, Jalandhar, India, 2014, (pp. 1-4).

Schluter, et al., Improved Musical Onset Detection With Convolutional Neural Networks, IEEE International Conference on Acoustics, Speech, and Signal Processing (ICASSP ), (pp. 6979-6983) (May 2014).

Shen, et al., Multi-Lead ECG Classification Based on Independent Component Analysis and Support Vector Machine, 3rd International Conference on Biomedical Engineering and Informatics (BMEI), 3:960-964 (Oct. 2010).

Simonyan, et al., Very Deep Convolutional Networks for Large-Scale Image Recognition, arXiv preprint arXiv:1409.1556(Sep. 2014).

Smith, et al., Improved Interpretation of Atrial Dysrhythmias by a New Neural Network Electrocardiogram Interpretation Algorithm, Academic Emergency Medicine, vol. 24, S1, Abstract 670 (May 2017).

Smith, et al., Improved Interpretation of Atrial Dysrhythmias by a New Neural Network Electrocardiogram Interpretation Algorithm, Society for Academic Emergency Medicine Abstracts, 24 (S1), S235 (2017).

Statement of Validation and Accuracy for the Glasgow 12-Lead ECG Analysis Program, Physio Control, Mar. 2009, Redmond, WA USA.

Tun, et al., Analysis on conversion process from paper record ECG to computer based ECG, MOJ Applied Bionics and Biomechanics, 1(2):69-81 (2017).

Vaessen., An approach to ECG Delineation using Wavelet Analysis and Hidden Markov Models, Universiteit Maastricht Institute of Instrument Development Engineering & Evaluation Master Thesis, (Sep. 2006).

Zeiler, Matthew D., ADADELTA: An Adaptive Learning Rate Method, arXiv preprint arXiv:1212.5701(Dec. 2012).

Zhang et al., Improving Object Detection with Deep Convolutional Networks via Bayesian Optimization and Structured Prediction, Proceedings of the IEEE Conference on Computer Vision and Pattern Recognition, (pp. 249-258) (2015).

Zheng, et al., Time Series Classification Using Multi-Channels Deep Convolutional Neural Networks, International Conference on Web-Age Information Management, (pp. 298-310), (Jun. 2014).

Attia, et al., An artificial intelligence-enabled ECG algorithm for the identification of patients with atrial fibrillation during sinus rhythm: a retrospective analysis of outcome prediction, The Lancet, 394(10201):861-867 (Sep. 2019).

Christopoulos, et al., Artificial Intelligence-Electrocardiogramadict Incident Atrial Fibrillation—A Population-Based Study, Circulation: Arrhythmia and Electrophysiology, 13(12):e009355 (Dec. 2020).

Raghunath, et al., Deep Neural Networks Can Predict New-Onset Atrial Fibrillation From the 12-Lead ECG and Help Identify Those At Risk of Atrial Fibrillation-Related Stroke, Circulation, 143(13):1287-98 (Mar. 2021).

Smith, et al., A deep neural network for 12-lead electrocardiogram interpretation outperforms a conventional algorithm, and its physician overread, in the diagnosis of atrial fibrillation, IJC Heart & Vasculature, 25:100423 (Dec. 2019).

Smith, et al., A deep neural network learning algorithm outperforms a conventional algorithm for emergency department electrocardiogram interpretation, Journal of Electrocardiology, 52:88-95 (Jan. 2019).

International Search Report & Written Opinion dated Jan. 14, 2022 in Int'l PCT Patent Appl. Serial No. PCT/IB2021/0058958 (0910).

International Search Report & Written Opinion dated Jan. 31, 2022 in Int'l PCT Patent Appl. Serial No. PCT/IB2021/057341 (0810).

Artis, et al., Detection of Atrial Fibrillation Using Artificial Neural Networks, Proceedings Computers in Cardiology, pp. 173-176 (1991).

\* cited by examiner

Cardiologs

181 136, Rue Saint-Denis, 75002 Paris, France       182       zo4VyvOx

Patient Info       Clinician Info

| Name | Primary Indication | Analysis by | Name of Institute |
|---|---|---|---|
|  |  | Dr House | Cardiologs |
| Pacemaker | Date of Birth | Gender | Patient ID | Date of Analysis | Signature |
| No |  | Female | 123456789 | 03/21/2018 |  |

183

Signal Overview

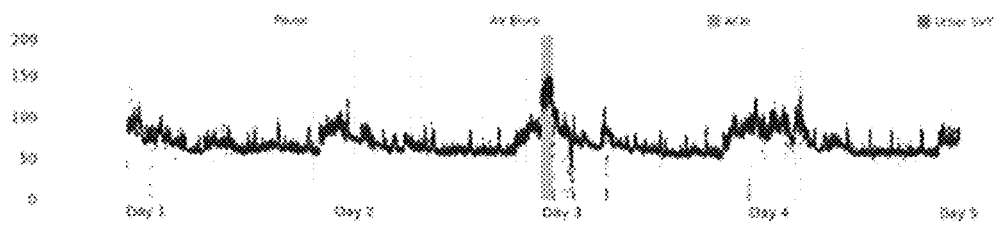

184

Metrics       Episodes       185

Duration of Recording       Pause
Start           03/01/2018, 10:00     3 Days    Count                                  ---
End             03/05/2018, 09:58               Longest RR                             ---
Heart Rate                                      Atrioventricular block
Max             184 bpm    Day 3 / 10:03:34     Type                                   ---
Min             49 bpm     Day 4 / 06:13:55     Longest RR interval                    ---
Avg             66 bpm                          Atrial Fibrillation / Flutter
Premature Supraventricular Complexes            Burden                              1.4%
PSVC count                          3983        Longest episode                   1h 21m
Per 24h                             1327        Max HR                           183 bpm
Premature Ventricular Complexes                 Ventricular Tachycardia
PVC count                           227         Count                                  ---
Per 24h                             75          Longest episode                        ---
No. of morphologies                 2           Other Supraventricular Tachycardia
Patient-triggered Events                        Count                                  20
Count                               ---         Longest episode                    20.0 s

Results

186

Sinus rhythm with paroxysmal atrial fibrillation (1.4 % of the duration, from 9am to 11am) with average HR of 66 bpm.

3983 PACs with 20 short runs of SVT (max duration of 20 s).
227 monomorphic PVCs with no short runs of VT.

No pauses nor AV block.

Page 1 of 4

FIG. 15A

Patient: Jane Doe
Extended Holter Report

Cardiologs
AI serving cardiology

─── 260
─── 261

Patient Summary

| | |
|---|---|
| Date of Birth | Gender |
| 08/19/1993 (26 yrs.) | Female |
| Patient ID | Pacemaker |
| XXXX | No |
| Primary Indication | Medication |
| Palpitations | -- |

Clinician Summary

| | |
|---|---|
| Analysis by | Institution |
| Julien Fontanarava | Cardiologs |
| Referred By | Interpreted by |
| -- | -- |

Report Summary

| | |
|---|---|
| Recording Length | Analysis Length |
| 6d 18h 45min | 6d 18h 40min |
| 07/28/2015 to | |
| 08/04/2015 | |
| Date of Analysis | Noise Burden |
| 09/26/2019 | 0.05% |

Heart Rate

| Max | Min | Average |
|---|---|---|
| 174bpm | 57bpm | 81bpm |
| 07/30/2015 | 08/01/2015 | |
| 03:27:08 pm | 06:56:14 am | |

Ectopics

Premature Supraventricular Complexes

| PSVC Count | Couplets |
|---|---|
| 919 (0.12%) | 6 (< 0.01%) |

Premature Ventricular Complexes

| PVC Count | No. of morphologies | |
|---|---|---|
| 1,370 (0.17%) | 2 | |
| Couplets | Bigeminy | Trigeminy |
| 94 (0.02%) | 5 (< 0.01%) | -- |

Patient Events

Count
1

Paced Beats

Count
--

AFib / Flutter

| Burden | Longest Episode | Max HR |
|---|---|---|
| 17.23% | 15h 59min on 07/30/2015 02:25:30 pm | 174bpm |

Representative Strip  HR: 174bpm  Duration: 15h 59min

Other SVT

| Count | Longest Episode | Max HR |
|---|---|---|
| -- | -- on -- | -- |

Representative Strip: None

Pause

| Count | Longest RR |
|---|---|
| -- | -- |

Representative Strip: None

AV Block

| Type | Longest RR |
|---|---|
| -- | -- |

Representative Strip: None

VT

| Count | Longest Episode | Max HR |
|---|---|---|
| 11 | 4 beats on 07/28/2015 07:55:29 pm | 201bpm |

Representative Strip  HR: 201bpm  Duration: 3 beats

Findings

Recording of 6d 18h, sinus rhythm with paroxysmal atrial fibrillation.
Max HR 174 bpm, min HR 57 bpm, average 81 bpm.

1370 PVCs, 94 ventricular couplets, 11 ventricular shortruns (longest of 4 beats).
919 PACs, 6 supraventricular couplets, AFib on 17.3% of the recording.

Signature                                    Cardiologs

FIG. 22A

© 2019 Cardiologs Technologies

Patient: Jane Doe    ←260      Patient ID: XXXX      Date of Birth: 08/19/1993 (26 yrs.)

Strip Index
←271

| ID | Date & Time | Category | HR | Patient Event | Comments | Page |
|----|-------------|----------|-----|---------------|----------|------|
| 1 | 07/29/2015 02:51:35 pm | Max HR | 132bpm | -- | Maximum heart rate in sinus | page 9 |
| 2 | 07/30/2015 03:27:08 pm | Max HR | 174bpm | -- | Maximum heart rate in AFib | page 9 |
| 3 | 08/01/2015 06:56:14 am | Min HR | 57bpm | -- | | page 9 |
| 4 | 07/28/2015 11:25:30 am | Sinus | 86bpm | -- | | page 9 |
| 5 | 07/29/2015 12:13:55 am | Sinus | 68bpm | -- | | page 10 |
| 6 | 07/29/2015 01:08:00 pm | Sinus | 79bpm | -- | | page 10 |
| 7 | 07/30/2015 02:25:42 pm | AFib / Flutter | 174bpm | Yes | Transition to AFib | page 10 |
| 8 | 07/30/2015 03:27:03 pm | AFib / Flutter | 174bpm | Yes | Fastest AFib | page 10 |
| 9 | 07/31/2015 06:24:39 am | AFib / Flutter | 174bpm | Yes | | page 10 |
| 10 | 07/28/2015 11:06:01 am | VT | 195bpm | -- | | page 11 |
| 11 | 07/28/2015 07:55:25 pm | VT | 184bpm | -- | | page 11 |
| 12 | 07/30/2015 02:52:25 pm | VT | 186bpm | -- | | page 11 |
| 13 | 07/30/2015 05:36:01 pm | VT | 187bpm | -- | | page 12 |
| 14 | 07/31/2015 04:51:08 am | VT | 201bpm | -- | Fastest ventricular triplet | page 12 |
| 15 | 07/30/2015 03:29:07 pm | Patient Event | -- | -- | | page 12 |
| 16 | 07/28/2015 01:33:16 pm | PVC | -- | -- | | page 12 |
| 17 | 07/28/2015 06:15:08 pm | PVC | -- | -- | | page 13 |
| 18 | 07/30/2015 03:55:59 pm | PVC | -- | -- | | page 13 |
| 19 | 07/30/2015 04:09:19 pm | PVC | -- | -- | | page 13 |
| 20 | 07/30/2015 05:04:18 pm | PVC | -- | -- | | page 13 |
| 21 | 07/31/2015 04:51:55 am | PVC | -- | -- | predominant morphology | page 13 |
| 22 | 07/28/2015 11:17:52 am | Ventricular Couplet | -- | -- | | page 14 |
| 23 | 07/28/2015 11:43:23 am | Ventricular Couplet | -- | -- | | page 14 |
| 24 | 07/28/2015 03:59:35 pm | Ventricular Bigeminy | -- | -- | | page 14 |
| 25 | 07/28/2015 03:59:36 pm | Ventricular Bigeminy | -- | -- | | page 14 |
| 26 | 07/30/2015 05:05:50 am | PSVC | -- | -- | | page 15 |
| 27 | 08/03/2015 04:05:55 pm | PSVC | -- | -- | | page 15 |
| 28 | 08/03/2015 04:11:58 pm | PSVC | -- | -- | | page 15 |
| 29 | 08/03/2015 04:12:19 pm | Supraventricular Couplet | -- | -- | | page 15 |
| 30 | 08/03/2015 05:41:39 pm | Supraventricular Couplet | -- | -- | | page 15 |
| 31 | 08/04/2015 05:31:10 am | Supraventricular Couplet | -- | -- | | page 16 |

FIG. 22H

© 2019 Cardiologs Technologies

ELECTROCARDIOGRAM PROCESSING SYSTEM FOR DELINEATION AND CLASSIFICATION

CROSS-REFERENCE TO RELATED APPLICATIONS

This application is a continuation of International PCT Patent Application Serial No. PCT/IB2020/050850, filed Feb. 3, 2020, which claims priority to U.S. patent application Ser. No. 16/267,380, filed on Feb. 4, 2019, published as U.S. Patent App. Pub. No. 2019/0167143, now U.S. Pat. No. 10,959,660, the entire contents of each of which are incorporated herein by reference.

This application is also related to U.S. patent application Ser. No. 15/771,807, filed on Apr. 27, 2018, now U.S. Pat. No. 10,779,744, which is a national stage of PCT/EP2016/075972, published as WO 2017/072250, which claims priority to U.S. patent application Ser. No. 14/924,239, filed on Oct. 27, 2015, published as U.S. Patent App. Pub. No. 2017/0112401, now U.S. Pat. No. 10,426,364, and European Application Serial No. 15191769.7, filed on Oct. 27, 2015, the entire contents of each of which are incorporated herein by reference. This application is also related to PCT/EP2018/072912, filed on Aug. 24, 2018, published as WO 2019/038435, which claims priority to U.S. Provisional Application No. 62/549,994, filed on Aug. 25, 2017, the entire contents of each of which are incorporated herein by reference.

TECHNICAL FIELD

The present disclosure relates, in general, to an electrocardiogram (ECG) processing system, for example, an ECG system with artificial intelligence and having delineation, classification, embedding, and grouping machine learning functionality and facilitating visualization of a large volume of ECG related data.

BACKGROUND

An electrocardiogram (ECG) receives electrical cardiac signals from the heart that may be digitized and recorded by a computing device. An ECG typically is generated from cardiac signals sensed by a number of electrodes placed in specific areas on a patient. It is a simple, non-invasive tool, that may be used by most any healthcare professional.

A cardiac signal is composed of one or multiple synchronized temporal signals. FIG. 1A illustrates a recording of a standard 12-lead resting ECG. As is shown in FIG. 1A, each lead generates an electrical signal, resulting in 12 electrical signals. Though the ECG illustrated in FIG. 1A involves 12 leads resulting in 12 recordings, some ECGs may involve fewer leads resulting in fewer recordings. As is shown in FIG. 1A, a cardiac signal displays repeating patterns usually comprising a P-wave, a QRS complex, and a T-wave. As the name suggests, a QRS complex includes a Q-wave, an R-wave and an S-wave. An exemplary P-wave, QRS complex, and T-wave is illustrated in FIG. 1B, which focuses on a couple of beats in one lead signal, showing one R-R interval.

To make a diagnosis, a trained healthcare professional may analyze the ECG recording to identify any abnormalities and/or episodes. It is estimated that about 150 measurable abnormalities may be identified on an ECG recordings today. However, specific expertise and/or training is required to identify abnormalities from an ECG. ECG analysis is only available to those patients that can afford healthcare professions having the appropriate expertise and who otherwise have access to these professionals.

Telecardiology centers have been developed to provide ECG analysis to patients that may not otherwise have access to these trained healthcare professionals. Typically, an ECG recording is generated offsite by a non-specialist and is sent to the telecardiology center for analysis by a cardiologist or by a specialized ECG technician. While the results are generally high quality, the process may be slow and expensive.

Software systems have also been developed as an alternative to analysis by a trained professional. Current software systems provide a low quality interpretation that often results in false positives. Today, these interpretation systems may generate two types of information about a cardiac signal, (1) temporal location information for each wave, referred to as delineation, and (2) global information providing a classification of the cardiac signal or labeling its abnormalities, referred to as classification.

Concerning delineation, two main approaches are used for finding the waves of cardiac signals. The first approach is based on multiscale wavelet analysis. This approach looks for wavelet coefficients reaching predefined thresholds at specified scales. (See Martinez et al., A wavelet-based ECG delineator: evaluation on standard databases, IEEE transactions on biomedical engineering, Vol. 51, No. 4., April 2004, pp. 570-58; Almeida et al., IEEE transactions on biomedical engineering, Vol. 56, No. 8, August 2009, pp 1996-2005; Boichat et al., Proceedings of Wearable and Implantable Body Sensor Networks, 2009, pp. 256-261; U.S. Pat. No. 8,903,479 to Zoicas et al.). The usual process involves identifying QRS complexes, then P-waves, and finally T-waves. This approach is made unstable by the use of thresholds and fails to identify multiple P-waves and "hidden" P-waves.

The second delineation approach is based on Hidden Markov Models (HMM). This machine learning approach treats the current state of the signal as a hidden variable that one wants to recover (Coast et al., IEEE transactions on biomedical engineering, Vol. 37, No. 9, September 1990, pp 826-836; Hughes et al., Proceedings of Neural Information Processing Systems, 2004, pp 611-618; U.S. Pat. No. 8,332, 017 to Trassenko et al.). While this approach is an improvement upon on the first delineation approach described above, a representation of the signal must be designed using handcrafted "features," and a mathematical model must be fitted for each wave, based on these features. Based on a sufficient number of examples, the algorithms may learn to recognize each wave. This process may however be cumbersome and inaccurate due to its dependence on handcrafted features. Specifically, features which have been handcrafted will always be suboptimal since they were not learnt and the process of handcrafting features may have ignored or eliminated crucial information. Further, the model, usually Gaussian, is not well adapted. Also, the current models fail to account for hidden P waves.

Regarding classification, in current systems analysis is only performed on the QRS complex. For example, analysis of a QRS complex may detect ventricular or paced beats. The training involves handcrafted sets of features and corresponding beat labels (Chazal et al., IEEE Transactions on Biomedical Engineering, 2004, vol. 51, pp. 1196-1206). As explained above, features that have been handcrafted will always be suboptimal since they were not learnt and the process of handcrafting features may have ignored or eliminated crucial information.

To solve the above issues, recent works (Kiranyaz et al., IEEE Transactions on Biomedical Engineering, 2016, Vol. 63, pp 664-675) have turned to novel architectures called neural networks which have been intensively studied and had great results in the field of imaging (Russakovsky et al., arXiv: 1409.0575v3, 30 Jan. 2015). Neural networks learn from raw or mildly preprocessed data and thus bypass the need of handcrafted features. While the application of neural networks is an improvement on the delineation and classification approaches described above, current systems have certain drawbacks. For example, the current neural networks were only developed for QRS characterization. Further, current neural networks processes information in a beat-by-beat manner which fails to capture contextual information from surrounding beats.

Concerning identifying abnormalities and/or cardiovascular disease detection, most algorithms use rules based on temporal and morphological indicators computed using the delineation (e.g., PR interval, RR interval, QT interval, QRS width, level of the ST segment, slope of the T-wave). Often times, the algorithms are designed by cardiologists. (Prineas et al., The Minnesota Code Manual of Electrocardiographic Findings, Springer, ISBN 978-1-84882-777-6, 2009). However, the current algorithms do not reflect the way the cardiologists analyze the ECGs and are crude simplifications. For example, the Glasgow University Algorithm does not reflect the way cardiologist analyze ECGs. (Statement of Validation and Accuracy for the Glasgow 12-Lead ECG Analysis Program, Physio Control, 2009.)

More advanced methods have also been developed that use learning algorithms. In. Shen et al., Biomedical Engineering and Informatics (B MEI), 2010. vol. 3, pp. 960-964, for instance, the author used support vector machines to detect bundle branch blocks. However, in these methods, once again, it is necessary to represent the raw data in a manner that preserves the invariance and stability properties.

While more complex neural network architectures have been proposed, limitations arose when they were applied to ECGs. One team (Jin and Dong, Science China Press, Vol. 45, No 3, 2015, pp 398-416; CN104970789) proposed binary classification on a full ECG, hence providing one and only one classification for any analyzed ECG. The proposed architecture used convolutional layers which processes the leads independently before mixing them into fully connected layers. The authors also mention multi-class analysis, as opposed to binary analysis, aiming at recovering one class among several. However, they did not consider multi-label classification, wherein multiple labels (e.g., abnormalities) are assigned to a cardiac signal.

In view of the foregoing limitations of previously-known systems and methods, it would be desirable to accurately and efficiently process ECG data and to present this information in a way that is easily comprehendible. For example, it may be desirable to obtain delineation and classification of an ECG signal in a manner that does not require feature extraction, to identify hidden P-waves, to analyze an ECG signal over multiple beats, and to achieve multi-label classifications for a cardiac signal.

SUMMARY OF THE INVENTION

Provided herein are systems and methods for analyzing ECG data using machine learning algorithms and medical grade artificial intelligence with enhanced accuracy and efficiency. Specifically, systems and methods are provided for analyzing electrocardiogram (ECG) data of a patient using artificial intelligence and a substantial amount of ECG data. The systems receive ECG data from a sensing device positioned on a patient such as one or more ECG leads. The system may include an application that communicates with an ECG platform running on a server that processes and analyzes the ECG data, e.g., using neural networks for delineation of the cardiac signal and classification of various abnormalities, conditions and/or descriptors. The ECG platform may be a cloud-based ECG platform that processes and analyzes the ECG data in the cloud. The processed ECG data is communicated from the server for display in a user-friendly and interactive manner with enhanced accuracy. Together the ECG application and ECG platform implement the ECG processing system to receive ECG data, process and analyze ECG data, display ECG data on a system device, and generate a report having ECG data.

A computerized-system is provided herein for analyzing ECG data of a patient generated by one or more electrodes across a plurality of time points and comprising a plurality of beats. The computerized-system may be designed to analyze the ECG data using a delineation algorithm to generate wave information corresponding to a likelihood of a presence of at least one wave at the plurality of time points and further to determine beat onset information and beat offset information for beats of the plurality of beats where at least one wave is determined to be present to generate a plurality of beat onsets and beat offsets. The computerized system may further be designed to extract a plurality of beat portions of ECG data based on the plurality of beat onsets and beat offsets, each beat portion of the plurality of beat portions of ECG data corresponding to a beat of the plurality of beats, and determine that at least two beats of the plurality of beats should be grouped together based on the plurality of beat portions of ECG data, the at least two beats forming a cluster. Determining that the at least two beats of the plurality of beats should be grouped together may involve determining that the group data satisfies a threshold value.

The computerized-system may further be designed to analyze the plurality of portions of ECG data using an embedding algorithm to generate embedding data representative of the plurality of beats, and analyze the embedding data using a grouping algorithm to generate group data. The at least two beats of the plurality of beats may be determined to be grouped together based on the group data. The group data may correspond to a distance between two beats. The delineation algorithm may utilize a first neural network and the embedding algorithm may utilize a second neural network. The grouping algorithm may utilize a third neural network. The computerized-system may further be designed to receive user input data from an input device regarding an inaccuracy corresponding to displayed data related to the ECG data. The computerized-system may further be designed to adjust one or more of the delineation algorithm, embedding algorithm, or grouping algorithm based on the user input data.

The computerized-system may further be designed to modify the displayed data based on the user input data. The user input data may correspond to adding, deleting, or splitting one or more QRS clusters, PVC clusters, or PAC clusters. The embedding data may involve a vector of data for each beat of the plurality of beats. The computerized-system may further be designed to transmit information indicative of the cluster to a computer for display on a graphic user interface. The computerized-system may further be designed to generate information to display at least one overlay comprising at least two beats of the plurality of beats overlaid over one another. The computerized-system may further be designed to analyze the beats in the cluster using a classification algorithm to determine a likelihood of a presence of the one or more abnormalities, conditions, or descriptors associated with cardiac events for the patient.

The computerized-system may further be designed to analyze the wave information from the delineation algorithm using a classification algorithm to determine a likelihood of a presence of the one or more abnormalities, conditions, or descriptors associated with cardiac events for the patient. The wave information may be inputted into the classification algorithm and separately used to determine that at least two beats of the plurality of beats should be grouped together. The computerized-system may further be designed to, prior to analyzing the ECG data using the delineation algorithm, pre-process the ECG data to remove noise from the ECG data. The computerized-system may assign the ECG data and information based on the ECG data to a user account for review. The computerized may receive user input data regarding the ECG data and information based on the ECG data from the user account based on the review.

A method for analyzing electrocardiogram (ECG) data of a patient generated by one or more electrodes across a plurality of time points and comprising a plurality of beats is described herein. The method may involve analyzing the ECG data using a delineation algorithm to generate wave information corresponding to a likelihood of a presence of at least one wave at the plurality of time points, and determining beat onset information and beat offset information for beats of the plurality of beats where at least one wave is determined to be present to generate a plurality of beat onsets and beat offsets. The method may further involve extracting a plurality of beat portions of ECG data based on the plurality of beat onsets and beat offsets, each beat portion of the plurality of beat portions of ECG data corresponding to a beat of the plurality of beats, and determining that at least two beats of the plurality of beats should be grouped together based on the plurality of beat portions of ECG data, the at least two beats forming a cluster.

The method may further involve analyzing the plurality of portions of ECG data using an embedding algorithm to generate embedding data representative of the plurality of beats, and analyzing the embedding data using a grouping algorithm to generate group data. The at least two beats of the plurality of beats may be determined to be grouped together based on the group data. The method may further involve assigning the ECG data and information based on the ECG data to a user account for review of the ECG data. The method may further involve submitting the ECG data and information based on the ECG data for quality review by one or more reviewers. The method may further involve receiving quality control input generated by the one or more reviewers. The method may further involve causing display of the quality control input for additional quality control review. The method may further involving receiving user input data from an input device regarding an inaccuracy corresponding to information based on the ECG data. The method may further involve adjusting one or more of the delineation algorithm, embedding algorithm, or grouping algorithm based on the user input data. The method may further involve assigning the displayed data to a user account for quality review.

A system for analyzing ECG data of a patient may, in one example, involve a first plurality of instructions designed to, when executed, obtain ECG data of the patient over a plurality of time points and may further cause transmission of the ECG data to at least one server. The ECG data may be sampled at a predetermined sampling rate such as a rate of at least 20 samples per second. The system for analyzing ECG data may further involve a second plurality of instructions designed to, when executed, cause the at least one server to receive the ECG data of the patient, analyze the ECG data of the patient using at least one algorithm trained from a plurality of ECG data sets from different patients, quantify a likelihood of a presence of one or more abnormalities, conditions, or descriptors, or any combination thereof, and transmit information corresponding to the presence of the one or more abnormalities, conditions, or descriptors, or any combination thereof, to a computer remote from the at least one server for display.

The system for analyzing ECG data may further involve a third plurality of instructions designed to, when executed by the computer, cause the computer to display information corresponding the presence of the one or more abnormalities, conditions, or descriptors, or any combination thereof, based on the transmitted information from the at least one server. It is understood that each set of the plurality of ECG data sets from the different patients may be generated at a sampling rate equal to the rate used to obtain the ECG data. It is further understood that the computer that executes the third plurality of instructions may also execute the first plurality of instructions.

The second plurality of instructions may, when executed, further cause the at least one server to pre-process the ECG data which may involve removing noise from the ECG data or expressing the ECG data at a predetermined baseline frequency. Further, the second plurality of instructions, when executed, may analyze the ECG data of the patient using at least one algorithm that applies the ECG data to a first neural network for delineation and may further quantify a likelihood of a presence of at least one of a P-wave, QRS complex, or T-wave at each of the plurality of time points. The second plurality of instructions may further calculate at least one onset and at least one offset for at least one of the P-wave, QRS-complex, or T-wave, and/or calculate at least one measurement from one or more of the onset, the offset, or the output of the first neural network.

It is further understood that the second plurality of instructions may, when executed, analyze the ECG data of the patient using at least one algorithm that applies the ECG data to a second neural network for classification. Specifically, the second plurality of instructions may quantify a likelihood of a presence of the one or more abnormalities, conditions, or descriptors, and may apply a threshold to at least one value in the output of the second neural network and assign at least one label corresponding to the one or more abnormalities, conditions, or descriptors if the value exceeds a threshold. The second plurality of instructions may also post-process the ECG data by removing redundant labels.

The system may further include a fourth and/or fifth plurality of instructions. The fourth plurality of instructions may, when executed, cause the at least one server to generate a report including at least the transmitted information corresponding to the presence of the one or more abnormalities, conditions, or descriptors. The fifth plurality of instructions may, when executed, receive user input related to the ECG data and cause the computer to transmit the user input to the at least one server such that the at least one server uses the user input to generate the report. The report may include at least one heart rate density plot representing density of heart rates of the patient as a function of time. It is understood that a third plurality of instructions is further configured to, when executed by the computer, cause the computer to display a heart rate density plot representing density of heart rates of the patient as a function of time.

A system for analyzing ECG data of a patient may, in another example, involve instructions stored on at least one server that are designed to, when executed, cause the at least one server to receive a set of ECG data of the patient over a plurality of time points. The set of ECG data may be sampled at a predetermined sampling rate such as a rate of at least 20 samples per second. The instructions may further be designed to cause the at least one server to analyze the set of ECG data of the patient using at least one algorithm, quantify, at each time point of the plurality of time points, a likelihood of a presence of one or more abnormalities, conditions, or descriptors, or any combination thereof and transmit information corresponding to the likelihood of the presence of the one or more abnormalities, conditions, or descriptors to a computer for display. The at least one algorithm may be trained using a plurality of sets of ECG data generated at a sampling rate of at least 20 samples per second from different patients.

A computerized-method for analyzing ECG data of a patient may similarly involve receiving a set of ECG data of the patient over a plurality of time points sampled at a sample rate and analyzing the set of ECG data of the patient using at least one algorithm trained using a plurality of sets of ECG data. Each set in the plurality of sets of ECG data may be generated at the same sample rate from different patients. The computerized method for analyzing ECG data may further involve identifying, at each time point, one or more abnormalities, conditions or descriptors, or any combination thereof and further may involve transmitting information including the one or more abnormalities, conditions, or descriptors, or any combination thereof to a computer for display. It is understood that the computerized-method may involve analyzing an entire set of sampled ECG data without discarding data from the set of ECG data. The computerized-method may, in one example, involve a sample rate of at least 20 samples per second.

The computerized-method may further involve assigning the set of ECG data and information based on the set of ECG data to a user account for review of the ECG data. The computerized-method may further involve submitting the set of ECG data and information based on the set of ECG data for quality review by one or more reviewers. The computerized-method may further involve receiving quality control input generated by the one or more reviewers. The method may further involve causing display of the quality control input for additional quality control review.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

FIGS. 15A-15D is an exemplary report generated by the ECG processing system having information corresponding to the patient and processed ECG data and displaying a heart rate density plot and ECG strips.

The foregoing and other features of the present invention will become apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION OF THE INVENTION

The present invention is directed to an electrocardiogram (ECG) processing system having medical grade artificial intelligence involving an ECG application run on a system device and an ECG platform run on a server(s). The ECG application and ECG platform implement the ECG processing system by processing and analyzing the ECG data using machine learning algorithms to achieve delineation of the cardiac signal and classification of various abnormalities, conditions, and descriptors. The server(s) may be located in a different location than the system device(s) and the servers need not be in the same physical location as one another (e.g., the server(s) may be a remote server(s)). Alternatively, the server(s) and the system device(s) may be located in the same general area (e.g., on a local area network (LAN)). The ECG platform may be a cloud-based ECG platform that may implement the ECG processing system by processing and analyzing the ECG data in the cloud.

To implement the ECG processing system, ECG application running on the system device may receive ECG data (i.e., cardiac signal) from a sensing device and may transmit the ECG data to a ECG platform running on the server. The ECG platform may execute a first and second neural network and may apply the ECG data to the first and second neural network. The first neural network may be a delineation neural network having machine learning functionality. The second neural network may be a classification neural network having machine learning functionality. The output of the first and/or second neural networks may be processed by the ECG platform to achieve delineation and classification of the ECG data. The ECG data and/or data generated by the ECG platform may be communicated from the ECG platform to the ECG application. The ECG application may cause the ECG data and/or data generated by the ECG platform to be displayed in an interactive manner. The ECG platform may generate reports including ECG data and/or data generated by the ECG platform, and may communicate the reports to the ECG application.

Figure 1A:
FIG. 1A is a recording of a standard 12-lead resting ECG and FIG. 1B is a recording of an exemplary P-wave, QRS complex and T-wave.
Figure 1B:
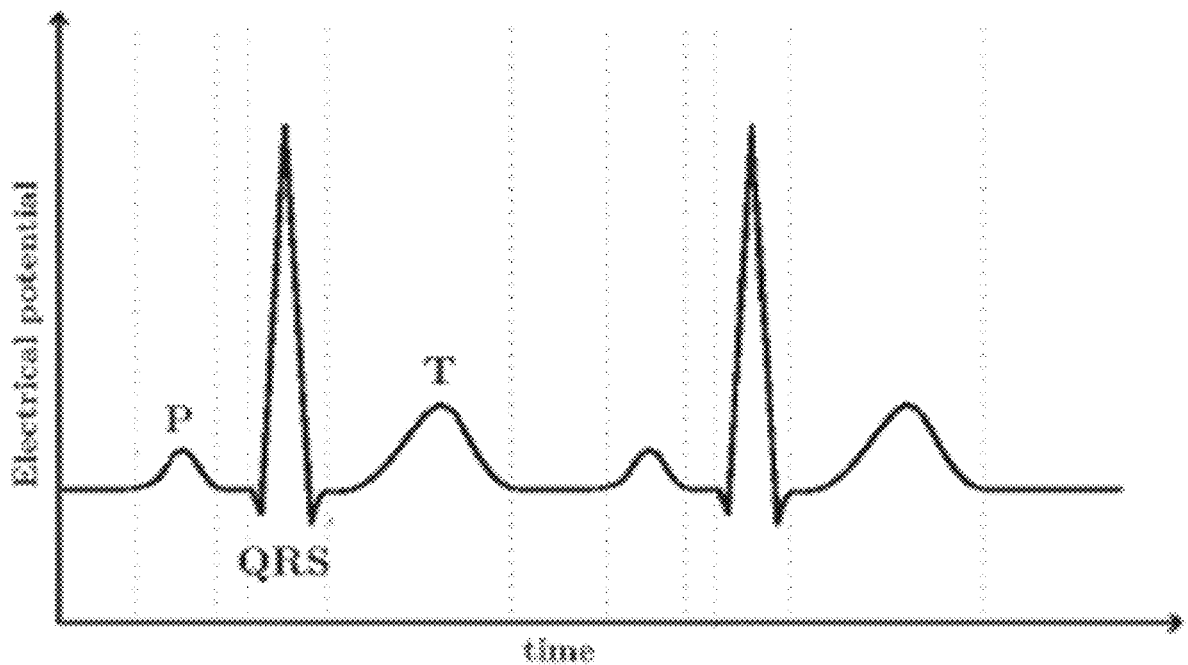
Figure 2:
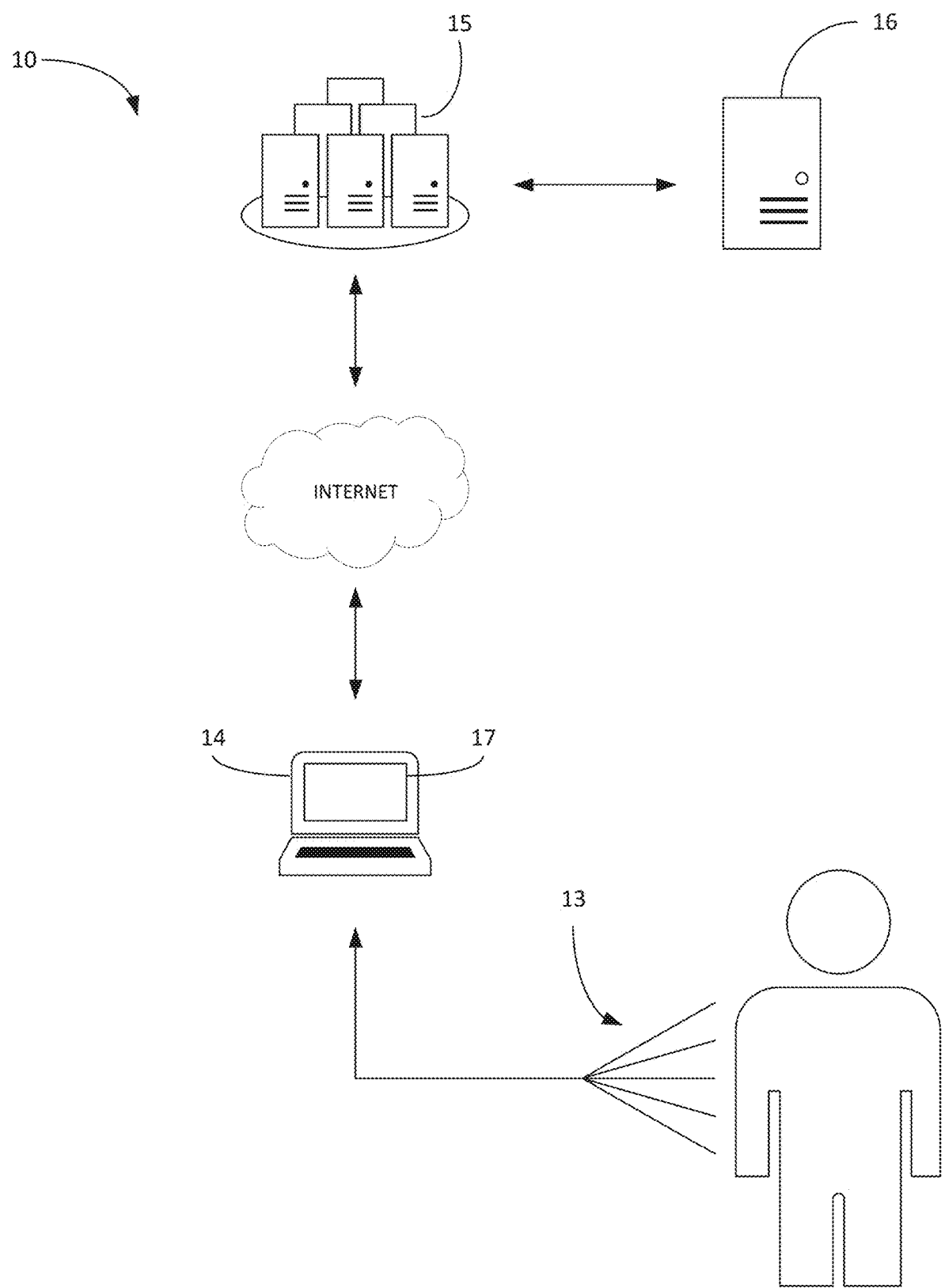
FIG. 2 is a diagram illustrating exemplary components for executing systems and methods in accordance with aspect of the present disclosure.

Referring now to FIG. 2, exemplary components for executing electrocardiogram (ECG) processing system 10 are illustrated. FIG. 2 shows ECG sensing device 13, system device 14, and server 15, as well as drive 16.

ECG sensing device 13 is designed to sense the electrical activity of the heart for generating ECG data. For example, sensing device 13 may be one or more electrodes that may be disposed on one or more leads. ECG sensing device 13 may be an ECG-dedicated sensing device such as a conventional 12-lead arrangement or may be a multi-purposes device with sensing hardware for sensing electrical activity of the heart for ECG generation such as the Apple Watch available from Apple, Inc., of Cupertino, California Sensing device 13 may be placed on the surface of the chest of a patient and/or limbs of a patient. Sensing device 13 may be in electrical communication with system device 14 running the ECG application 29 such that the electrical signal sensed by sensing device 13 may be received by the ECG application 29. ECG application 29 may include instructions that cause sensing device 13 to sense or otherwise obtain ECG data.

System device 14 is preferably one or more computing devices (e.g., laptop, desktop, tablet, smartphone, smartwatch, etc.) having the components described below with reference to FIG. 3A and the functionality described herein. System device 14 running ECG application 29 may connect with server 15 running ECG platform 37 via any well-known wired or wireless connection. For example, system device 14 may connect to the Internet using well known technology (e.g., WiFi, cellular, cable/coaxial, and/or DSL) and may communicate with server 15 over the Internet.

Server 15 is preferably one or more servers having the components described below with reference to FIG. 3B and the functionality described herein. Server 15 preferably has processing power superior to system device 14 such that server 15 can process and analyze cardiac signals having a sampling rate above a predetermined threshold, such as at least 20 samples per second, at least 250 samples per second, or at least 1000 samples per second. As will be readily apparent to one skilled in the art, server 15 may include a plurality of servers located in a common physical location or in different physical locations. In a preferred embodiment, server 15 is located in a different, remote location (e.g., on the cloud) than system device 14, although server 15 and system device 14 may be located in a common location (e.g., on a local area network (LAN)).

Server 15 may optionally communicate with drive 16 which may be one or more drives having memory dedicated to storing digital information unique to a certain patient, professional, facility and/or device. For example, drive 16 may include, but is not limited to, volatile (e.g. random-access memory (RAM)), non-volatile (e.g. read-only memory (ROM)), flash memory, or any combination thereof. Drive 16 may be incorporated into server 15 or may be separate and distinct from server 15 and may communicate with server 15 over any well-known wireless or wired connection.

Figure 3A:
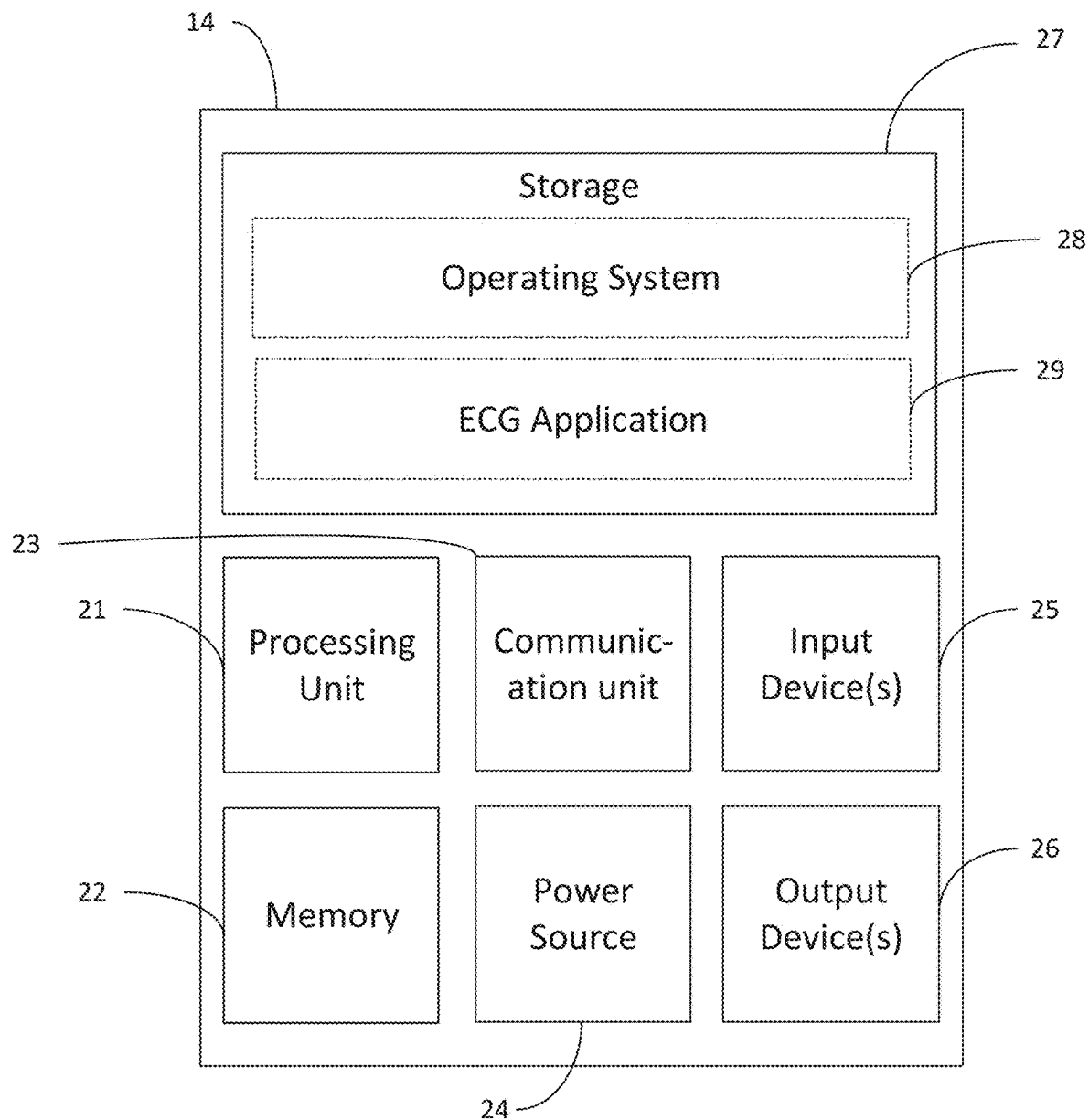
FIGS. 3A-3B are schematic views of the exemplary hardware and software components of an exemplary system device and an exemplary server, respectively.
Figure 3B:
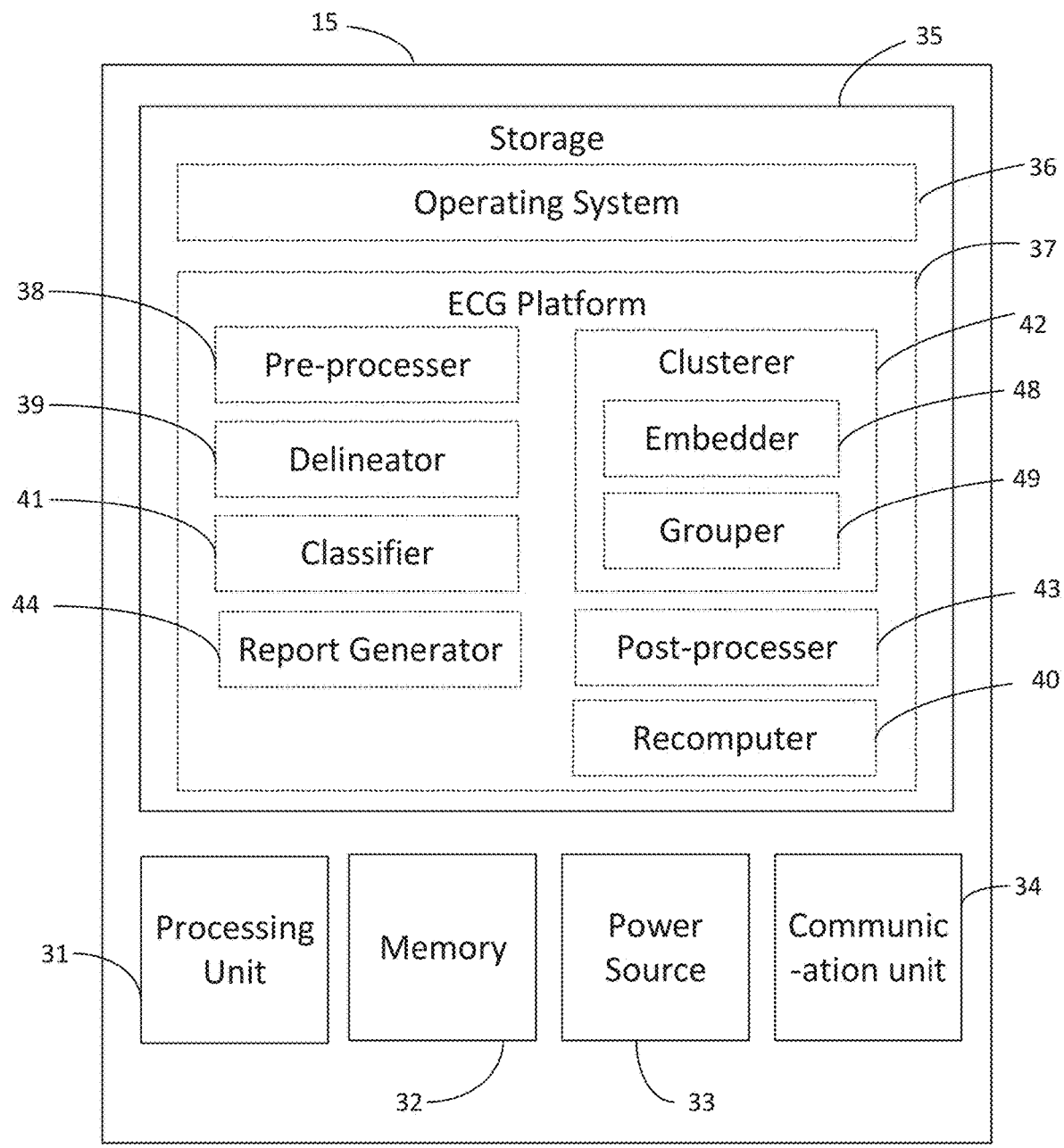

Referring now to FIGS. 3A-3B, exemplary functional blocks representing the hardware and software components of system device 14 and server 15 are shown. Referring now to FIG. 3A, hardware and software components of system device 14 may include one or more processing unit 21, memory 22, storage 27, communication unit 23, and power source 24, input devices 25 and output devices 26.

Processing unit 31 may be one or more processors configured to run collaboration operating system 28 and ECG application 29 and perform the tasks and operations of system device 14 set forth herein. Memory 22 may include, but is not limited to, volatile (e.g. random-access memory (RAM)), non-volatile (e.g. read-only memory (ROM)), flash memory, or any combination thereof. Communication unit 23 may receive and/or transmit information to and from other components in ECG processing system 10 including, but not limited to, sensing device 13 and server 15. Communication unit 23 may be any well-known communication infrastructure facilitating communication over any well-known wired or wireless connection, including over any well-known standard such as any IEEE 802 standard. Power source 24 may be a battery or may connect system device 14 to a wall outlet or any other external source of power. Storage 27 may include, but is not limited to, removable and/or non-removable storage such as, for example, magnetic disks, optical disks, or tape.

Input device 25 may be one or more devices coupled to or incorporated into system device 14 for inputting data to system device 14. Input device 25 may further include a keyboard, a mouse, a pen, a sound input device (e.g., microphone), a touch input device (e.g., touch pad or touch screen), a location sensor, and/or a camera, for example. Output device 26 may be any device coupled to or incorporated into system device 14 for outputting or otherwise displaying data and includes at least a display 17. Output device 26, may further include speakers and/or a printer, for example.

ECG application 29 may be stored in storage 27 and executed on processing unit 21. ECG application 29 may be a software application and/or software modules having one or more sets of instructions suitable for performing the operations of system device 14 set forth herein, including facilitating the exchange of information with sensing device 13 and server 15. For example, ECG application 29 may cause system device 14 to receive ECG data from sensing device 13, to record ECG data from sensing device 13, to communicate ECG data to server 15, to instruct server 15 to process and analyze ECG data, to receive processed and/or analyzed ECG data from server 15, to communicate user input regarding report generation to server, and to generate a graphic user interface suitable for displaying raw, analyzed and/or processed ECG data and data related thereto.

Operating system 28 may be stored in storage 27 and executed on processing unit 21. Operating system 28 may be suitable for controlling the general operation of system device 14 and may work in concert with ECG application 29 to achieve the functionality of system device 14 described herein. System device 14 may also optionally run a graphics library, other operating systems, and/or any other application programs. It of course is understood that system device 14 may include additional or fewer components than those illustrated in FIG. 3A and may include more than one of each type of component.

Referring now to FIG. 3B, hardware and software components of server 15 may include one or more processing unit 31, memory 32, storage 35, power source 33, and communication unit 34. Processing unit 31 may be one or more processors configured to run operating system 36 and ECG platform 37 and perform the tasks and operations of server 15 set forth herein. Given the volume of data and processing tasks assigned to processing unit 31, it is understood that processing unit 31 has superior processing power compared to processing unit 21.

Memory 32 may include, but is not limited to, volatile (e.g. random-access memory (RAM)), non-volatile (e.g. read-only memory (ROM)), flash memory, or any combination thereof. Storage 35 may include, but is not limited to, removable and/or non-removable storage such as, for example, magnetic disks, optical disks, or tape. Communication unit 34 may receive and/or transmit information to and from other components of ECG processing system 10 including, but not limited to, system device 14 and/or drive 16. Communication unit 34 may be any well-known communication infrastructure facilitating communication over any well-known wired or wireless connection. Power source 33 may be a battery or may connect server 15 to a wall outlet or other external source of power.

Operating system 36 and ECG platform 37 may be stored in storage 35 and executed on processing unit 31. Operating system 36 may be suitable for controlling general operation of server 15. ECG platform 37 may be a software application and/or software modules having one or more sets of instructions. ECG platform 37 may facilitate and oversee the processing and analysis of ECG data received from system device 14, report generation, and otherwise may be suitable for performing the operations of server 15 set forth herein.

ECG platform 37 may include several sub-modules and/or applications including, but not limited to, pre-processor 38, delineator 39, classifier 41, clusterer 42 which may include embedder 48 and grouper 49, post-processor 43, report generator 44 and recomputer 40. Each sub-module and/or application may be a separate software application and/or module having one or more sets of instructions. Pre-processor 38 may pre-process raw ECG data, delineator 39 may execute a first neural network to achieve delineation, classifier 41 may execute a second neural network to achieve classification, clusterer 42 may identify clusters in data processed by the first neural network, post-processor 43 may post-process data processed by the second neural network, embedder 48 may execute one or more algorithms and/or a third neural network to achieve embedding, grouper 49 may execute one or more algorithms and/or a fourth neural network to generate cluster groups, report generator 44 may generate reports based on raw ECG data and ECG data processed by ECG platform 37, and recomputer 40 may recompute and/or adjust embedder 48 and/or grouper 49 based on user input data. For example, recomputer 40 may recalculate episodes based on corrected wave information. ECG platform 37 may also perform various other functions including, but not limited to, receiving requests from system device 14 to process and/or analyze ECG data, communicating processed and/or analyzed ECG data to system device 14, receiving a request to generate a report, requesting and/or receiving user interaction and/or instructions from system device 14, receiving user input data and/or instruction information from system device 14 regarding report generation, and/or communicating a report to system device 14.

Server 15 may also optionally run a graphics library, other operating systems, and/or any other application programs. It of course is understood that server 15 may include additional or fewer components than those illustrated in FIG. 3B and may include more than one of each type of component.

Figure 4:
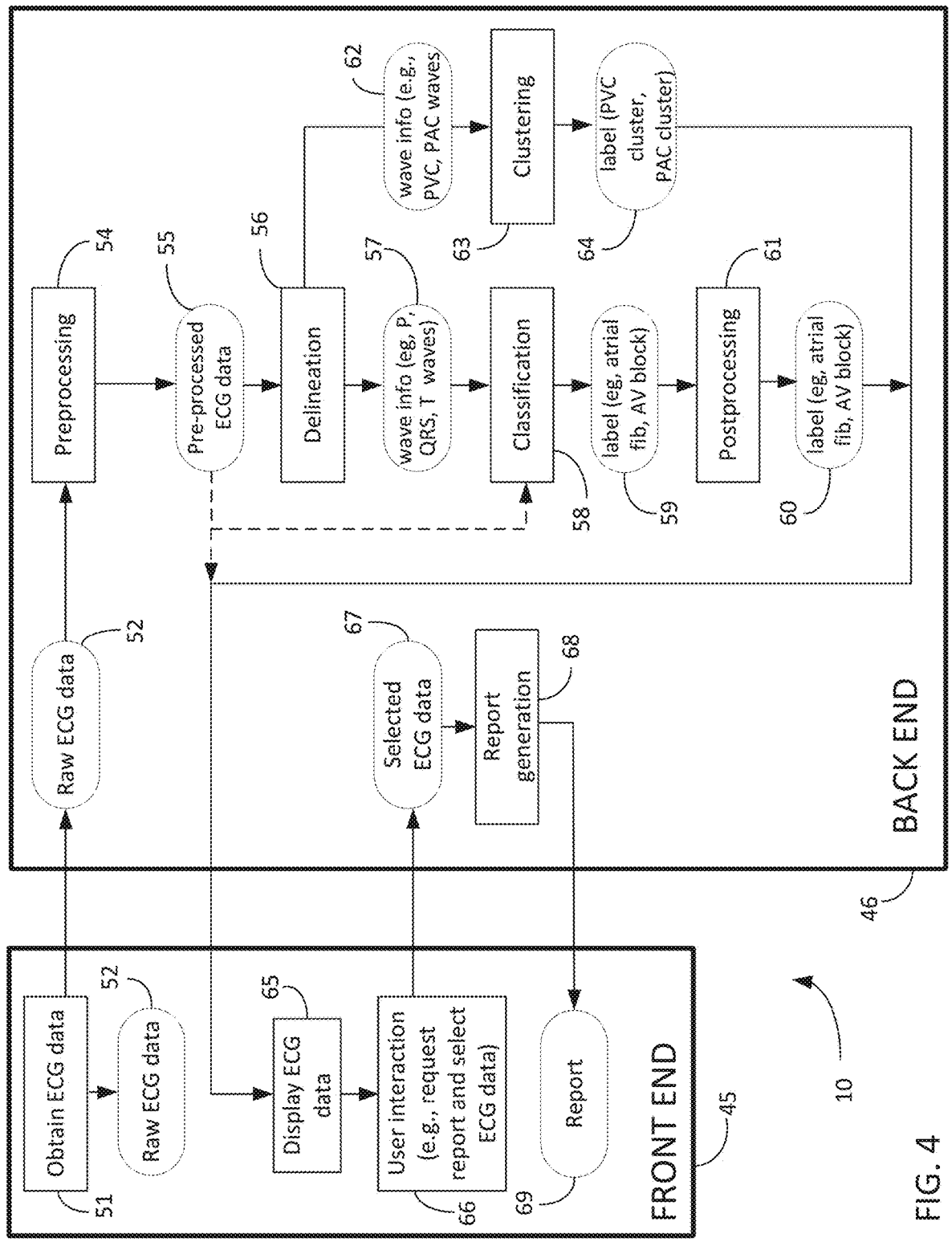
FIG. 4 is a flow chart of an exemplary method of processing ECG data using, displaying ECG data, and generating a report including ECG data.

FIG. 4 illustrates an exemplary process for implementing ECG processing system 10 to receive and record ECG data, process and analyze ECG data, and generate reports involving ECG data, and further shows the flow of information between front end 45 and back end 46 of ECG processing system 10. Front end 45 includes at least ECG application 29 running on system device 14. Back end 46 includes at least ECG platform 37 running on server 15.

As is shown in FIG. 4, at step 51, ECG application 29 may cause system device 14 to receive and/or otherwise obtain raw ECG data 52 from sensing device 13. For example, ECG application 29 may cause sensing device 13 to sense the cardiac signal and communicate the cardiac signal sensed by sensing device 13 to system device 14. Raw ECG data is the cardiac signal sensed by sensing device 13. Raw ECG data 52 has not been processed or analyzed by ECG processing system 10. Raw ECG data 52 preferably involves data sampled multiple times per heartbeat over a plurality of heartbeats. It is understood that sensing device 13 may convert an analog cardiac signal into a digital signal, a different component not shown in FIG. 2 may convert the analog cardiac signal to a digital signal, or ECG application 29 may cause system device 14 to convert the analog cardiac signal to a digital signal. Raw ECG data in both analog and digital form are referred to herein as raw ECG data 52.

Upon receiving raw ECG data 52, ECG application 29 may cause system device 14 to record raw ECG data 52 and may optionally save some or all of raw ECG data 52 to system device 14. As explained above, the signals may correspond to one or more leads. When multiple leads are used, all leads may be processed simultaneously. It is understood that the cardiac signal generated by each lead may have varying lengths. It is further understood that the cardiac signal may be short term (e.g., 10 seconds in standard ECGs) or long term (several days in holters). System device 14 may optionally display raw ECG data 52 or a portion thereof on display 17.

As is shown in FIG. 4, raw ECG data 52 may be transmitted from front end 45 to back end 46. Specifically, ECG application 29 may cause system device 14 to communicate raw ECG data 52 to ECG platform 37 running on server 15. Upon receiving raw ECG data 52, ECG platform 37 may cause server 15 to save some or all of raw ECG data 52 to server 15. Further, after receiving raw ECG data 52, ECG platform 37 cause raw ECG data 52 to be preprocessed at step 54 by pre-processor 38. It is understood that pre-processor 38 may be a stand-alone component of ECG platform 37 or subcomponent of delineator 39.

Pre-processor 38 may process raw ECG data 52 or a portion thereof by removing the disturbing elements of the cardiac signal, such as noise from the raw ECG data. For noise filtering, a multivariate functional data analysis approach may be used (Pigoli and Sangalli. Computational Statistics and Data Analysis, Vol. 56, 2012, pp 1482-1498). As the signal sensed by sensing device 13 may vary due to a patient's movements, the baseline frequency of raw ECG data 52 may be removed by pre-processor 38 and the cardiac signal may be expressed at a chosen frequency. The frequencies of the signal corresponding to the patient's movements may be removed using median filtering (Kaur et al., Proceedings published by International Journal of Computer Applications, 2011, pp 30-36). Applying raw ECG data 52 to pre-processor 38 generates pre-processed ECG data 55. At this point, ECG platform 37 may cause pre-processed ECG data 55 to optionally be communicated to ECG application 29 running on system device 14 for display on display 17. ECG platform 37 may alternatively, or additionally, cause pre-processed ECG data 55 to be used as an input at classification step 58, discussed in more detail.

At step 56, ECG platform 37 causes pre-processed ECG data 55 to be applied to delineator 39 for delineation. Delineator 39 applies a first neural network that is a delineation neural network to pre-processed ECG data 55. A neural network refers to a mathematical structure or algorithm that may take an object (e.g., matrix or vector) as input and produce another object as an output though a set of linear and non-linear operations called layers. For example, the input of the first neural network may be one or more multi-lead cardiac signals that are pre-processed to remove noise and/or baseline wandering.

To apply pre-processed ECG data 55 to the first neural network, delineator 39 may cause some or all of raw ECG data 52 to be expressed as matrix X, which may be a matrix of real numbers. For example, matrix X may be a matrix of size m×n at the frequency used for training the networks, described in more detail below. The constant "m" may be a number of leads in sensing device 13, which is typically 12, though any number of leads may be used. In this example, the number of samples "n" provides the duration of the cardiac signal "n/f" with f being the sampling frequency of the cardiac signal. The sample rate is above a predetermined rate and is preferably relatively high, such as, for example, at least 20, at least 250, at least 500 or at least 1000 samples per second, etc. In one embodiment, all of the sampled ECG data is transferred to the server for input into the processing algorithms without filtering out ECG data. While the ECG data applied to the first neural network is preferably pre-processed ECG data 55, it is understood that a non-preprocessed cardiac signal (i.e., raw ECG data 52, or a portion thereof) may be applied to the first neural network.

The first neural network may provide as an output, values corresponding to the likelihood of the presence of or one or more waves at a plurality of time points in the cardiac signal. The time points may be dictated by the raw ECG data, may be selected by the user of system device 14, or may be preprogrammed. The first neural network may be a convolutional neural network, and is preferably a fully convolutional neural network. Convolutional neural networks are a particular type of neural network where one or more matrices, which are learned, do not encode a full linear combination of the input elements, but the same local linear combination at all the elements of a structured signal, such as a cardiac signal, through a convolution (Fukushima, Biol. Cybernetics, Vol. 36, 1980, pp 193-202, LeCun et al., Neural Computation, Vol. 1, 1989, pp 541-551). A network which only contains convolutional networks is called a fully convolutional neural network.

Accordingly, at step 56, delineator 39 causes the first neural network to read each time point of the cardiac signal, spatio-temporally analyze each time point of the cardiac signal, and assign a score at each time point corresponding to one or more types of waves. In this manner, all types of waves in the cardiac signals may analyzed and the likelihood of their presence at each time point, quantified, in a single step. Accordingly, each score generated by delineator 39 is indicative of the likelihood of the presence of a particular wave type at a given time point of the cardiac signal. The wave types may be any well know wave type such as, P-waves, Q-wave, R-wave, S-wave, Q-waves, R-waves, S-waves, QRS complexes, and/or T-waves, for example. In this manner, delineator 39 may process data sampled multiple times per heart beat across a plurality of heart beats.

The output of the first neural network may be a matrix Y, which may be a matrix of real numbers. For example, matrix Y may be a matrix of the size p×n. Matrix Y may include scores for each type of wave at each time point of the cardiac signal. In matrix Y, "n" is the number of samples, as discussed above with respect to Matrix X, and "p" is the number of wave types plus the number of wave characterizations. As explained in more detail below, wave characterization may correspond to conductivity, prematurity, ectopy, and/or origin of the waves in the cardiac signal, for example. In one example, the wave types include (1) P-waves, (2) QRS complexes, and (3) T-waves, and the wave characterizations include (1) premature waves, (2) paced waves, (3) ventricular QRS complexes, (4) junctional QRS complexes, (5) ectopic P waves, and (6) non-conducted P waves. Accordingly, in this example, p=3+6=9. Each wave type may be expressed according to certain characteristics of that wave, such as start and end points (i.e., onset and offset)).

Figure 5A:
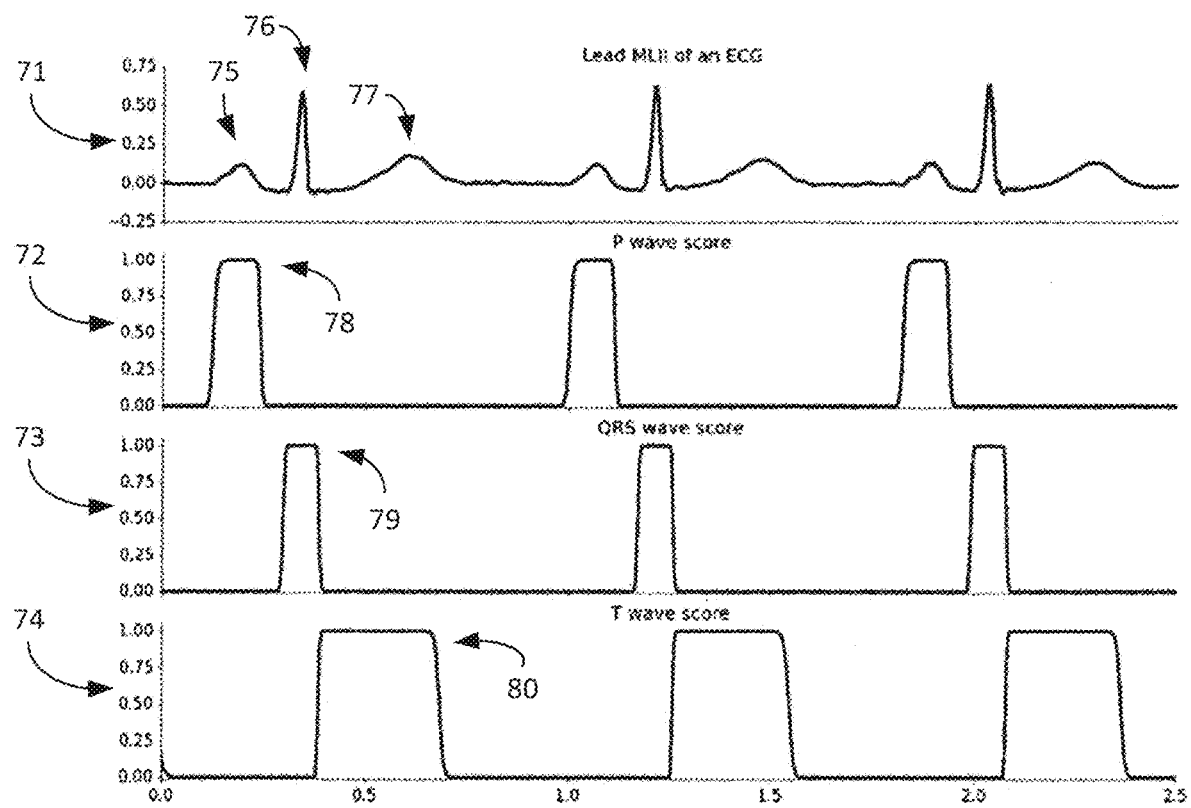
FIGS. 5A-5B are line graphs representing an exemplary ECG signal and an exemplary output of a first neural network for each wave type analyzed, respectively.
Figure 5B:
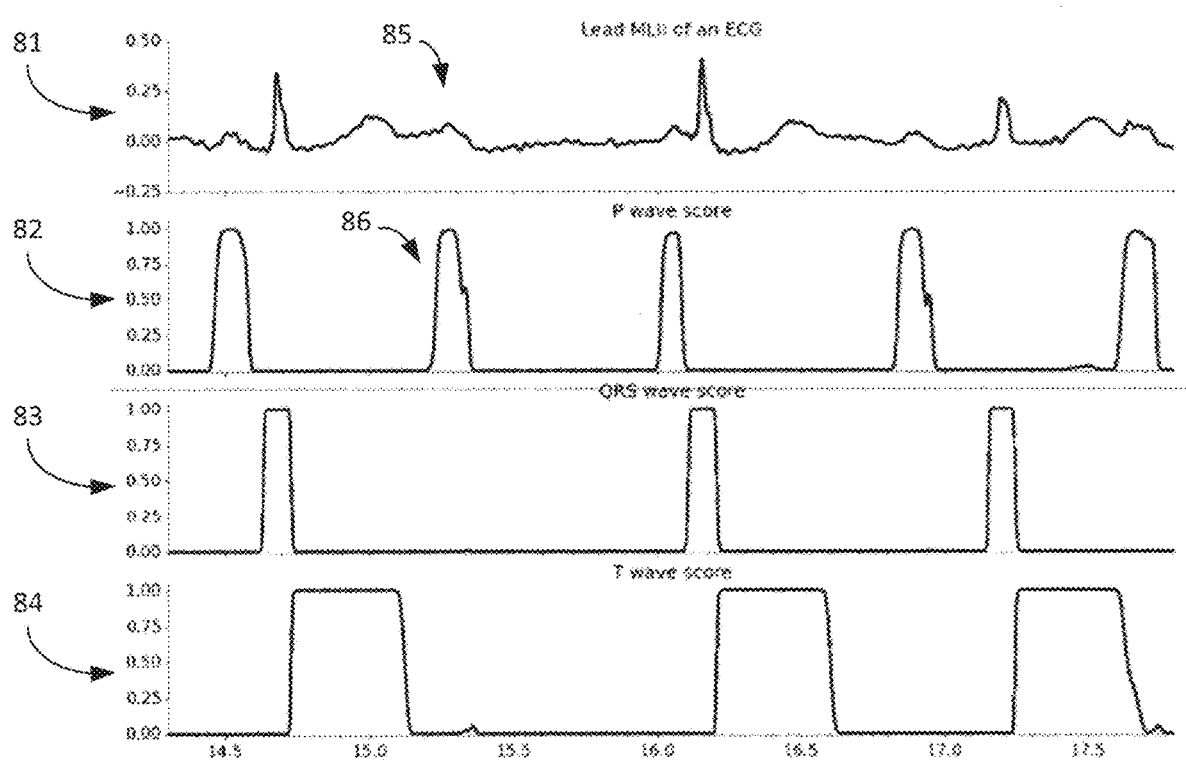

Referring now to FIGS. 5A and 5B, exemplary outputs of the first neural network are graphed for each wave type to illustrate the value of generating scores at each time point corresponding to a plurality of types of waves. Specifically, FIG. 5A illustrates an exemplary output where the delineation neural network processed a normal cardiac signal (with no abnormalities) and FIG. 5B illustrates an exemplary output where the delineation neural network processed a cardiac signal having "hidden" P-waves, for example due to an atrioventricular block.

Referring now to FIG. 5A, four line graphs are illustrated, each graph showing time on the x-axis. Line graph 71 represents the cardiac signal over multiple beats. The plotted signal reflects the well-known ECG waveform having a P-Wave (point 75), QRS complex (point 76), and T-wave (point 77). Line graph 72 is a graph the P-wave score over the same time points in the cardiac signal. Similarly, line graph 73 and line graph 74 are graphs of the QRS score and T-wave scores, respectively, over the same time points. The y-axis for each line graphs 72-74 is the score assigned at each time point, ranging from 0 to 1, with 0 indicating a low likelihood of the presence of a particular wave and 1 indicating a high likelihood of the presence of a particular wave. For example, line graph 72 indicates a very high likelihood of the presence of P-waves at score 78 which corresponds to the time points near point 75, line graph 73 indicates a very high likelihood of the presence of a QRS complex at score 79 which corresponds to the time points near point 76, and line graph 74 indicates a very high likelihood of the presence of a T-wave at score 80 which corresponds to the time points near point 77.

FIG. 5B, like FIG. 5A, illustrates four line graphs, line graphs 81-82, which are similar to line graphs 71-74. Specifically, line graph 81 represents the cardiac signal over several beats, line graph 82 represents the P-wave score over the cardiac signal, line graph 83 represents the QRS score over the cardiac signal, and line graph 84 illustrates the T-wave score over the cardiac signal. Unlike FIG. 5A, the ECG signal in line graph 81 includes hidden P-waves such as the hidden P-wave shown at point 85. Hidden P-waves are P-waves that occur during another wave or complex such as a T-wave. As the cardiac signal processed by the delineation network involves a high sample rate and the delineation network generates data for each wave type at each time point, the output recovered is robust enough (i.e., includes enough sample points) to identify two waves occurring at the same time, such as the case with hidden P-waves. For example, line graph 82 indicates a very high likelihood of the presence of P-waves at score 86 which corresponds to the time points near point 85. Accordingly, it is understood that the delineation neural network is not limited to recovering only one wave at each time point and therefore can identify several waves at any time point. It is further understood that signals from one or more leads may be processed simultaneously by the first neural network.

Using the scores assigned to each time point corresponding to each wave type (e.g., P-wave, QRS complex, T-wave, etc.), delineator 39 may post-process the cardiac signal. Post-processing involves, assigning to each time point, none, one, or several waves, calculating the onset and offset of each of the identified waves, and optionally determining the characterization of the waves. Waves may be assigned to each time point by determining that a wave exists at that time point if a certain value is achieved. Computing the "onset" and "offset" of each wave involves computing the time points of the beginning and the end of each wave in the cardiac signal, the beginning referred to as the "onset" and the end referred to as the "offset." This may involve analyzing the time points corresponding begging and end of the highest values for each wave type. Delineator 39 may characterize the waves by identifying prematurity, conductivity and ectopy. Wave characterization leverages the contextual information between each wave and/or each beat. For example, the premature label may be applied to the wave if a certain threshold value is achieved at a certain time point or an average value over several time points.

After computing the onset and offset of each wave type in the cardiac signal, delineator 39 may calculate global measurements. Global measurements are derived from the onset and offset of each wave type and may relate to features and characteristics of the cardiac signal such as intervals between waves and wave durations. For example, global measurements may include, but are not limited to, PR interval, P-wave duration, QRS complex duration, QRS axis, QT interval, corrected QT interval (Qtc), T-wave duration, JT interval, corrected JT interval, heart rate, ST elevation, Sokolov index, number of premature ventricular complexes, number of premature atrial complexes (PAC), ratio of non-conducted P waves, and/or ratio of paced waves.

Delineator 39 may further deduce labels solely from the information generated by delineator 39. For example, the following labels may be deduced by delineator 39: short PR interval (i.e., PR interval <120 ms), first degree AV block (e.g., PR interval >200 ms), axis deviations, long QTc, short QTc, wide complex tachycardia, and/or intraventricular conduction blocks. Labels determined solely from information generated by delineator 39 are referred to as delineation based labels.

Referring again to FIG. 4, ECG platform 37 may cause the output of step 56 (e.g., wave information 62) as well as pre-processed ECG data 55 to be communicated or otherwise applied to clusterer 42 for clustering at step 63. Wave information 62 may include scores regarding PVC waves and PAC waves including onsets and offsets generated and relevant durations. Clusterer 42 may process wave information 62 and identify clusters of PAC or PAV waves during the duration of the cardiac signal. Once identified, clusterer 42 may assign cluster label 64 to one or more time windows, identifying either a PVC or a PAC cluster for each time window. A time window is defined by two time points in the cardiac signal.

Referring again to FIG. 4, ECG platform 37 may also cause the output of step 56 (e.g., wave information 57) as well as pre-processed ECG data 55 to be communicated or otherwise applied to classifier 41 for classification at step 58. Classification at step 58 involves applying a second neural network (i.e., classification neural network) to pre-processed ECG data 55. Accordingly, in one example, the input of the second neural network may be one or more multi-lead cardiac signals with variable length that is pre-processed. Classifier 41 may also process wave information 57 and/or other information such as patient-specific information including the patient's age or any relevant clinical information. As explained above, ECG platform 37 may cause optionally cause pre-processed ECG data 55 to be communicated directly to classifier 41 and processed by classifier 41 if delineation at step 56 is not necessary. In this manner, classifier 41 may process data sampled multiple times per heart beat across a plurality of heart beats.

The second neural network generates an output having values that correspond to the likelihood of the presence of one or more abnormality, condition and/or descriptor at each time point of the cardiac signal. If a time point or time window is determined to correspond to a certain abnormality, condition, and/or descriptor, a label corresponding to that abnormality, condition, and/or descriptor will be assigned to that time point or window. In one example, one or more labels 59 may be assigned to a time point or time window if a score achieves a predetermined threshold. Accordingly, multi-label localization may be achieved for abnormalities, conditions, and/or descriptors by generating a plurality of values at each time point and assigning one or more labels at each time point.

Classifier 41 may recover the output of the classification neural network as a vector of size q. The values in the vector correspond to the presence of each label at each time point or each time window. For example, the output of the classification neural network may be the vector [0.98: 0.89; 0.00] with the corresponding labels for each element of the vector: Right Bundle Branch Bloc; Atrial Fibrillation; Normal ECG. The scores may be between 0 and 1. For the vector above, a threshold of 0.5 would result in the labels "Right Bundle Branch Block" and "Atrial Fibrillation" being assigned by classifier 41 to the time point or time window corresponding to the score. It is understood that the threshold may be preprogrammed and/or selected by the user and may be modified to provide varying degrees of sensitivity and specificity. By assigning one or more labels for each time point, onsets and offsets corresponding to each label may be computed to identify durations of episodes (e.g., abnormalities episodes).

Abnormalities and conditions may include any physiological abnormality or condition which may be identifiable on the cardiac signal. Today about 150 measurable abnormalities may be identified on cardiac signal recordings. Abnormalities and conditions may include but are not limited to, sinoatrial block, paralysis or arrest, atrial fibrillation, atrial flutter, atrial tachycardia, junctional tachycardia, supraventricular tachycardia, sinus tachycardia, ventricular tachycardia, pacemaker, premature ventricular complex, premature atrial complex, first degree atrioventricular block (AVB), 2nd degree AVB Mobitz I, 2nd degree AVB Mobitz II, 3rd degree AVB, Wolff-Parkinson-White syndrome, left bundle branch block, right bundle branch block, intraventricular conduction delay, left ventricular hypertrophy, right ventricular hypertrophy, acute myocardial infarction, old myocardial infarction, ischemia, hyperkalemia, hypokalemia, brugada, and/or long QTc. Descriptors may include descriptive qualities of the cardiac signal such as "normal" or "noisy ECG."

Upon applying the second neural network at step 58, classifier 41 may read each time point of the cardiac signal as well as each global measurement, analyze each time point of the cardiac signal and each global measurement, compute time windows by aggregating at least two time points, and compute scores for each time window, the scores corresponding to a plurality of non-exclusive labels.

Figure 6A:
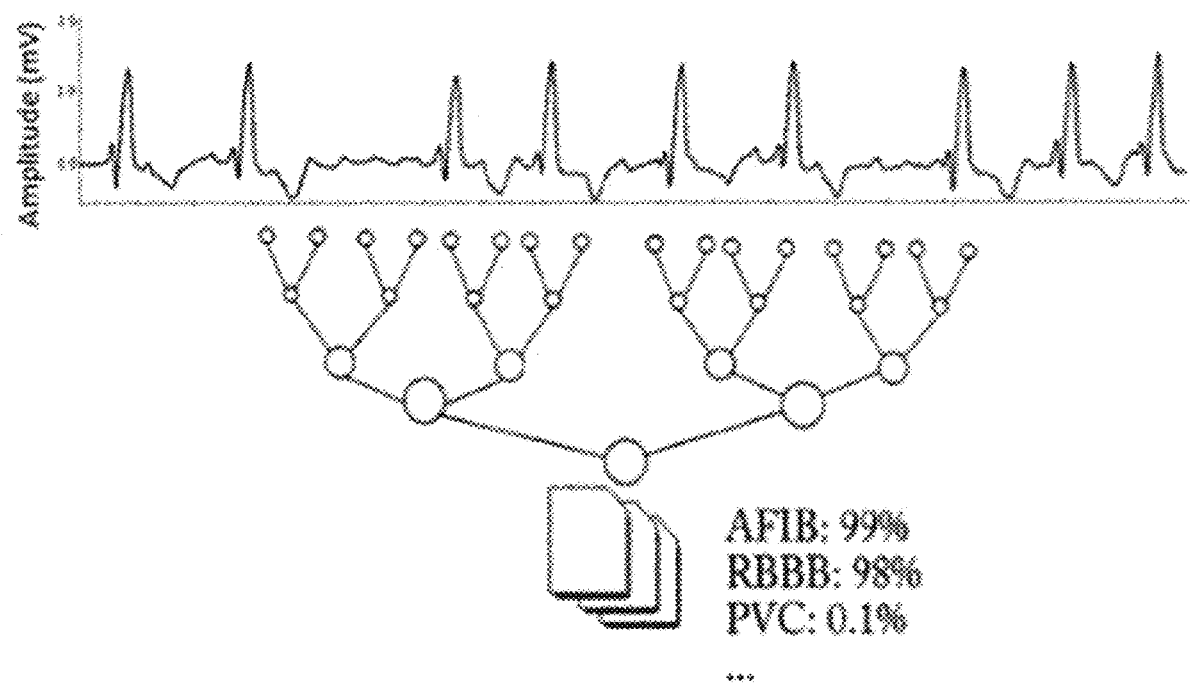
FIGS. 6A-6B are exemplary representations of classification neural networks in the form of a convolutional neural network and a recurrent neural network, respectively.

The classification neural network may be a convolutional neural network or a recurrent neural network. Referring now to FIG. 6A, a classification neural network in the form of a convolutional neural network is illustrated applied to an ECG signal. Most convolutional neural networks implement a few convolutional layers and then standard layers so as to provide a classification. The ECG signal is given as input to the network, which aggregates the information locally and then combines it layer by layer to produce a high-level multi-label classification of the ECG. For each label a score is provided. The labels of the convolutional neutral network shown in FIG. 6 include atrial fibrillation (AFIB), right bundle branch block (RBBB) and, and premature ventricular complex (PVC).

Figure 6B:
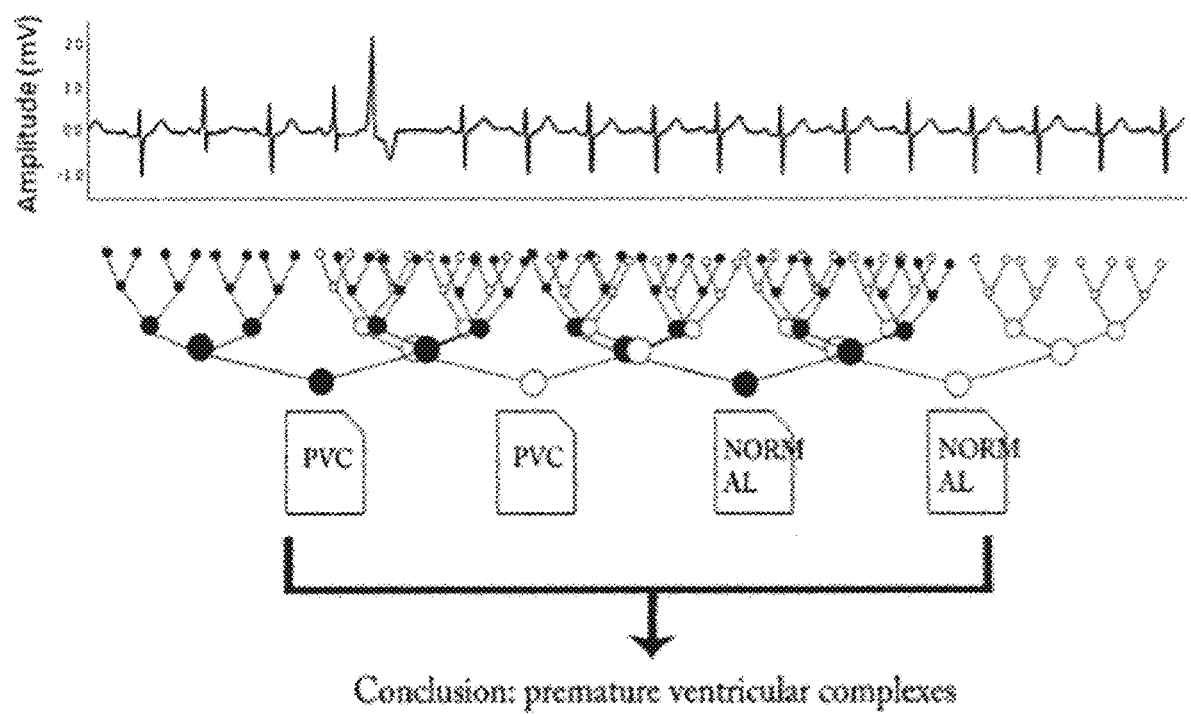

Referring now to FIG. 6B, a classification neural network in the form of a recurrent convolutional neural network is illustrated. Similar to FIG. 6A, the ECG signal is given as input to the network. A recurrent convolutional neural network refers to a particular convolutional neural network structure able to keep memory of the previous objects it has been applied to. A recurrent convolutional neural network is composed of two sub-networks: a convolutional neural network which extracts features and is computed at all time points of the cardiac signal, and a neural network on top of it which accumulates through time the outputs of the convolutional neural network in order to provide a refined output. In this manner, the convolutional neural network acts as a pattern detector whose output will be accumulated in time by the recurrent neural network.

As is shown in FIG. 6B, the output of the convolutional neural network identified four labels at various time points including premature ventricular complex (PVC) and Normal. Those labels were then applied to the second neural network which produced the refined output "premature ventricular complex." In this example, the network correctly recognized a premature ventricular complex (PVC, the fifth and largest beat) in the first part of the signal while the second part of the signal is considered normal. As the cardiac signal includes abnormality, it cannot therefore be considered as normal, and the accumulated output is therefore PVC.

The first neural network (i.e., delineation neural network) and the second neural network (i.e., classification neural network) must be trained to achieve the behavior and functionality described herein. In both the delineation and the classification embodiments, the networks may be expressed using open software such as, for example, Tensorflow, Theano, Caffe or Torch. These tools provide functions for computing the output(s) of the networks and for updating their parameters through gradient descent.

Training the neural networks involves applying numerous datasets containing cardiac signals and known outputs to the neural networks. A database of the datasets containing cardiac signals collected across a plurality of patients using the systems and methods described herein may be stored on server 15 and/or drive 16 (e.g., in the cloud). The datasets in the database may be used by server 15 to analyze new cardiac signals inputted into the system for processing. In a preferred embodiment, any cardiac signal applied to the trained neural network will have the same sampling rate and/or frequency as the cardiac signals in the datasets used to train the neural network. For example, training of the classification neural network begins with a dataset containing cardiac signals and their known delineation. As explained above, the cardiac signal is expressed as a matrix of size m×n at a predefined frequency. For example, the network may be trained at 250 Hz, 500 Hz or 1000 Hz, though any frequency could be used. The delineation is then expressed in the form of a Matrix Y of size p×n where p is the number of types of waves. Each wave is expressed with their start and end points such as, for example: (P, 1.2s, 1.3s), (QRS 1.4s 1.7s), (T, 1.7s, 2.1s), (P, 2.2s, 2.3s). In this example, the first row of Matrix Y corresponds to P-waves, and will have a value of 1 at times 1.2s and 1.3s, and as well as 2.2s and 2.4s, and 0 otherwise. The second row of Matrix Y corresponds to QRS complexes and will have a value of 1 at times 1.4s and 1.7s, and otherwise 0. Finally, the third row of Matrix Y corresponds to T-waves and will have a value of 1 at times 2.2s and 2.3s, and otherwise 0. The parameters of the network may then be modified so as to decrease a cost function comparing the known delineation and the output of the network. A cross-entropy error function is used so as to allow for multi-labeling (i.e., allowing for multiple waves at a given instant). This minimization can be done though a gradient step, repeating the foregoing steps at least once for each cardiac signal of the dataset. It is understood that a similar approach may be used to train the delineation neural network (i.e., second neural network).

Figure 7:
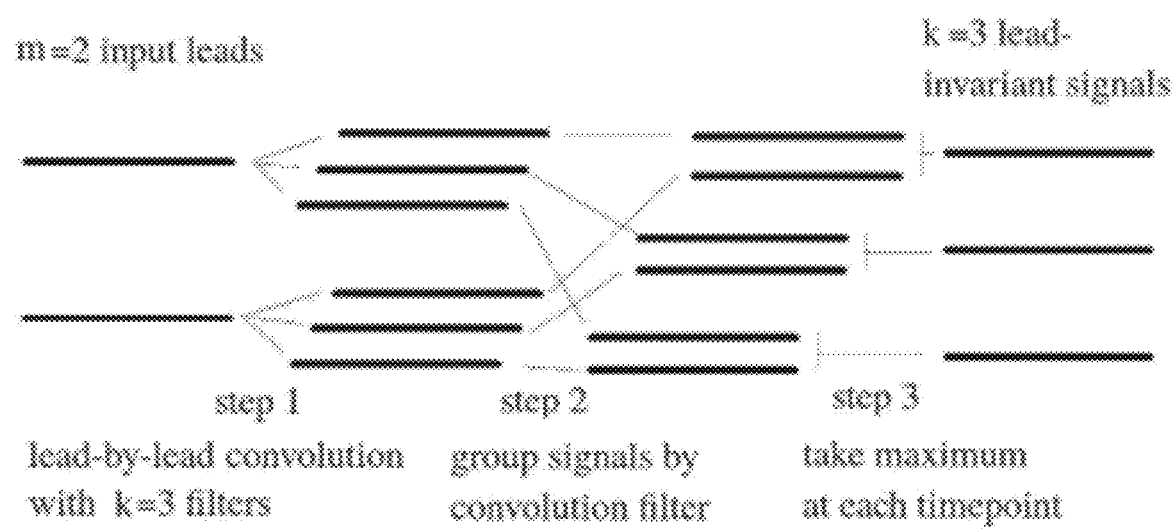
FIG. 7 is an exemplary representation of a variable number of lead entries and a constant number of outputs.

It is further understood that ECG platform 37 may cause neural networks described herein to process cardiac signals having a differing number of leads in entry. For example, the neural network may comprise a sequence of layers at the beginning of the network so as to obtain a network which is independent of the number of input leads and can therefore process cardiac signals with any number of leads m. For example, FIG. 7 illustrates two input leads (m=2) and three output signals (k=3). However, the same structure can process any number of input leads m and will still provide the same number of output signals, which can be fed to the rest of the network for which a fixed number of input signals is required. For this reason, the number of input leads may vary and need not be fixed.

As is shown in FIG. 7, to obtain k signals from an m input leads, the leads may be convoluted using a lead-by-lead convolution with k filters. The signal may then be grouped by a convolution filter in order to obtain k groups of m leads and a mathematical function is finally applied to each group to obtain k leads. The mathematical function may be the maximum at each time point or may be any other function known to one skilled in the art.

Referring again to FIG. 4, at step 61, ECG platform 37 may cause labels for each time window (i.e., labels) to be aggregated by post-processor 43 to generate processed labels 60. The labels may be derived from global measurements based on delineation. For example, the label corresponding to first degree atrioventricular block may be derived from a PR interval longer than 200*ms*. As explained above, the PR interval is a global measurement based on the delineation. Post-processor 43 may also aggregate the delineation-based labels with the classification labels corresponding to the same time points.

Post-processor 43 may also filter the labels to remove redundant labels, assemble labels according to a known hierarchy of labels, or ignore labels that are known to be of lesser importance according to a hierarchy or weighted values. Post-processor 43 may also aggregate the labels through time so as to compute the start (onset) and end (offset) times of each abnormality. It is understood that post-processor 43 may be a standalone component or may be a subcomponent of classifier 41.

As is shown in FIG. 4, the information generated on back end 46 by ECG platform 37 in steps 54, 56, 58 and 61, and optionally, 63, may be communicated by ECG platform 37 to ECG application 29 on front end 45. ECG application 29 may cause the foregoing information to be displayed, at step 65, on display 17 of system device 14. The information generated on back end 46 may be automatically transmitted by ECG platform 37 or ECG platform 37 may cause the information to be stored on server 15 until requested by ECG application 29. Upon generating the data, ECG platform 37 may transmit a message to ECG application 29, informing ECG application 29 that the data is available from ECG platform 37.

ECG application 29 may receive data (e.g., raw ECG data, pre-processed ECG data, wave information, labels and any other data generated during steps 54, 56, 58, 61, and/or 63) and cause system device 14 to display as described in PCT/EP2018/072912, the entire contents of which are incorporated herein by reference. Specifically, the '912 application explains that the ECG signal, features of the ECG signal, and/or descriptors of the ECG signal may be displayed in a multiple field display in an interactive manner.

Figure 8:
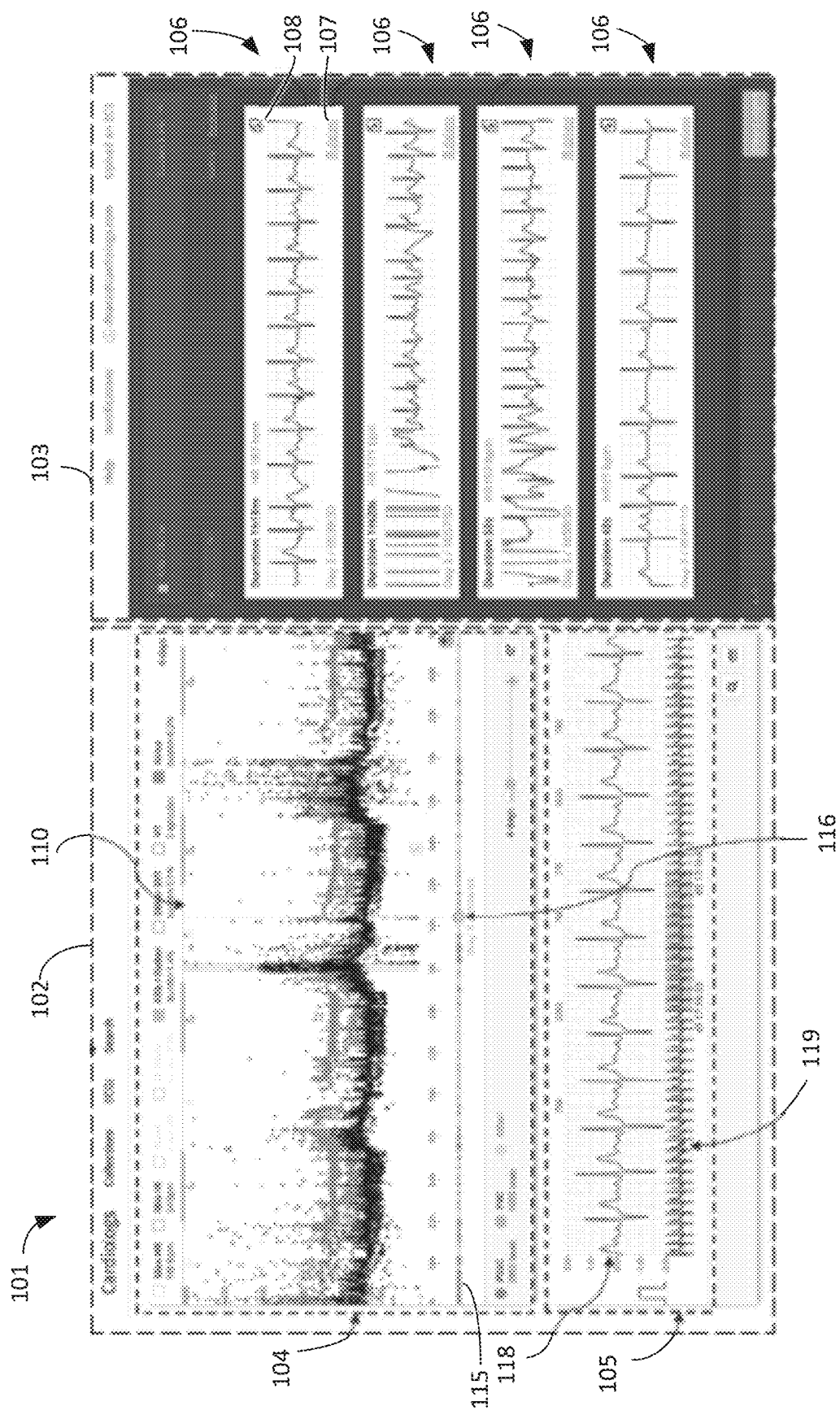
FIG. 8 is an exemplary user interface having an R-R plot generated in accordance with aspects of the recent disclosure.

Referring now to FIG. 8, an exemplary display, interactive display 101, is illustrated. Interactive display 101 includes first side 102 and second side 103. First side 102 further includes second graphic window 105 and first graphic window 104, having plot 110 which includes data corresponding to the ECG signal. First graphic window 104 includes plot 110 providing a global view of an ECG signal.

Figure 9:
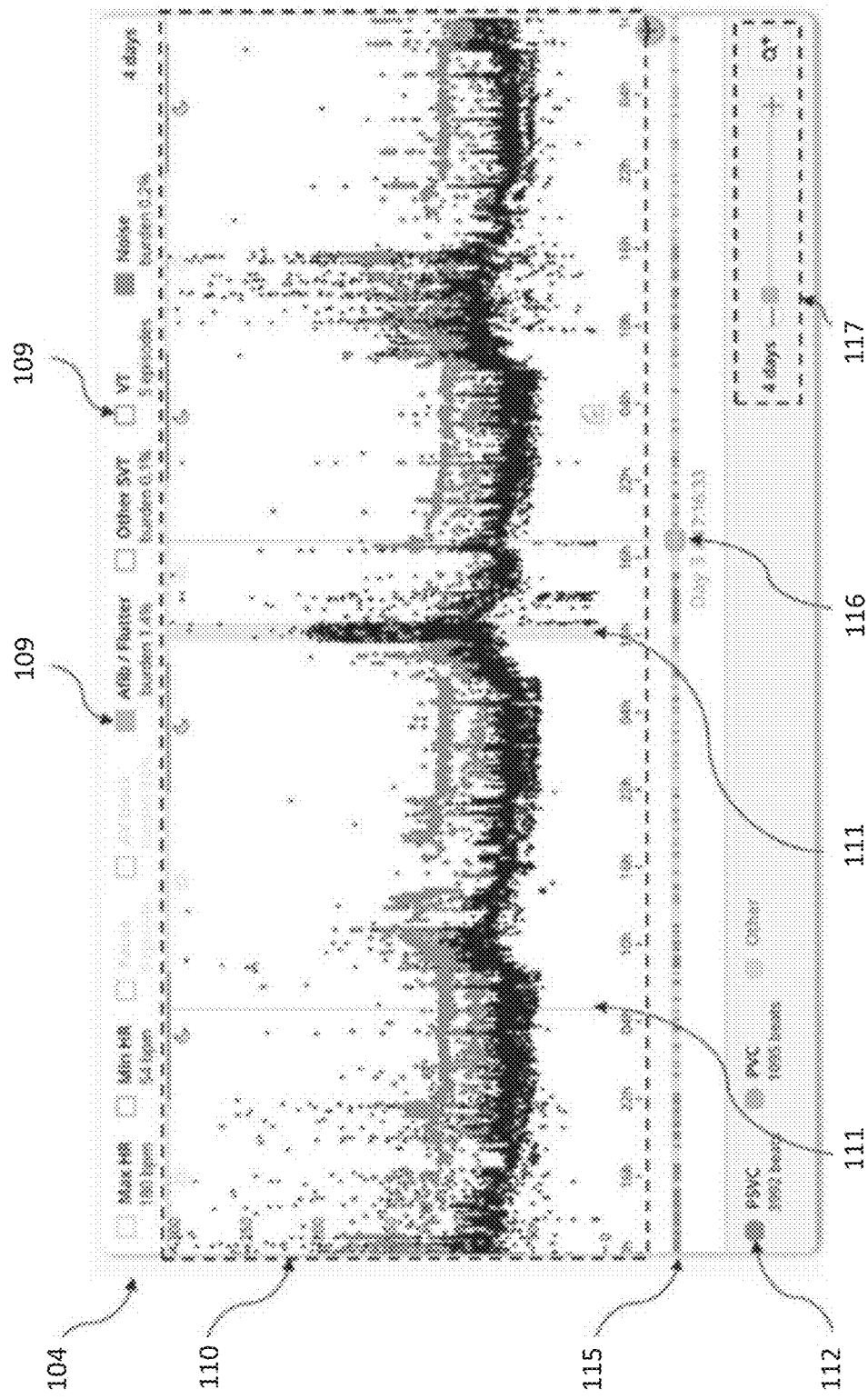
FIG. 9 is a zoomed-in view of the R-R plot shown in FIG. 8.

Referring now to FIG. 9, a zoomed-in version of first graphic window 104 is illustrated. In this exemplary display, plot 110 is an R-R interval plot which is a plot of R-R intervals (interval between two QRS waves) through time. As shown in FIG. 9, the upper region of first graphic window 104 comprises multiple label buttons 109. Each label button 109 has, displayed in its proximity, text describing the label to which it is associated. Each label button 109 is associated with a color so that, when label button 109 is selected by the user, graphic portion 111 is displayed on the plot 110 to visually indicate the presence the episodes and/or events corresponding to the label associate with label button 109. This provides visual references for the user permitting easy identification of a specific category of events and/or episodes along the cardiac signal. In the exemplary display illustrated in FIG. 9, secondary labels 112 are included. In this exemplary display, secondary labels 112 include beat label PVC (premature ventricular complex) and PSVC (premature supraventricular complex), though it is understood that other secondary labels may be included. The points in the plot 110 associated with the label PVC and PSVC are colored, as shown in FIG. 9 by the presence of points of color different from black.

First graphic window 104 further comprises, parallel to the time axis of the plot 110, temporal bar 115. Temporal bar 115 provides a linear representation of the total ECG acquisition time wherein the time periods associated to episodes or events are represented as colored segments. As is shown in FIG. 9, the darker grey zones on temporal bar 115 correspond to time periods of noisy signal (e.g., when the signal is too artifacted and the analysis algorithm cannot propose a delineation and proper detection). First graphic window 104 further comprises interactive cursor 116. A user using ECG application 29 may move interactive cursor 116 along temporal bar 115 to allow a navigation of the plot 110 along the total ECG acquisition time. In the right bottom corner of first graphic window 104, first graphic window 104 comprises second interactive means 117 configured to cause plot 110 to zoom in and out.

Referring again to FIG. 8, second side 103 includes multiple episode plots 106. Each episode plot 106 displays at least one segment of the ECG strip corresponding to a detected episode and may include text regarding the duration (e.g., "Duration: 1 h38 m") and/or the starting time of the episode (e.g., "Day 3/09:39:30"). Each episode plot 106 includes third interactive icon 108 to select the corresponding episode plot for inclusion in a report. Each episode plot 106 further includes fourth interactive icon 107 which permits the user to remove the respective ECG plot from interactive display 101. Second side 103 may further include text describing one or more of episode plots 106.

Interactive display 101 further includes graphic window 105 including ECG strip 118 in a second time window starting at the time point selected by the cursor 116. Second graphic window 105 further includes ECG strip 119 in a third time window which is larger than the second time window which is inclusive of the second time window. The third time window includes a shaded portion which corresponds to the second time window.

Figure 10:
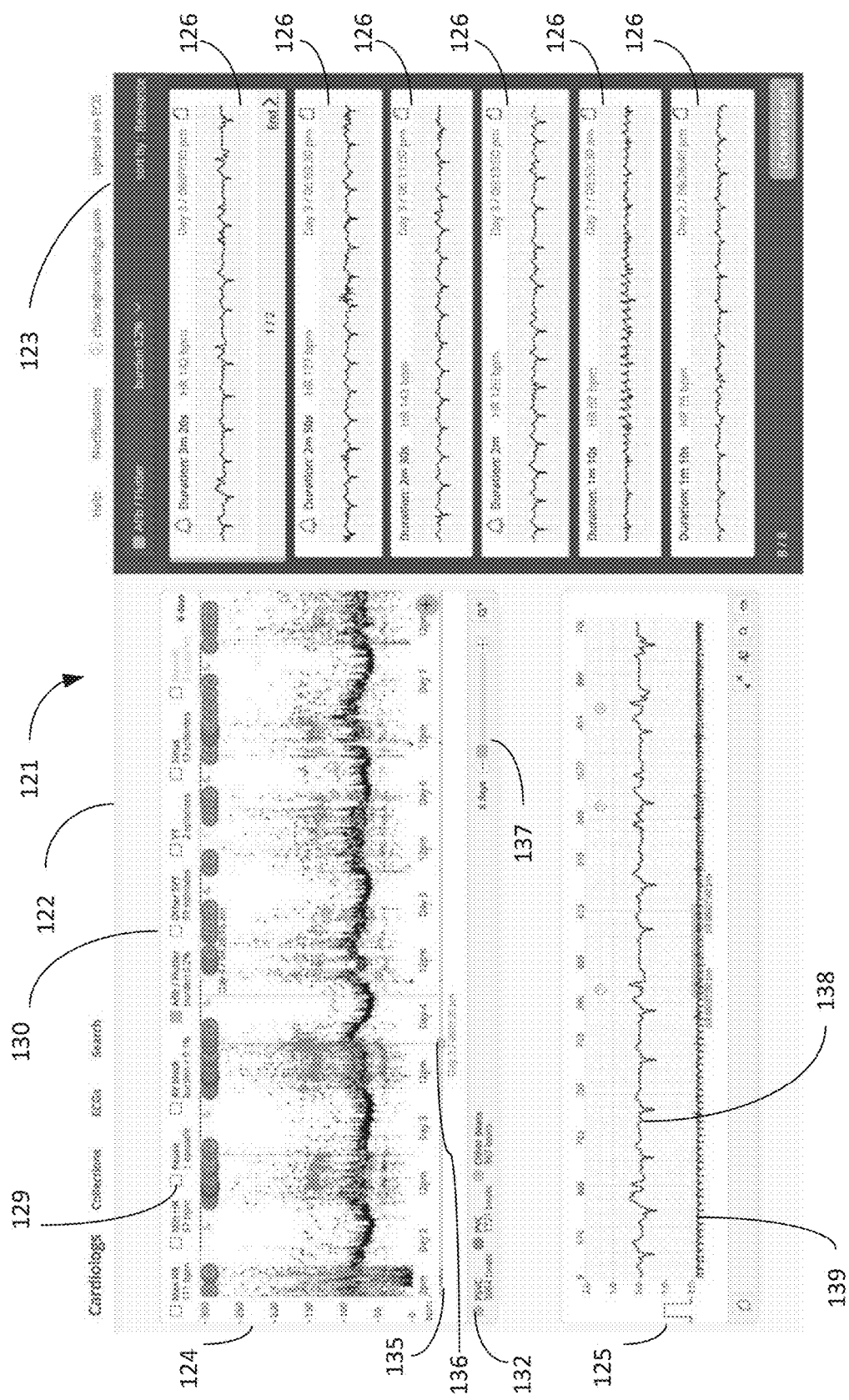
FIG. 10 is an exemplary user interface having a heart rate density plot generated in accordance with aspects of the present disclosure.

Referring now to FIG. 10, a similar display, interactive display 121, is illustrated. Interactive display 121 includes first side 122 and second side 123. First side 122 further includes first graphic window 124 and second graphic window 125. Second side 113 has the same functionality as second side 103 described above, and includes episode plots 126 similar to episode plots 106. Further, second graphic window 125 has the same functionality as second graphic window 105, and includes ECG strip 138 and ECG strip 139 similar to ECG strip 118 and ECG strip 119.

First graphic window 124 is similar to first graphic window 104 except for plot 130. Like first graphic window 104, first graphic window 124 includes multiple label buttons 129 having the same functionality as multiple label buttons 109, secondary labels 132 having the same functionality as secondary labels 112, temporal bar 135 and curser 136 having the same functionality as temporal bar 115 and cursor 116, and second interactive means 137 having the same functionality as second interactive means 117. Unlike plot 110, plot 130 is a heart rate density plot which is the projection onto a bivariate intensity plot of the histogram of the density of heart rates as a function of time.

Figure 11:
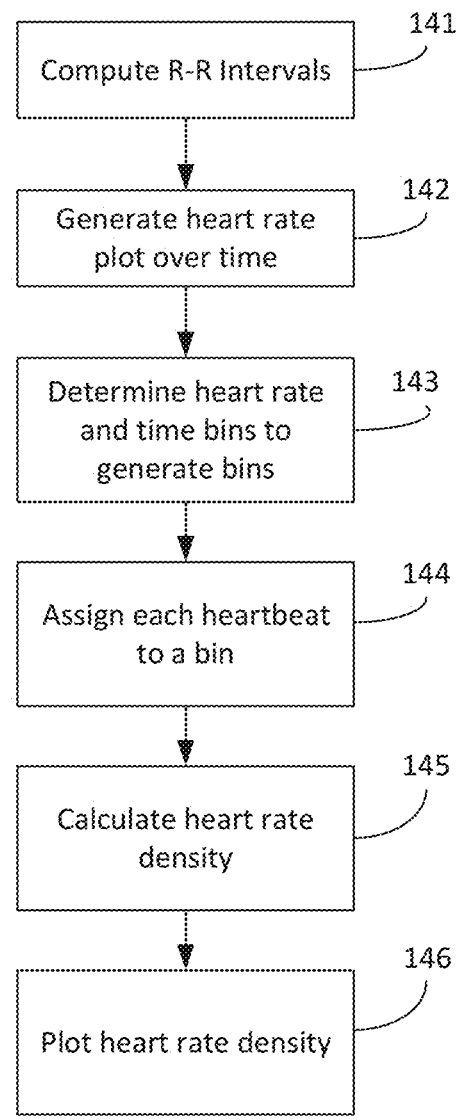
FIG. 11 is a flow chart illustrating an exemplary approach for generating a heart rate density plot.

Referring now to FIG. 11, steps for generating and plotting a heart rate density plot, such as plot 130, are provided. At step 141, ECG platform 37 computes R-R intervals in the cardiac signal (i.e., ECG data). For example, ECG platform 37 may apply the cardiac signal to the delineation neural network to determine the RR intervals, as described above. At step 142, ECG platform 37 may generate the heart rate plot over time. An exemplary heart rate plot, HRDP 150, is illustrated in FIG. 12.

Figure 12:
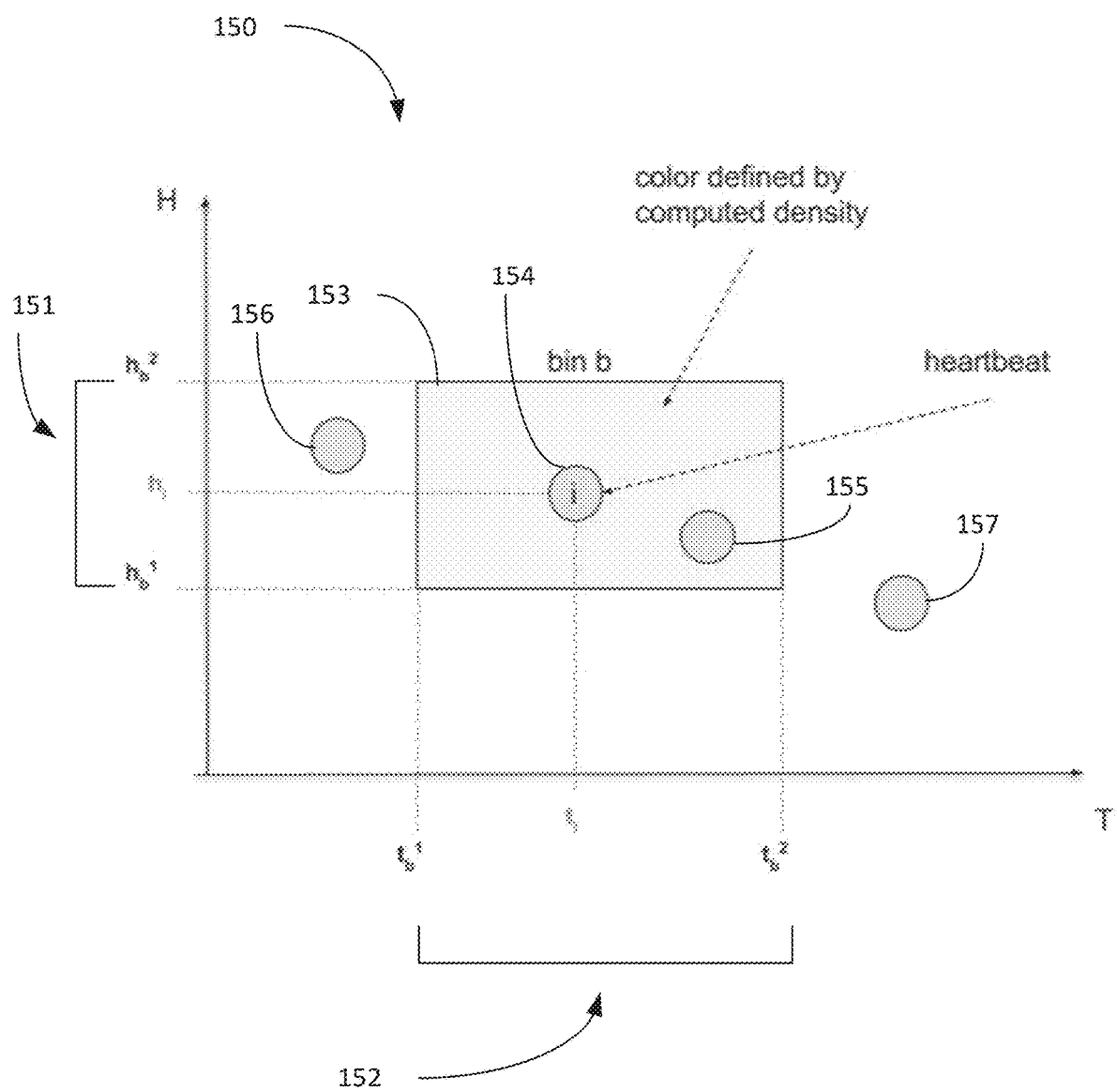
FIG. 12 is an exemplary heart rate density plot generated in accordance with aspects of the present disclosure.

As is shown in FIG. 12, time is projected along the x-axis and the heart rate (e.g., beats per minute) is projected along the y-axis. In one embodiment, both time and heart rate are scaled linearly. However, time and/or heart rate may be scaled logarithmically or using other well-known scales. For simplicity, only four heart beats are shown in FIG. 12.

Referring again to FIG. 11, at step 143, ECG platform 37 may cause the y-axis and the x-axis may be divided into elementary elements, referred to as HR bins and time bins respectively. For example, in FIG. 12, HR bin 151 and time bin 152 are illustrated. HR bin 151 is defined by a first and second heart rate value (e.g., $h_b^1$ and $h_b^2$). Similarly, time bin 152 is defined by a first and second time value (e.g., $t_b^1$ and $t_b^2$). The intersection of a HR bin and a time-bin will be referred to as a bin. In other words, a bin will be defined by a first and second heart rate value and a first and second time value. In FIG. 12, bin 153 is illustrated and defined by HR bin 151 and time bin 152.

Referring again to FIG. 11, at step 144, ECG platform 37 will cause each heartbeat to be assigned to a bin. Specifically, a heartbeat (e.g., QRS complex) that occurs during a time window of a given time bin is included in the computation of the column corresponding to that time bin. Further, a heart rate corresponding to that heartbeat determines which HR bin it belongs to in the column defined by the time bin. For example, in FIG. 12, heartbeat 154 and heartbeat 155 each have a corresponding time and heart rate value that fall within time bin 152 and HR bin 151, respectively. Conversely, heartbeat 156 and heartbeat 157 each have a time value that falls outside time bin 151 and thus neither are included in bin 153.

Referring again to FIG. 11, at step 145, ECG platform 47 will calculate the heart rate density for each time bin. For a given bin, the area defined by the respective time bin and heart rate bin will be represented according to the density of the heart beats comprised in the bin (i.e., number of heartbeats within the bin). Each bin may then be color coded according to the density. For example, each bin may have certain shades of colors or patterns, such as grey levels, for example. In the example in FIG. 12, bins may be represented as levels of grey that get darker as the density of heart rates increases. As is shown in FIG. 12, bin 153, which includes 2 heartbeats, may be represented by a darker shade of grey than a bin with only 1 heartbeat, but a lighter shade of grey than a bin having 3 or more heartbeats.

In a preferred embodiment, the density is calculated as a function of the number of R-waves in the bin divided by the heart rate of the HR bin (e.g. the mean of the minimum and maximum bounds of the time window). This preferred computation of density considers the time spent in a specific bin. For example, in a time bin of 3 minutes, if there occurs 100 beats at a heart rate of 50 bpm (beats per minute) in a first HR bin and 100 beats at 100 bpm in a second HR bin, there will be as many beats in each bin, but 2 minutes will be spent at 50 bpm and only one minute at 100 bpm. Therefore, this bin would have the same density representation if only the number of beats are considered. However, when considering the count of beats divided by the heart rate, the first bin corresponding to the heart rate bin of 50 bpm will be darker than the bin corresponding to the heart rate bin of 100 bpm, as dividing by the heart rate gives higher weight to lower heart rate values. The preferred embodiment therefore captures this temporal information better than only considering the count of beats.

Referring again to FIG. 11, at step 146, ECG platform 37 will plot the heart rate density for each bin. It is understood that capturing temporal information in the column (time bin), in addition to the temporal information naturally given as function of the x-axis, facilitates expression of the density in a manner superior to other forms of aggregated representations of the ECG signal, such as the R-R plot in plot 110.

Figure 13:
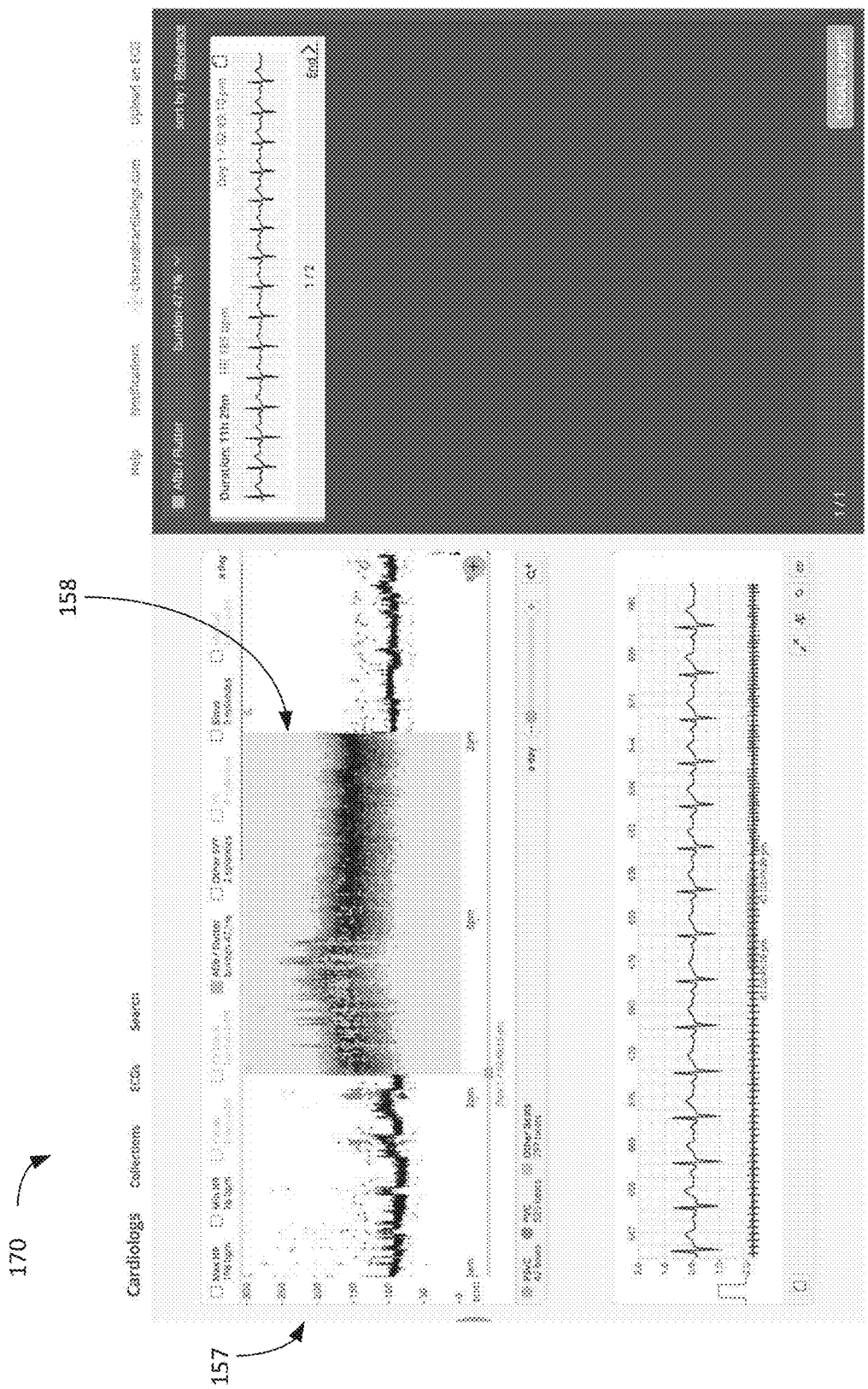
FIG. 13 is an exemplary user interface having a zoomed-in heart rate density plot.

It is understood that the bounds of the x-axis of the HR density plot may be the beginning and end of the signal. However, in a preferred embodiment, the bounds of the x-axis may interactively vary with the action of zooming in and out performed by the user. The bounds of the y-axis remain fixed when performing this action. Referring again to FIG. 10, plot 130 includes interactive means 137 which may be used to zoom-in on the heart rate density plot. The zoom action may only change the size of the plot display. Alternatively, zooming in and out changes the size of the time window corresponding to a time-bin. With the zooming-in action, a bin represented with the same number of pixels covers a shorter time window. Zooming in therefore causes a new computation of the histogram with finer temporal divisions, and consequently, finer temporal information. This allows for a representation of the ECG signal that shows varying levels of aggregation of the information as a function of the time scale one chooses to display, in order for the histogram to remain both readable and informative at any level of zoom. Referring now to FIG. 13, an interactive display, interactive display 170, is illustrated which is similar to the interactive display in FIG. 10. Interactive display 170 has been zoomed-in resulting in plot 159 having zoomed in portion 158.

Figure 14A:
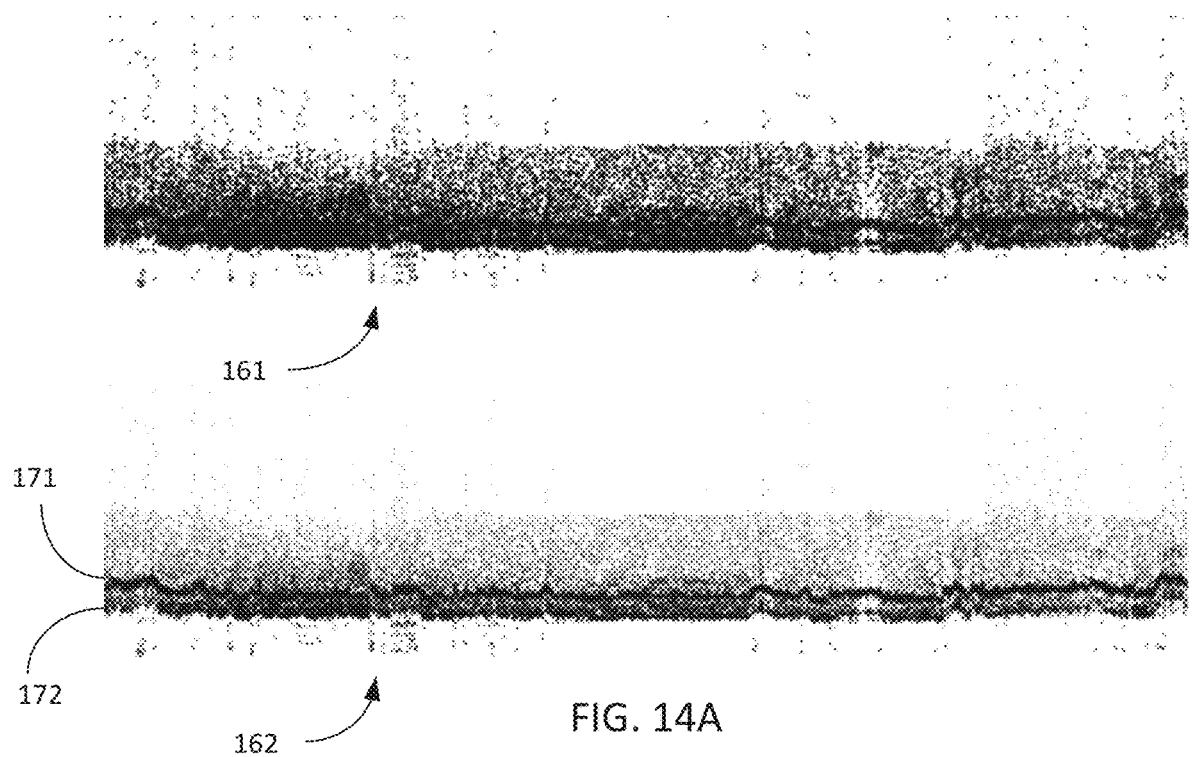
FIGS. 14A-14E are side-by-side comparisons of various R-R plots and heart rate density plots generated from the same cardiac signal.
Figure 14B:
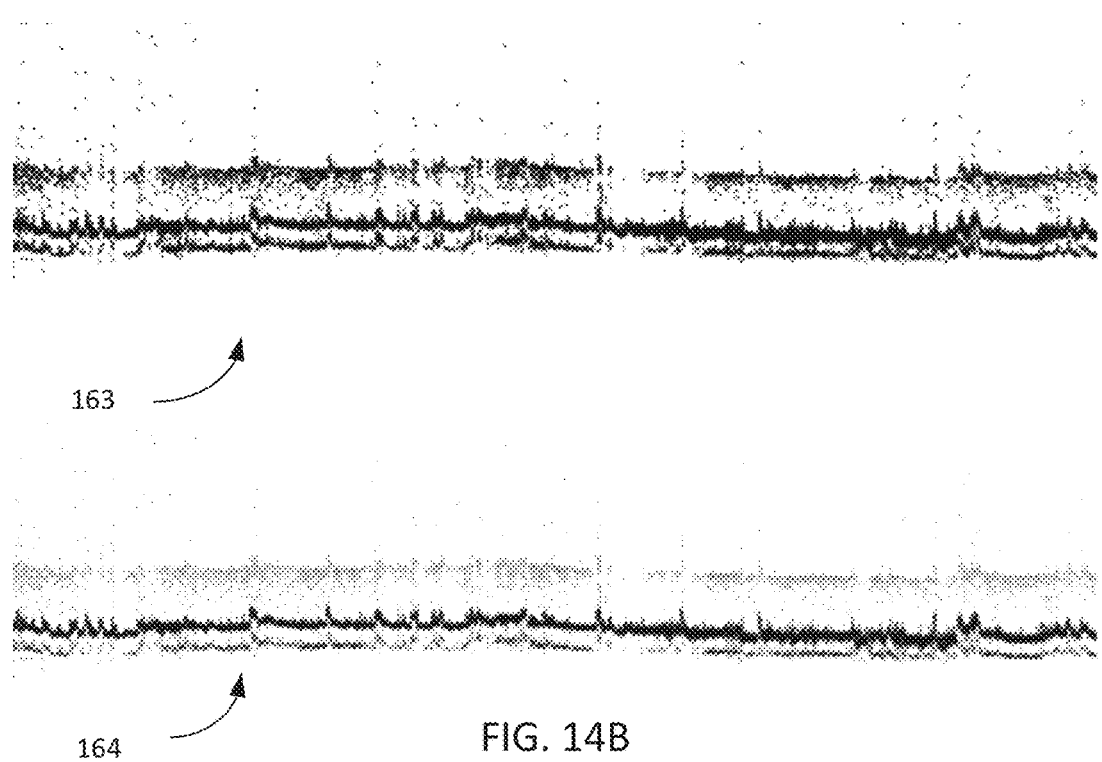
Figure 14C:
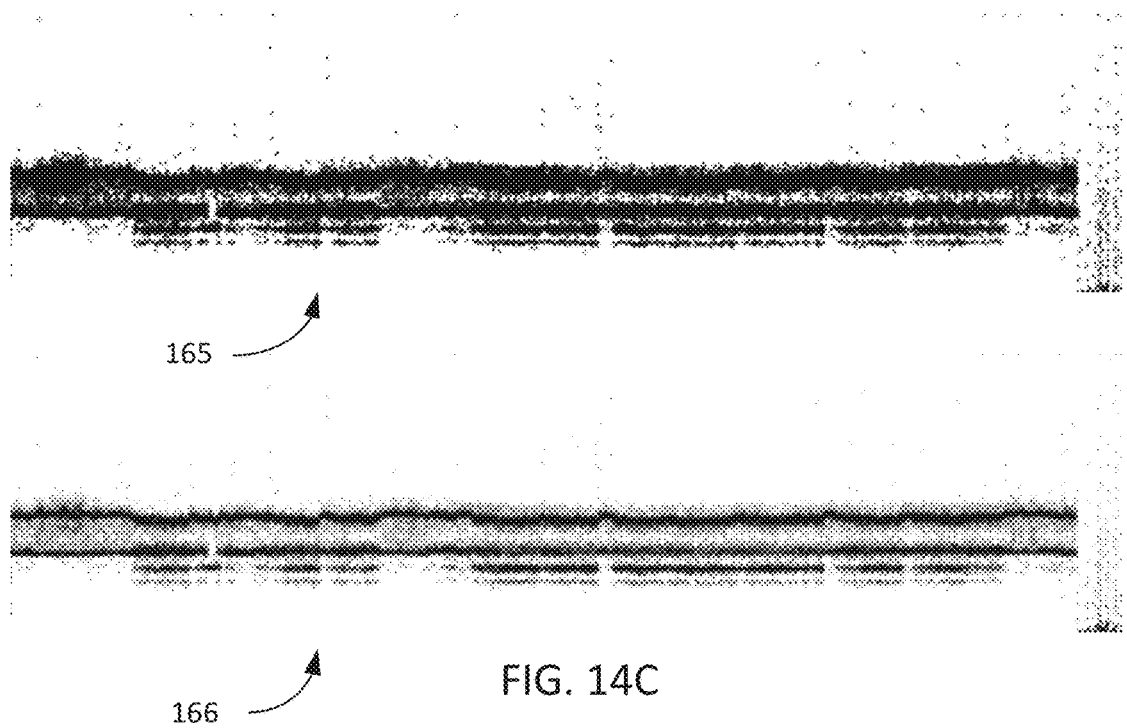
Figure 14D:
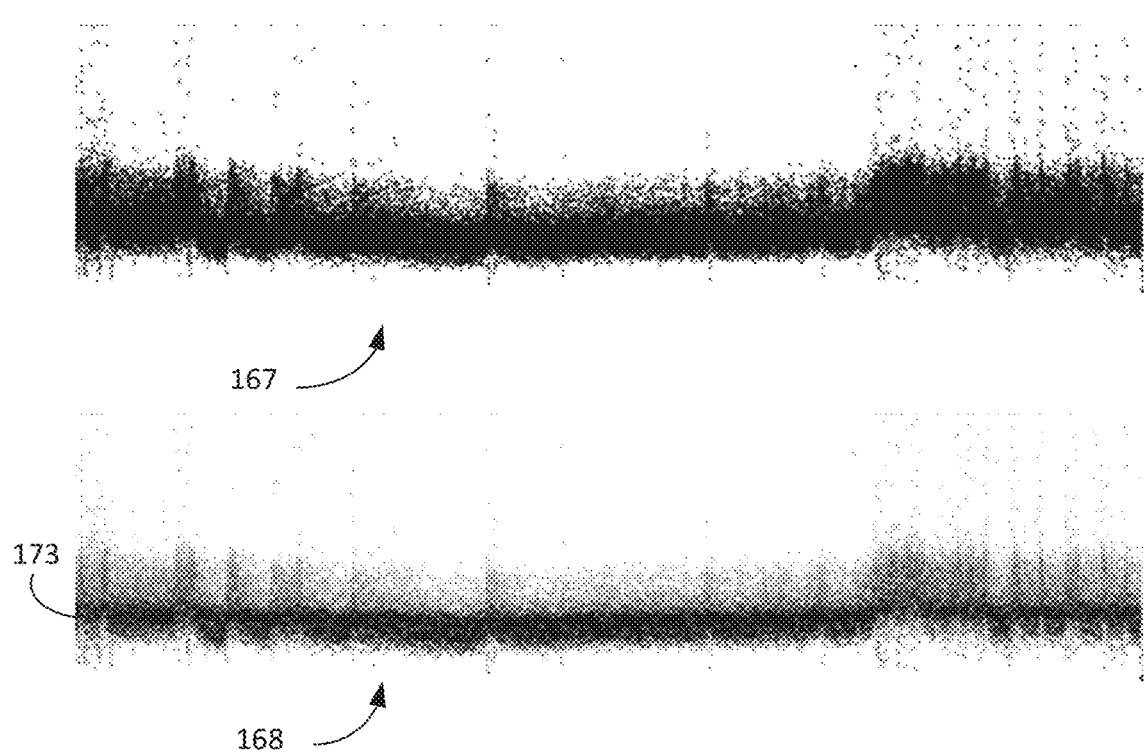
Figure 14E:
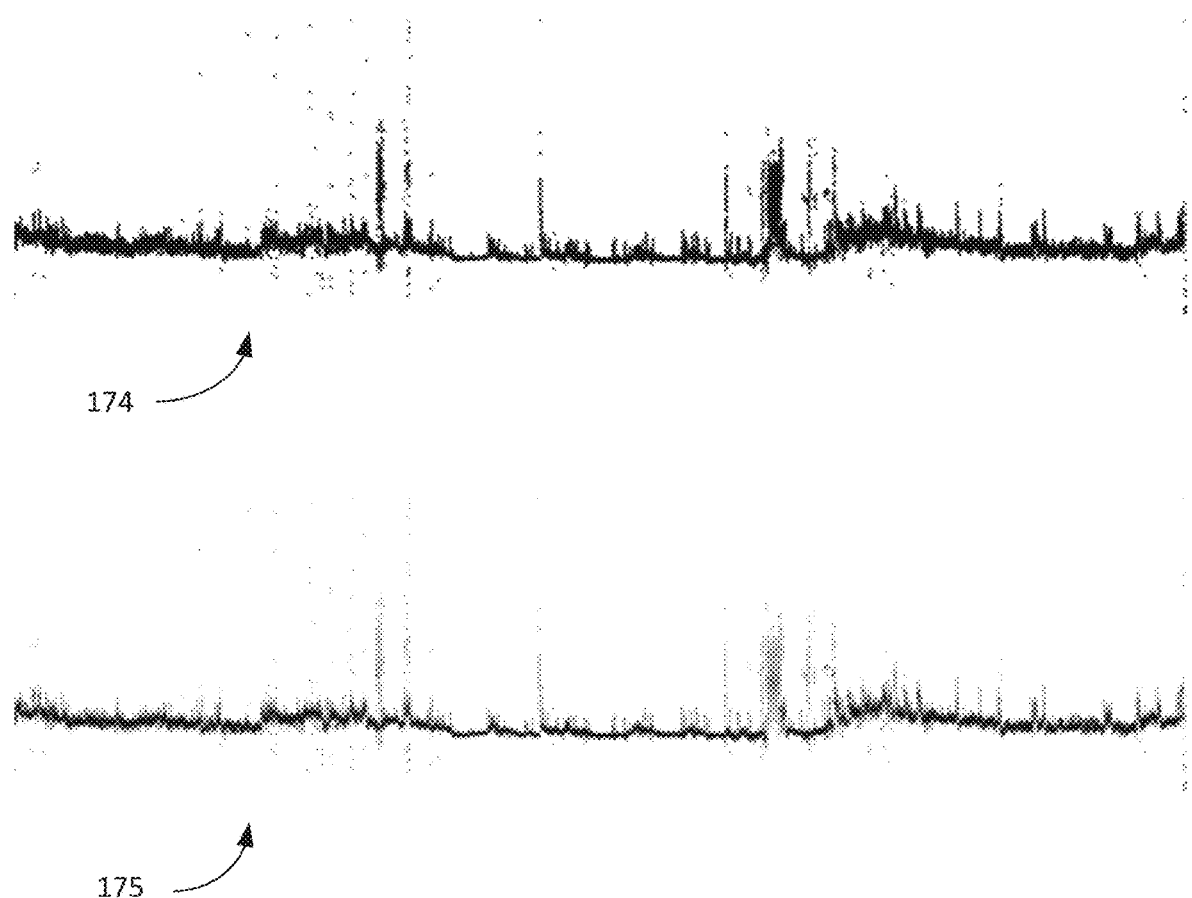

FIGS. 14A-E illustrate the superiority of the HRDP over the typical R-R plot. Referring now to FIG. 14A, a signal generated by a holter having a very high number of PVCs with varying coupling is illustrated as RR plot 161 and density plot 162. In density plot 162, the underlying rhythm is clearly visible as line 171. Further, the compensatory rest is illustrated as line 172 at the bottom. In R-R plot 161, this pattern is less clear. Referring now to FIG. 14B, a signal generated by a holter having less premature complexes than the one in FIG. 14A is illustrated as R-R plot 163 and density plot 164. The main rhythm is clearly illustrated in density plot 164 and is less clear in R-R plot 163. Referring now to FIG. 14C, a signal generated by a holter with vary conduction flutter is illustrated as R-R plot 165 and density plot 166. As is shown in FIG. 14C, the conduction flutter is more emphasized by the four clear black lines in density plot 166 than the four diffuse clouds that appear in the R-R plot 165. Referring now to FIG. 14D, a signal generated by a holter with permanent atrial fibrillation is illustrated as R-R plot 167 and density plot 168. As is shown in this figure, density plot 168 gives more precise information on the variations of the heart rate within the fibrillation. Specifically, darker lower half 173 shows that more time is spent at a low heart rate than at a high heat rate. Density plot 168 further illustrates spikes where the upper half becomes a bit darker corresponding to the heart rate increasing. These nuances are not visible in R-R plot 167. Referring now to FIG. 14E, a signal generated by a holter having paroxysmal atrial fibrillation and otherwise regular rhythm is illustrated as R-R plot 174 and density plot 175. The pattern of a regular rhythm is more visible in density plot 175 where a clear black line emerges. Also, the pattern of atrial fibrillation contrasts more in density plot 175 than R-R plot 174 as the color changes as well (density diminishes which makes the plot lighter).

Referring again to FIG. 4, at step 66, a user using ECG application 29 may interact with an interactive active display described above using input devices 25 to request a report and/or customize the report. A report typically includes portions of the cardiac signal and may involve information pertaining to abnormalities and/or episodes (e.g., episode plots) and/or other information generated during pre-processing (step 54), delineation (step 56), classification (step 58), clustering (step 63) and/or post-processing (step 61). A report may further include patient specific medical data such as the patient's name, age, health history, and/or other medical information. It is understood that any individually identifiable health information, and/or protected health information may be encrypted when communicated between ECG application 29 and ECG platform 37.

As explained above, interactive icons in interactive displays may be engaged to incorporate data and images displayed in a report. For example, third interactive icon 108 may be selected by a user using ECG application 29 to include the corresponding episode plot in a report. Accordingly, at step 66, the user may request a report and may select customized features such as certain data to be included in the report (e.g., abnormality data, episode data, episode plots, etc.).

At step 67, ECG application 29 may transmit the request for a report and selected customizable features (e.g., ECG data to be included in the report) to ECG platform 37 and ECG platform 37 may receive the request and information. ECG platform 37 may log the request and save the information received from ECG application 29. At step 68, ECG platform 37 may cause report generator 44 to generate a report according to the information received from system ECG application 29.

Figure 15B:
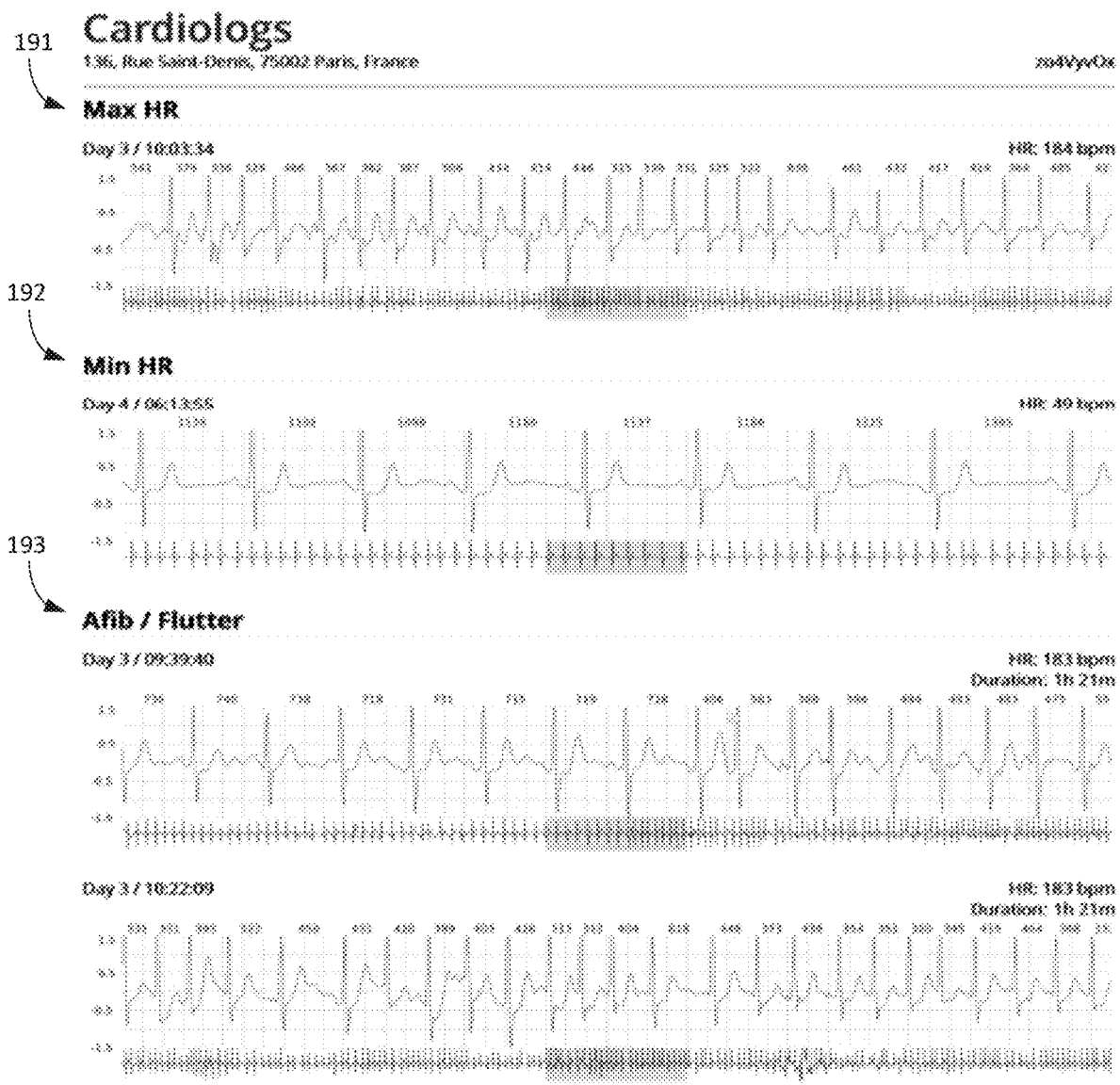

Referring now to FIGS. 15A-15D, an exemplary report generated at step 68 is illustrated. The first page of the exemplary report is illustrated in FIG. 15A. The first page may be presented in several sections such as first section 181, second section 182, third section 183, fourth section 184, fifth section 185, and sixth section 186. First section 181 may include patient specific information such as, for example, the patient's name, primary indication, whether the patient has a pace maker, the patients date of birth, gender and/or a patient ID. Second section 182 may include clinician information such as, for example, the overseeing physician, the name of the institute, the date of the analysis and/or a signature.

Third section 183 may include a plot of the ECG data. In FIG. 15A, section 183 includes a heart rate density plot similar to the one shown in FIG. 12. The window of time shown may be a default time or may be a user defined time window. Like the heart rate density plot in FIG. 12, a certain label may be selected to indicate the occurrence of an abnormality on the density plot. The time window is usually selected according to the relevant episodes and/or events. It is understood, however, that other plots may be included in the report such as an R-R plot.

Fourth section 184 may include metrics from the cardiac signal recording. For example, fourth section 184 may include the duration of the recording, the maximum, minimum and average heart rate, premature supraventricular complexes and any patient-triggered events, and/or any other metrics concerning the cardiac signal. Fifth section 185 may include information corresponding to any episodes detected. For example, fifth section 185 may include pause information (count and/or longest R-R interval), atrioventricular block information, atrial fibrillation/flutter information, ventricular tachycardia information, other supraventricular tachycardia information, and/or any other information concerning any episodes or abnormalities. Sixth section 186 may include results information such as, for example, a summary of the episodes and/or abnormalities, a diagnosis, and/or any other information analyzed, aggregated, computed, determined, identified, or otherwise detected from the cardiac signal. For example, sixth section 186 may identify a sinus rhythm with paroxysmal atrial fibrillation.

Figure 15C:
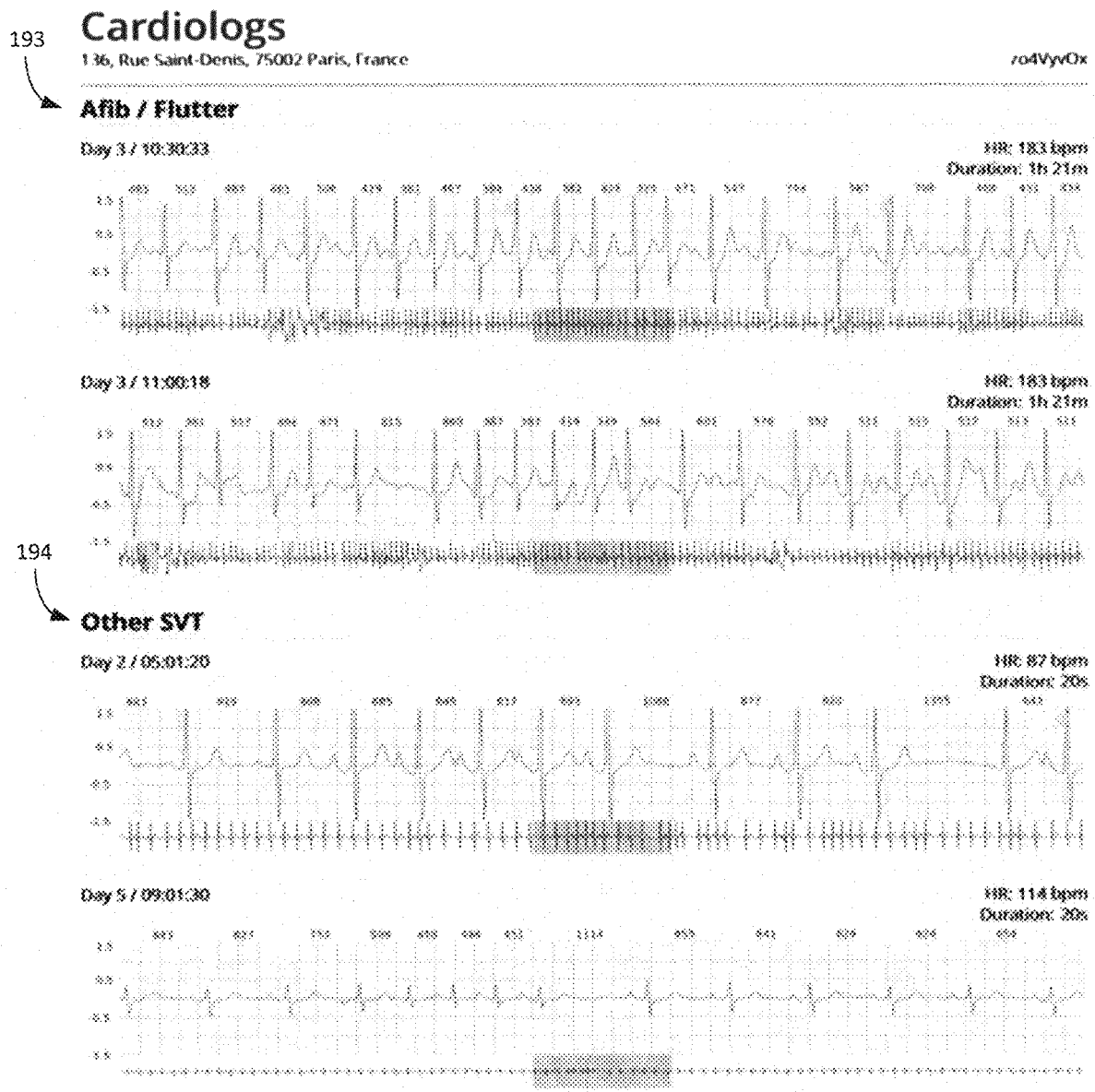
Figure 15D:
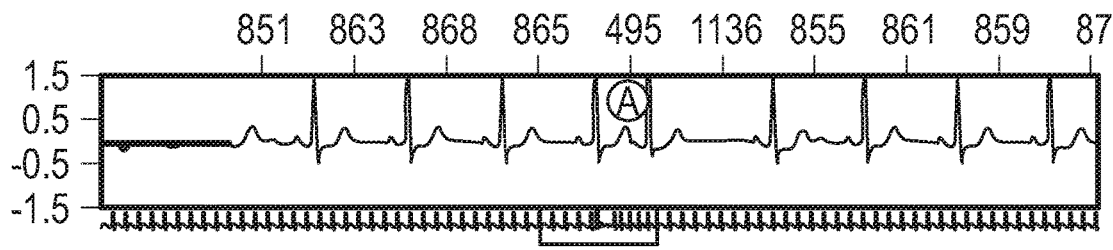
Figure 15D:
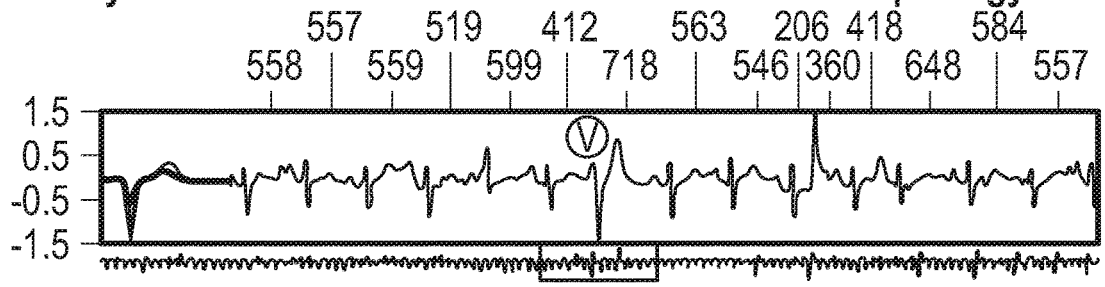
Figure 15D:
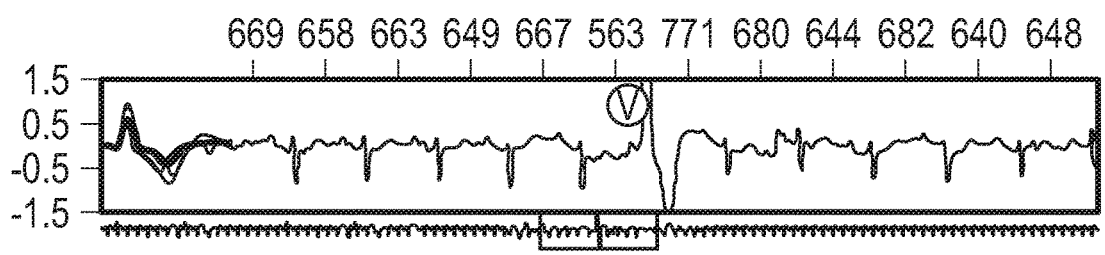

FIG. 15B-D illustrates the second, third and fourth pages of an exemplary report. As is shown in FIG. 15B-D, the report may further include ECG strips previously selected by the user, or selected under default settings. For example, a user may select Max HR strip 191, Min HR strip 192, Afib/Flutter strips 193, other SVT strips 194, PSVC strip 195, and PVC strip 196. Max HR strip 191 may be an ECG strip indicating the maximum heart rate during a given cardiac signal recording. Similarly, Min HR strip 191 may be an ECG strip indicating the minimum heart rate during a given cardiac signal recording. Afib/Flutter strips 193 may be ECG strips indicating each episode of atrial fibrillation/ flutter. Other SVT strip 194 may be ECG strips indicating each episode of supraventricular tachycardia. PSVC strip 195 may be an ECG strip indicating an episode of premature supraventricular complex. PVC strip 197 may be ECG strips indicating episodes of premature ventricular complex. ECG strips may be displayed with the related relevant associated metrics and comments as added by the user. It is understood that the report shown in FIGS. 15A-B is merely exemplary and that the report generated at step 68 may have a different structure or configuration and/or may include different ECG and patient related information contemplated herein.

Figure 16A:
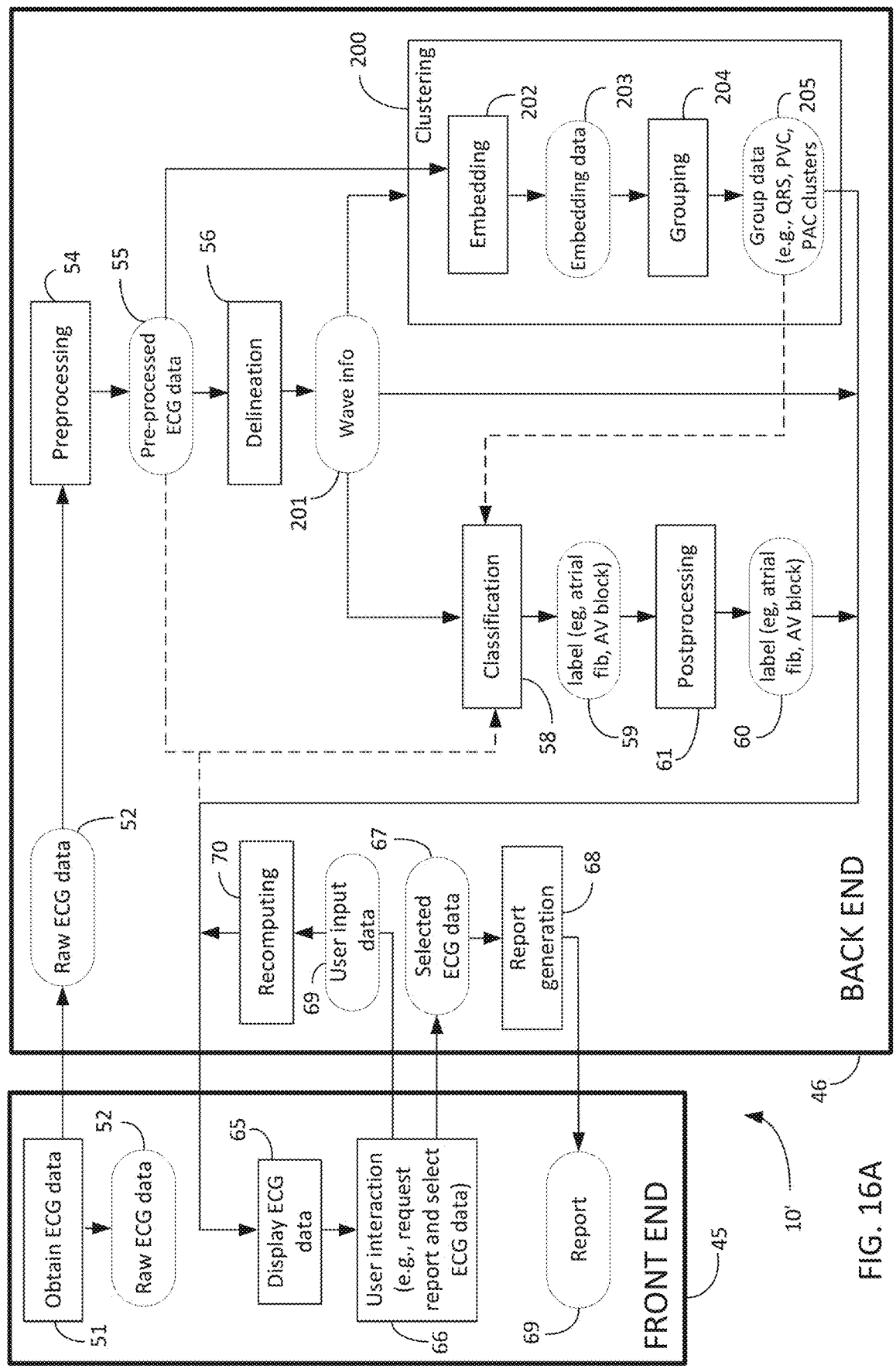
FIG. 16A is a flow chart of an exemplary method of processing ECG data, displaying ECG data, and generating a report including ECG data

Referring now to FIG. 16A, ECG processing system 10' is illustrated which is substantially similar to ECG processing system 10 but includes steps 202-205. Like ECG processing system 10, ECG processing system 10' may receive raw ECG data 52 at back end 46 to be preprocessed at step 54 by pre-processor 38 to generate pre-processed ECG data 55 which may be applied to delineator 39 for delineation at step 56 to generate wave information 201. Wave information 201 may include wave information 57 (e.g., scores corresponding to the likelihood of the presence of a t-wave, p-wave, QRS complex, etc.) and/or wave information 62 (e.g., scores regarding PVC waves and PAC waves, etc.). As explained above, the output of delineator 39 may be one or more vectors and/or a matrix.

Wave information 201 may further include information about onsets and offsets of one or more wave and/or beat in the ECG data. For example, based on the likelihood of the presence of certain types of waves at time points throughout the ECG data, delineator 39 may determine the onset and offset of one or more waves and/or beats. At step 200, clusterer 42 may use the onsets and offsets of beats in wave information 201 to extract the beats from the ECG data (e.g., pre-processed ECG data). This may involve determining portions of the ECG data starting at an onset of a beat and ending at an offset. These portions may be extracted from the ECG data and designated as a beat. The portions of ECG data corresponding to a beat may be used an input at step 202.

Also at step 200, clusterer 42 may include, oversee, and/or implement embedder 48 and grouper 49. Specifically, step 200 may include sub-step 202 and sub-step 204 clusterer 42 may execute one or more algorithms, which may be one or more trained neural networks, to generate embedding data 203 and ultimately group data 205. Specifically, at sub-step 202, embedder 48 may execute one or more algorithms, which may be a trained neural network, to generate embedding data 203. The portions of ECG data extracted at step 200 may be input to embedder 48. Embedding data 203 may be one or more vectors that represent the beat portions of ECG data used as an input for embedder 48. In this manner beats identified in the ECG data may be extracted from the ECG data and embedded using embedder 48. In one example, embedding data 203 may be one or more vectors and/or a matrix corresponding to, and representative of, one or more beats. At sub-step 204, grouper 49 may execute one or more grouping algorithms, which may be a trained neural network, on the embedded data 203 to generate group data 205.

Figure 16B:
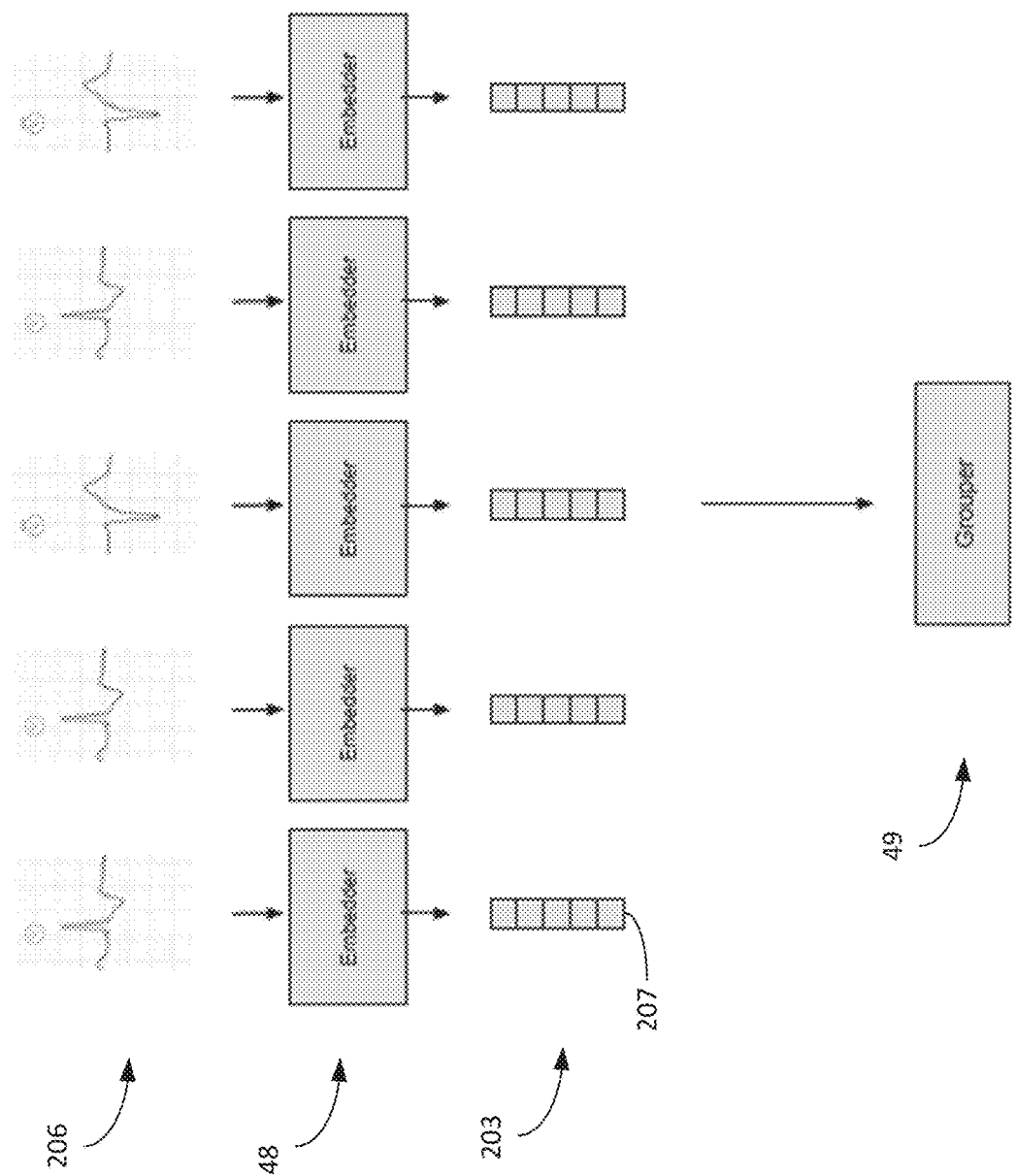
FIG. 16B is an exemplary data flow illustrating embedding.

The process of extracting portions of ECG data, inputting the portions of ECG data into embedder 48, generating embedding data 203, and inputting embedding data 203 into grouper 49 is illustrated in greater detail in FIG. 16B. As shown in FIG. 16B, portions of ECG data 206 may be used an input for embedder 48 for embedding. The portions of ECG data 206 may be a portion of ECG data (e.g. pre-processed ECG data) over a time period starting at an onset of a beat and ending at an offset of a beat. For example, embedder 48 may process portions of ECG data 206 using one or more algorithms, resulting in embedding data 203. The one or more algorithms may be one or more neural networks (e.g., embedding neural networks). Embedding data 203 may be one or more beat vectors 207. Beat vectors 207 may be a vector including data and/or values representative of portions of ECG data 206. As shown in FIG. 16B, beat vectors 207 may be input into grouper 49 for grouping.

Referring again to FIG. 16A, Grouper 49 may process the embedding data 203 corresponding to beats using one or more algorithms, resulting in group data 205 corresponding to a similarity between two or more beats. The one or more algorithms may be one or more neural networks (e.g., grouping neural networks). Group data 205 may include one or more scores or values corresponding to a similarity and/or distance between vectors of embedding data 203. A similarity may involve similar characteristics and/or features such as similar t-waves, p-waves, QRS complexes, or other waves, or a similar distance between any of the forgoing, for example. In this manner, grouper 49 may quantify a similarity between two or more beats of ECG data. Based on group data 205, clusterer 49 may determine if group data 205 (e.g., scores or values) is within a threshold differential or satisfies a threshold value and thus if the corresponding beats are similar enough to one another (e.g., have similar characteristics and/or features) such they should be grouped or matched together. Groups of similar beats may be referred to herein as a morphology and/or cluster. As is shown in FIG. 16A, group data 205 may optionally be applied to classifier 41 for classification at step 58.

As is shown in FIGS. 3A, 3B, and 16, group data 205 and/or a graphic user interface based on or otherwise incorporating group data 205 may be communicated by ECG platform 37 on back end 46 to ECG application 29 on front end 45. ECG application 29 may cause information about beat groupings and/or group data 205 to be displayed at step 65 on display 17 of system device 14. For example, information regarding beats associated with a type of episode (e.g., QRS clusters, PVC clusters, and/or PAC clusters) may be displayed on display 17. The information generated on back end 46 may be automatically transmitted by ECG platform 37 or ECG platform 37 may cause the information to be stored on server 15 until requested by ECG application 29. Upon generating the data, ECG platform 37 may transmit a message to ECG application 29, informing ECG application 29 that the data is available from ECG platform 37. ECG application 29 may receive data (e.g., raw ECG data, pre-processed ECG data, wave information, labels, clusters, and/or morphologies and any other data generated during steps 54, 56, 58, 61, 63, and 200, including sub-steps 202 and/or 204) and cause system device 14 to display the information and/or data as described herein as well as in WO 2019/038435, the entire contents of which are incorporated herein by reference.

A user using ECG application 29 may view wave information, labels, episodes, clusters, beat groupings and/or morphologies and any other data generated during steps 54, 56, 58, 61, and 200 on display 17. At step 66, a user using ECG application 29 may interact with an interactive display described above using input devices 25 to generate user input data 69, which may be communicated from ECG application 29 on front end 45 to ECG platform 37 on back end 46. For example, a user may view QRS clusters, PVC clusters and/or PAC clusters on display 17. Using input device 25, a user may interact with display 17 to generate user input data 69 relevant to wave information, labels, episodes, clusters, beat groupings and/or morphologies and any other data presented on display 17. For example, a user may determine or identify additional clusters and/or beat groups, may identify, associate, and/or merge similar clusters and/or beat groups, may delete clusters and/or beat groups that are inaccurate, irrelevant, or mislabeled, and/or may split clusters and/or beat groups into different subsets. Additionally, user input data 69 may correspond to deleted and/or modified morphologies as described below.

Upon receiving user input 69, ECG platform 37 on back end 46 may, at step 70, cause recomputer 40 to use user input data 69 to retrain, modify and/or adjust delineator 39, embedder 48 and/or grouper 49. For example, user input data 69 may indicate that grouping data 205 was inaccurate. Recomputer 40 may use this information to retrain and/or adjust delineator 39, embedder 48 and/or grouper 49 to generate more accurate grouping data 205. Upon retraining delineator 39, embedder 48 and/or grouper 49, one or more of step 200, sub-step 202 and/or sub-step 204 may be repeated and the information generated (e.g., group data 205, episodes, and/or clusters or morphologies) may be sent to ECG application 29 on front end 45, as explained above, to be displayed on display 17 and viewed by the user. By recomputing the group data, episodes, and/or clusters or morphologies and presenting the same to a user via display 17, a user may adjust and otherwise fine tune processing system 10'. For example, more accurate episodes may be identified and the quality of wave information 201, embedding data 203 and/or group data 205 may be improved.

Figure 17:
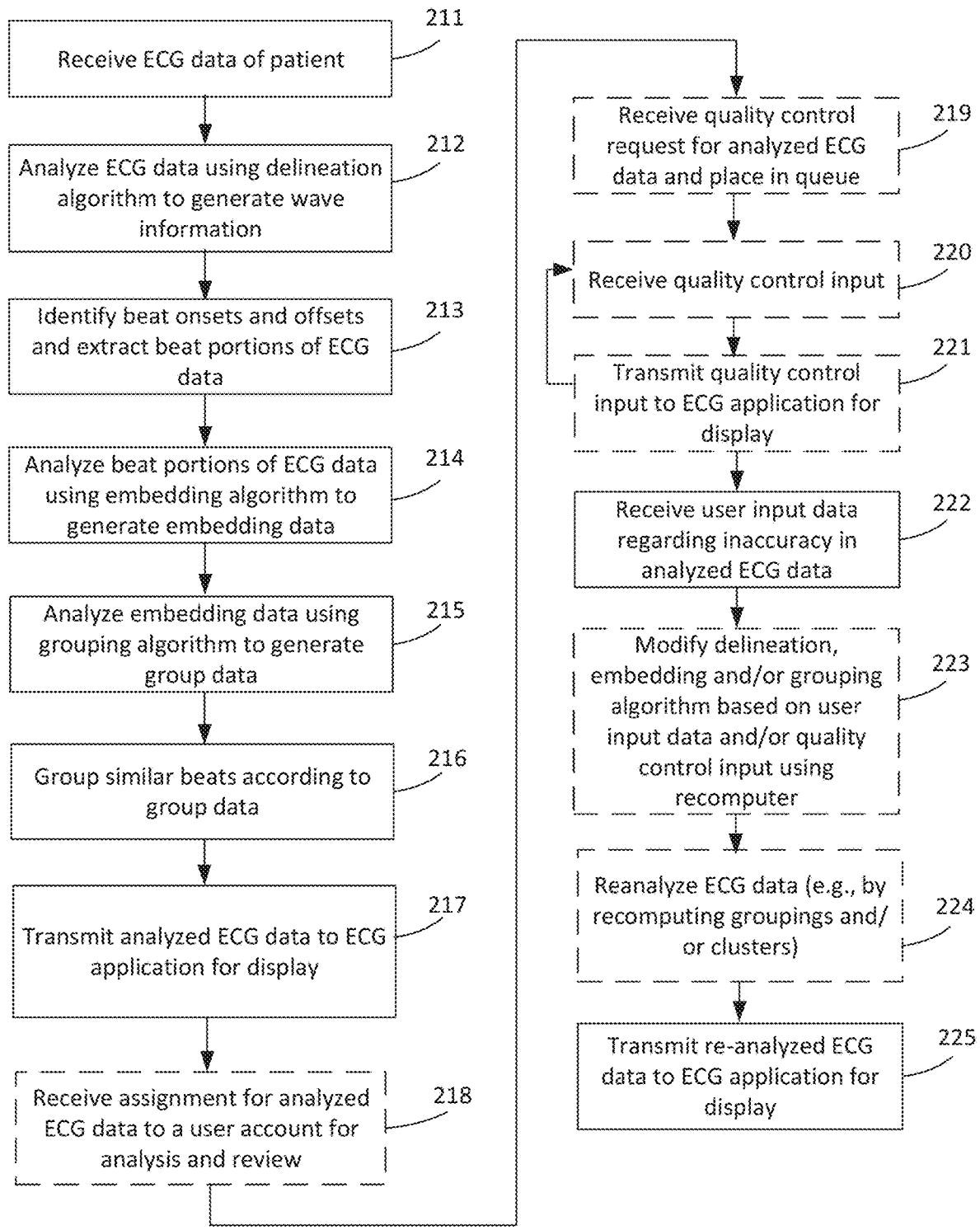
FIG. 17 is an exemplary process for analyzing ECG data and grouping similar beats using a grouping algorithm.

Referring now to FIG. 17, a process for analyzing ECG data and grouping similar beats is illustrated. This process generally involves receiving ECG data of a patient at step 211. This may involve receiving raw ECG data 52 at ECG platform 37. The raw ECG data may, optionally, be preprocessed as described above (e.g., to remove noise). Upon receiving the ECG data, at step 212 the ECG data may be analyzed and/or processed using at least one delineation algorithm to generate wave information. The embedding algorithm may be one or more algorithms and/or a neural network. The wave information generated may be wave information 201. At step 213, beat onsets and offsets may be determined from the wave information. Based on the beat onsets and offsets, a portion of ECG data starting at a time point corresponding to an offset and ending at a time point corresponding to an onset may be extracted from the ECG data and associated with that particular beat. A plurality of beat portions of ECG data may be extracted at step 213. At step 214, the portions of ECG data corresponding to the beats may be analyzed and/or processed using an embedding algorithm to generate embedding data. Embedding data may be embedding data 203. The embedding algorithm may be one or more algorithms and/or a neural network. The embedding data generated by the embedding algorithm may be representative of a portion of ECG data corresponding to a beat.

At step 215, the embedding data may be analyzed and/or processed using a grouping algorithm to generate group data. The group data may be group data 205. The grouping algorithm may be one or more algorithms (e.g., kmeans, dbscan) and/or a trained neural network. The grouping algorithm is preferably trained from a plurality of ECG data sets and/or portions of ECG data corresponding to various beats. At step 216, group data may be analyzed to determine whether two or more beats are similar (e.g., share certain features and/or characteristics). For example, a group data value may be compared to a threshold of range to determine similarity between beats. If a group data value indicates a similarity between beats (e.g., if the group data value satisfied the threshold), the similar beats may be grouped together.

At step 217, information regarding ECG data, wave information, labels, embedding data, group data, groups of beats, similar beats, clusters, episodes, morphologies, and/or other information based on or indicative of any of the foregoing (e.g., analyzed ECG data) may be transmitted from ECG platform 37 to ECG application 29 for display. Some or all of the analyzed ECG data may be displayed on a graphic user interface. For example, a graphic user interface similar to interactive display 220 illustrated in FIG. 18 may display morphology 240 and other analyzed ECG data. The graphic user interface may include a beat overlay image of sample beats within that morphology, as is illustrated in FIG. 20B.

At optional step 218, a request to assign the analyzed ECG data to one or more user accounts associated with one or more healthcare professionals may be received by ECG platform 37 and ECG platform 37 may assign the analyzed ECG data to that user account. In addition to assigning the analyzed ECG data to a healthcare professional (e.g., technician, cardiologist, etc.), the system may inform that healthcare professional that ECG data has been assigned to them for review. For example, a message and/or alert may be sent to that healthcare professional. The analyzed ECG data may be unassigned and/or reassigned as well. It is understood that optional step 218 may alternatively occur after or between steps 219, 220, and/or 221, or at any other point. At optional step 219, the analyzed ECG data may be submitted for quality control, the request for quality control may be received by ECG platform 37 and/or the analyzed ECG data may be placed in a quality control queue for review by one or more quality reviewers (e.g., technicians).

At optional step 220, ECG platform 37 may receive quality control input from one or more quality reviewers (e.g., technicians). The quality control input may include deleted and/or modified portions of analyzed ECG data. At optional step 221, ECG platform 37 may transmit quality control input to the ECG application 29 for display. ECG application may show analyzed ECG data that has been selected for deletion and/or modification. Steps 220 and/or 221 may be repeated multiple times if multiple quality control reviewers review the analyzed ECG data. For example, a first quality control reviewer may indicate that the analyzed ECG data requires further review and a second quality control reviewer may analyze the analyzed ECG data and/or the quality control input generated during the first quality control review.

At step 222, ECG platform 37 may receive user input data from ECG application 29. For example, a healthcare professional (e.g., the assigned healthcare professional), may review the analyzed ECG data and/or quality control input and may generate user input data regarding the analyzed ECG data and/or quality control input (e.g., regarding an inaccuracy in the analyzed ECG data). The user input data may be a deletion and/or modification of some or all of the analyzed ECG data. The user input data may be generated by input device 25 of system device 14 and transmitted to ECG platform 37 from ECG application 29. For example, the user input data may correspond to the accuracy of the graphic user interface which may correspond to the accuracy of the embedding data and/or group data. As explained below with respect to FIG. 20A, user input data may correspond to a morphology being deleted. For example, a clinician may delete a morphology using input device 25 if, after reviewing the displayed morphology, the healthcare provider or technician determines that the sample beats within that morphology are normal rather than abnormal.

At optional step 223, the received user input data and/or quality control input may be used to train and/or modify the delineation algorithm, classification algorithm, grouping algorithm and/or the embedding algorithm (e.g., using recomputer 40). For example, the user input data may inform ECG platform 37 that certain episodes and/or beat groups should be deleted and/or otherwise are inaccurate. This information may be used to retrain or otherwise modify the delineation algorithm, classification algorithm, grouping algorithm and/or the embedding algorithm to improve the quality of the wave information, labels, embedding data and/or group data generated by these algorithms.

At optional step 224, ECG data (e.g., preprocessed ECG data) may be reanalyzed and/or recalculated based on the modified delineation algorithm, classification algorithm, grouping algorithm and/or the embedding algorithm to generate reanalyzed ECG data (e.g., wave information, labels, embedding data, group data, groups of beats, similar beats, clusters, episodes, morphologies, and/or other information based on or indicative of any of the foregoing). At step 225, reanalyzed ECG data and/or other information indicative of or based on reanalyzed ECG data may be transmitted from ECG platform 37 to ECG application 29 for display. The data and/or information may be displayed on a graphic user interface. For example, a graphic user interface may be updated to delete a morphology as instructed in the user input data. Additionally, or alternatively, recomputed episodes or clusters may be displayed.

Figure 18:
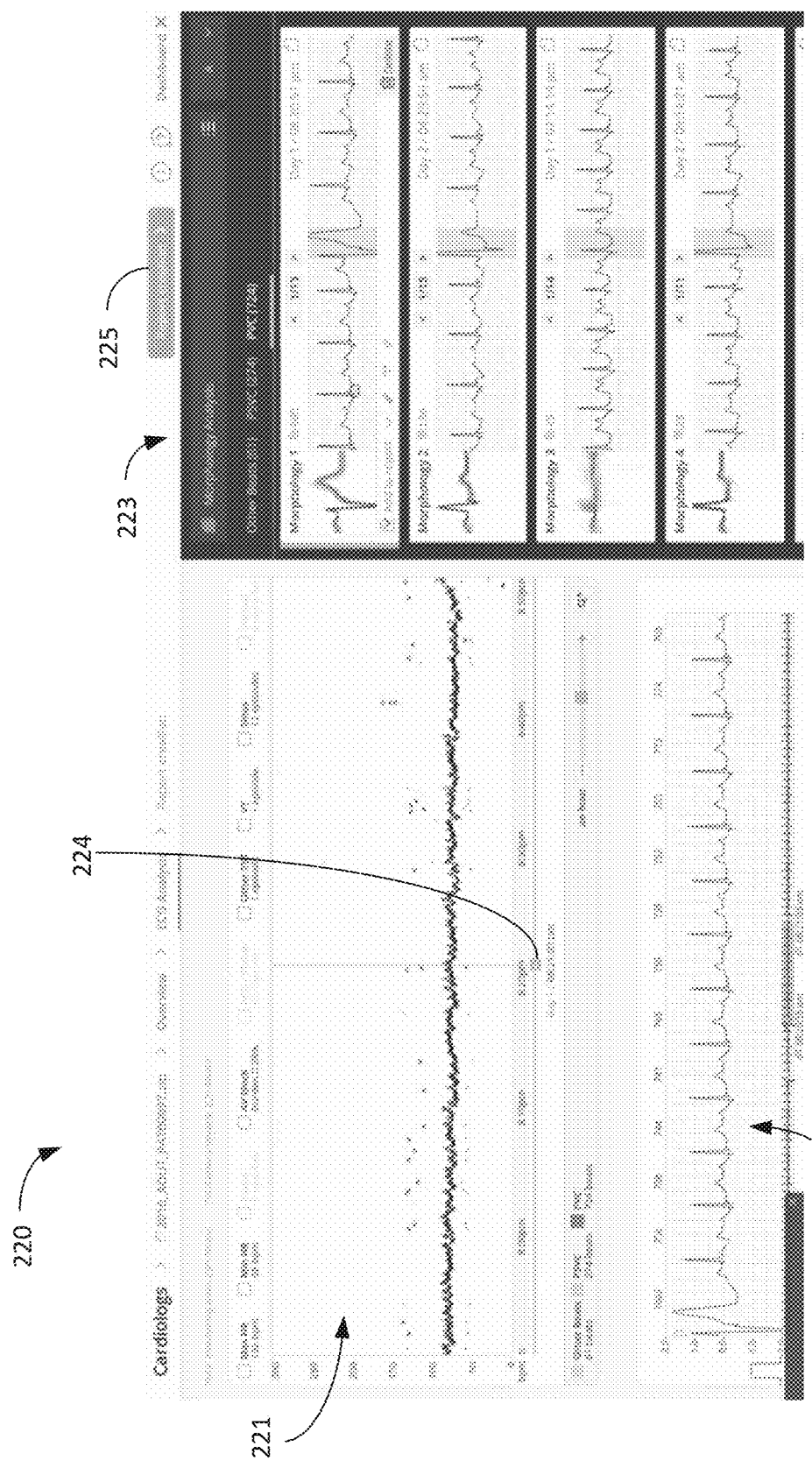
FIG. 18 is an exemplary graphic user interface illustrating a plurality of morphologies.

Referring now to FIG. 18, interactive display 220 is illustrated. Interactive display 220 includes first graphic window 221, which is similar to first graphic window 124, and second graphic 222, which is similar to second graphic window 125. Interactive display 220 may also include report creation button 225 for generating a report. First graphic window 221 may illustrate a plurality of beats over a certain time period and may include curser 224 similar to curser 136. Second graphic window 222 may include a zoomed in view of a region of the plurality of beats selected by curser 224. Interactive display 220 may further include third graphic window 223 which may include analysis or additional information about the plurality of beats in first graphic window 221. For example, third graphic window 233 may illustrate one or more morphologies, each including a plurality of beat strips that have matched or otherwise grouped together based on certain similarities, as described above. In some embodiments, a beat strip is a plurality of consecutive beats in time. The plurality of beat strips matched or otherwise grouped together generally are from different time intervals and are not consecutive strips in time.

Figure 19:
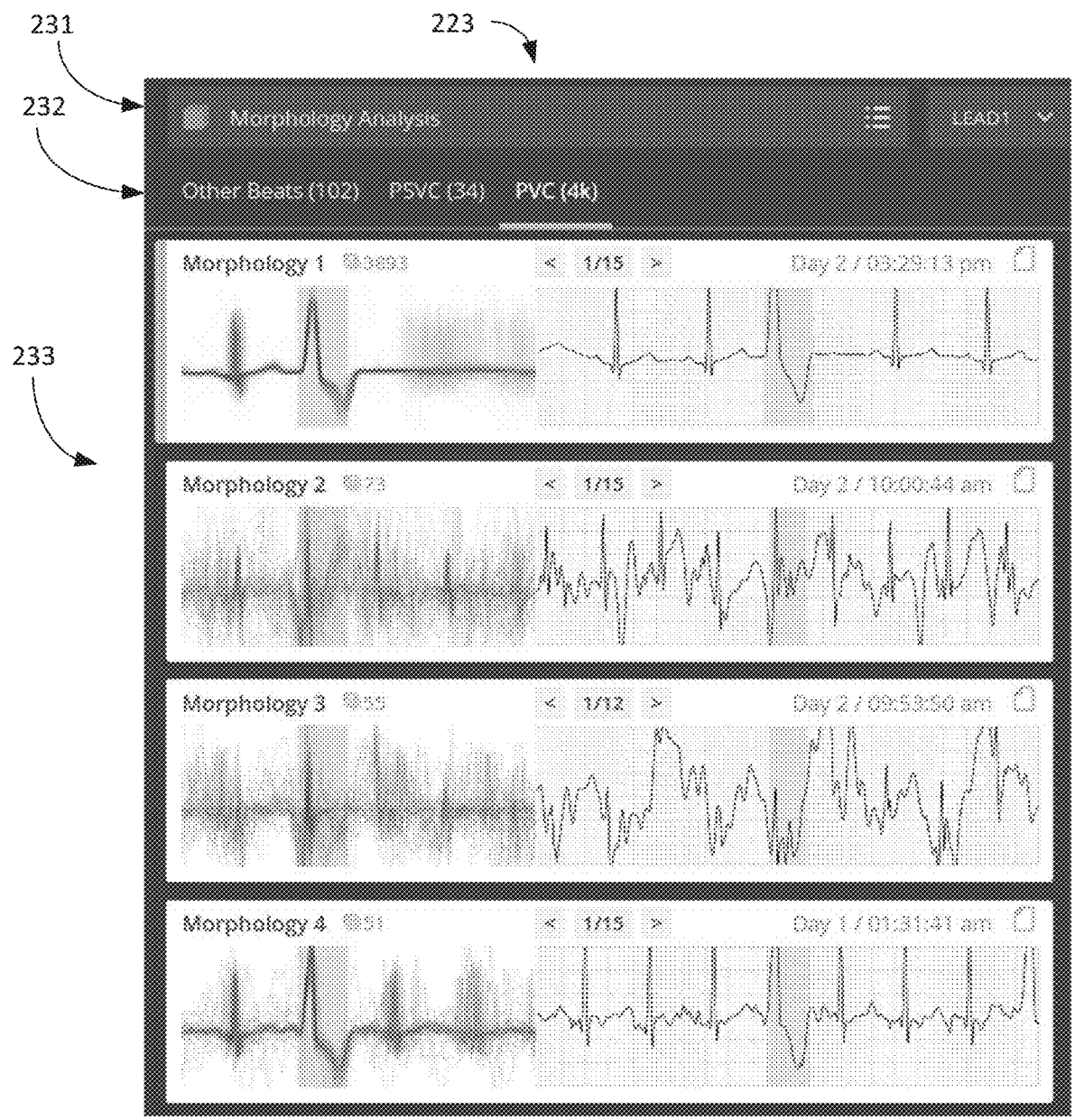
FIG. 19 illustrates a third graphic window of the graphic user interface.

Referring now to FIG. 19, third graphic window 223 is illustrated. As shown, third graphic window 223 may include category tab 231 for selecting information to be displayed in third graphic window 223, such as morphology analysis, ventricular activity or any other category listed in navigation window 259 (shown in FIG. 21). Third graphic window 223 may further also include subtabs 232 to further narrow category tab 231. For example, subtabs 232 include types of abnormalities, such as PVC and PSVC, or generic tabs such as "other beats." When the "morphology analysis" window tab is selected, morphologies 233 may be viewed using interactive display 220. As explained above, each morphology of morphologies 233 may include a group of beat strips that have been grouped together based on group data. For example, each morphology may include beats having one or more similar characteristics or qualities.

Figure 20A:
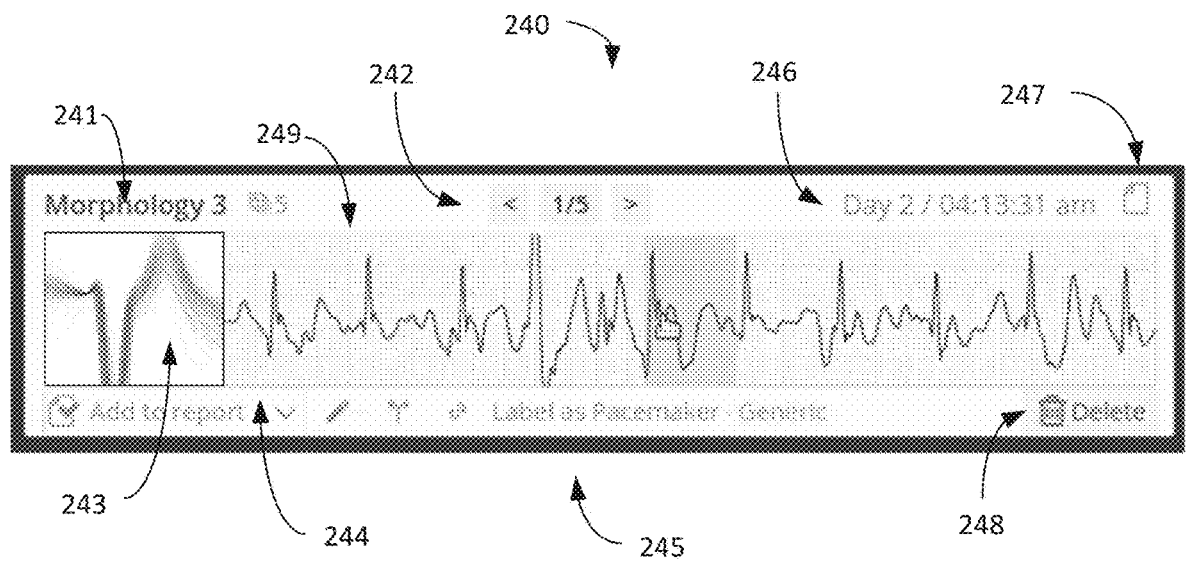
FIGS. 20A and 20B illustrate an exemplary morphology and beat overlay.
Figure 20B:
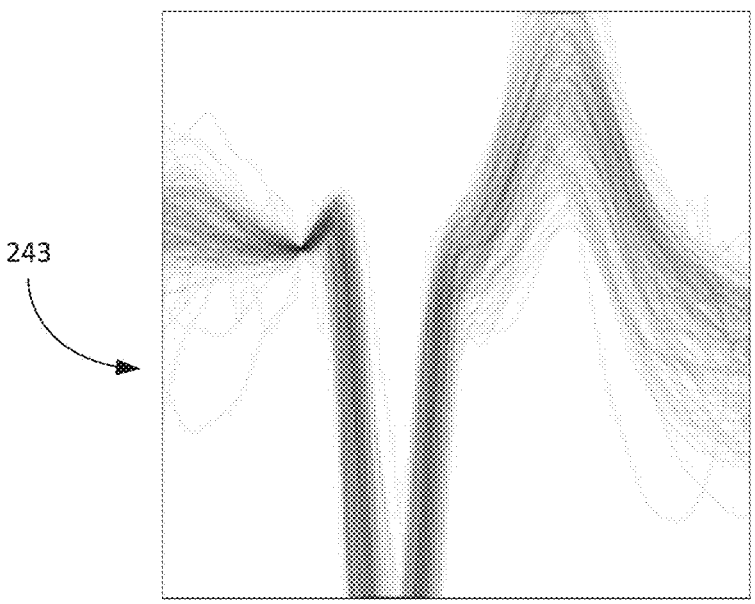

Referring now to FIG. 20A, morphology 240 is illustrated which is exemplary of one morphology of morphologies 233. Morphology 240 may involve morphology name 241, morphology navigator 242, beat overlay 243, add to report button 244, miscellaneous information 245, time identifier 246, report button 247, delete button 248, and beat window 249. Morphology name 241 may identify the morphology. Morphology navigator 242 may be used to select a beat strip within morphology 240 to view in beat window 249. The beat strips that may be displayed in morphology navigator 242 may be a subset of beat strips of the total beat strips in that morphology. The subset of beat strips may be randomly selected from the total beat strips or, in a preferred embodiment, selected based on the beat strips within that morphology that have the greatest differences from one another. For example, the subset may be generated by comparing group data and/or embedded data to determine the beat strips within that morphology that have vector and/or matrix values with the largest differences from one another. In this manner, morphology navigator 242 displays relevant beat strips for the morphology based on a score. Add to report button 244 may be used to add morphology 240 to a report to be generated by ECG platform 37 using report generation button 225. Miscellaneous information 245 may include certain information about the patient or morphology. For example, miscellaneous information 245 may identify that the patient has a pacemaker. Time identifier 246 may identify a time at a certain point within beat window 249. For example, a user may place a curser over a point in beat window 249 and time identifier 246 may identify the corresponding time. Report button 247 may be used to open a report or report template. Delete button 248 may be to delete morphology 240. For example, after reviewing morphology 240, a healthcare provider or technician may decide that the beats in the morphology are not similar, are normal, and/or otherwise should not be grouped together, and thus may decide to delete the morphology. As explained above with respect to FIGS. 16 and 17, deleting the morphology may alter the graphic user interface (e.g., interactive display 220) and/or may cause the grouping algorithm to be modified or otherwise altered to retrain the neural network.

Referring now to FIG. 20B, beat overlay 243 is enlarged. As show, beat overlay 243 may display some or all similar beats within morphology 240 on a single plot. For example, beat overlay 243 may display a single beat from each of the beat strips of morphology navigator 242 overlaid over one another. In a preferred embodiment, the displayed beat in beat overlay 243 from each of the beat strips is a beat identified by the system as abnormal in the respective beat strip. ECG platform 37 may align the beats according to a wave or plot feature (p-wave, t-wave, QRS complex). A healthcare provider or technician may use beat overlay 243 to determine if the morphology is abnormal, similar, and/or if it is accurately categorized in the appropriate subtab. If the healthcare provider or technician determined that the beats in the morphology are not similar, are normal, and/or otherwise should not be grouped together, the healthcare provider or technician may delete the morphology using delete button 248, as described above.

Figure 21:
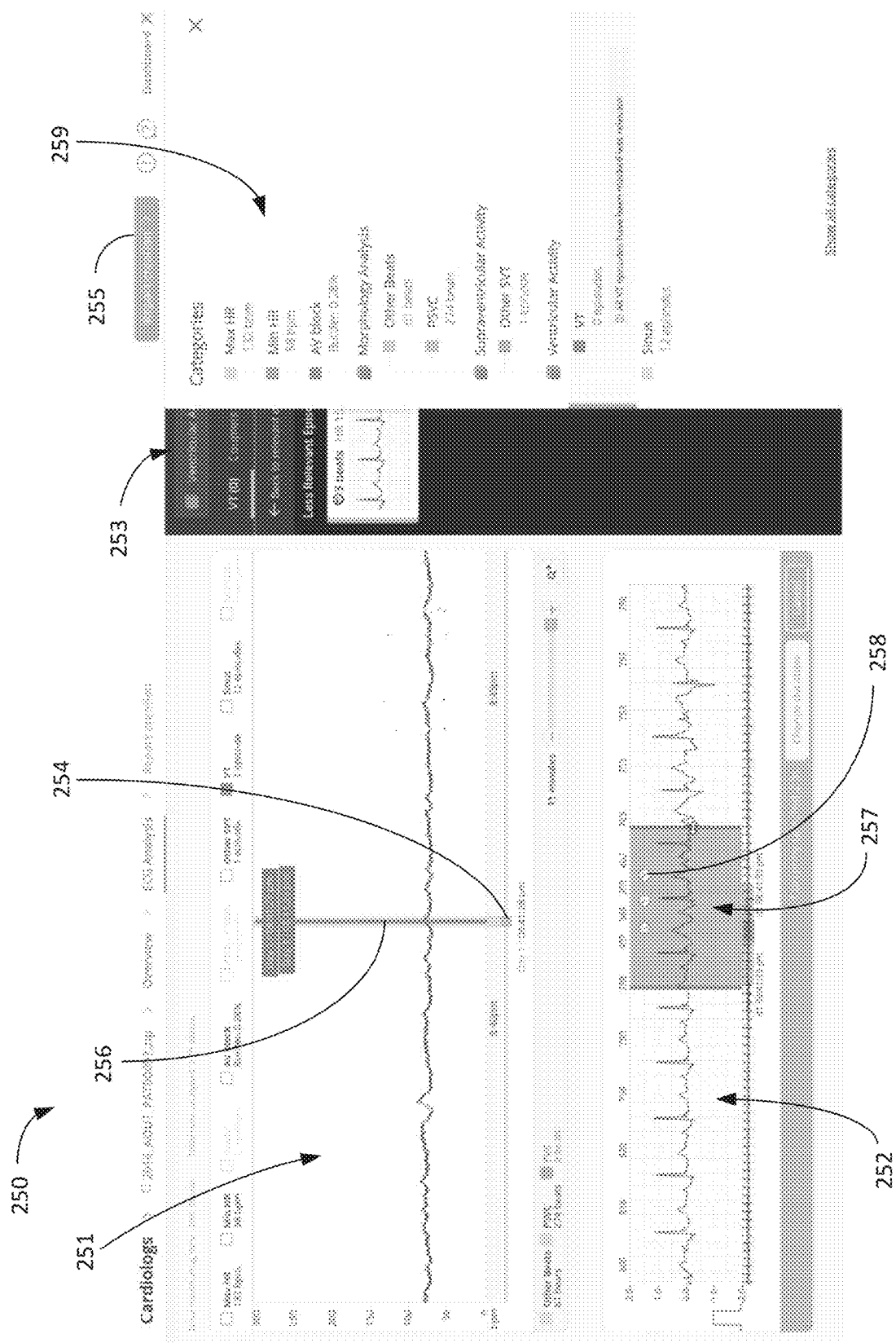
FIG. 21 is an exemplary graphic user interface illustrating an ectopic run.

Referring now to FIG. 21, interactive display 250 is illustrated. Interactive display 250 includes first graphic window 251, which is similar to first graphic window 221, and second graphic 252, which is similar to second graphic window 222. First graphic window 251 may illustrate a plurality of beats over a certain time period and may include curser 254 similar to curser 224. Second graphic window 252 may include a zoomed in view of a region of the plurality of beats selected by curser 254. Interactive display 250 may further include third graphic window 253 illustrating one or more categories. Interactive display 250 may also include navigation window 254 and report creation button 255 for generating a report. Navigation window 259 may be used for selecting various categories to be viewed within third graphic window 253. For example, navigation window 259 may be used to select categories including, but not limited to Max HR, Min HR, AV block, Morphology Analysis such as Other Beats and PSVC, Supraventricular Activity such as Other SVT, Ventricular Activity such as VT, and/or sinus.

Interactive display 250 may also display ectopic runs in the plurality of beats contained within first graphic window 251. An ectopic run is three or more abnormal beats that are consecutive in time. Thus, the systems described herein may detect an ectopic run when three or more abnormal beats in a row are identified, e.g., using the identifier described above. First graphic window 251 may identify an ectopic run with identifying bar 256 at the point of the ectopic run. Second graphic window 252 may identify a region of the ectopic run with ectopic section 257 which may be a different color than second graphic window 252. Each ectopic beat within ectopic section 257 may be identified with ectopic marker 258, showing the precise location of each ectopic beat.

By engaging report creation button 255 (similar to report creation button 225 of FIG. 18), a report may be created regarding the ECG data illustrated in interactive display 250. As explained above, a healthcare provider or technician using interactive display 250 may select morphologies or various other beat strips or groups of beat strips displayed using navigation window 259 to include in the report. FIGS. 22A-22P illustrate report 260, which is an exemplary report that may be generated using ECG platform 37 and ECG application 29.

Referring now to FIG. 22A, report 260 may include cover page 261 including information about the patient, information about a healthcare provider or technician, a summary of the report, information about the patient's heart rate (e.g., max, min, avg.), ectopic information (e.g., premature supraventricular complexes, premature ventricular complexes), information about patient events, information about paced beats, and a findings section identifying including the most notable findings, results and/or analyses. Cover page 261 may further include notable beat strips corresponding to ECG data of the patient. For example, notable beat strips may include, but are not limited to, AFib/Flutter, Other SVT, Pause, AV Block, VT.

Figure 22B:
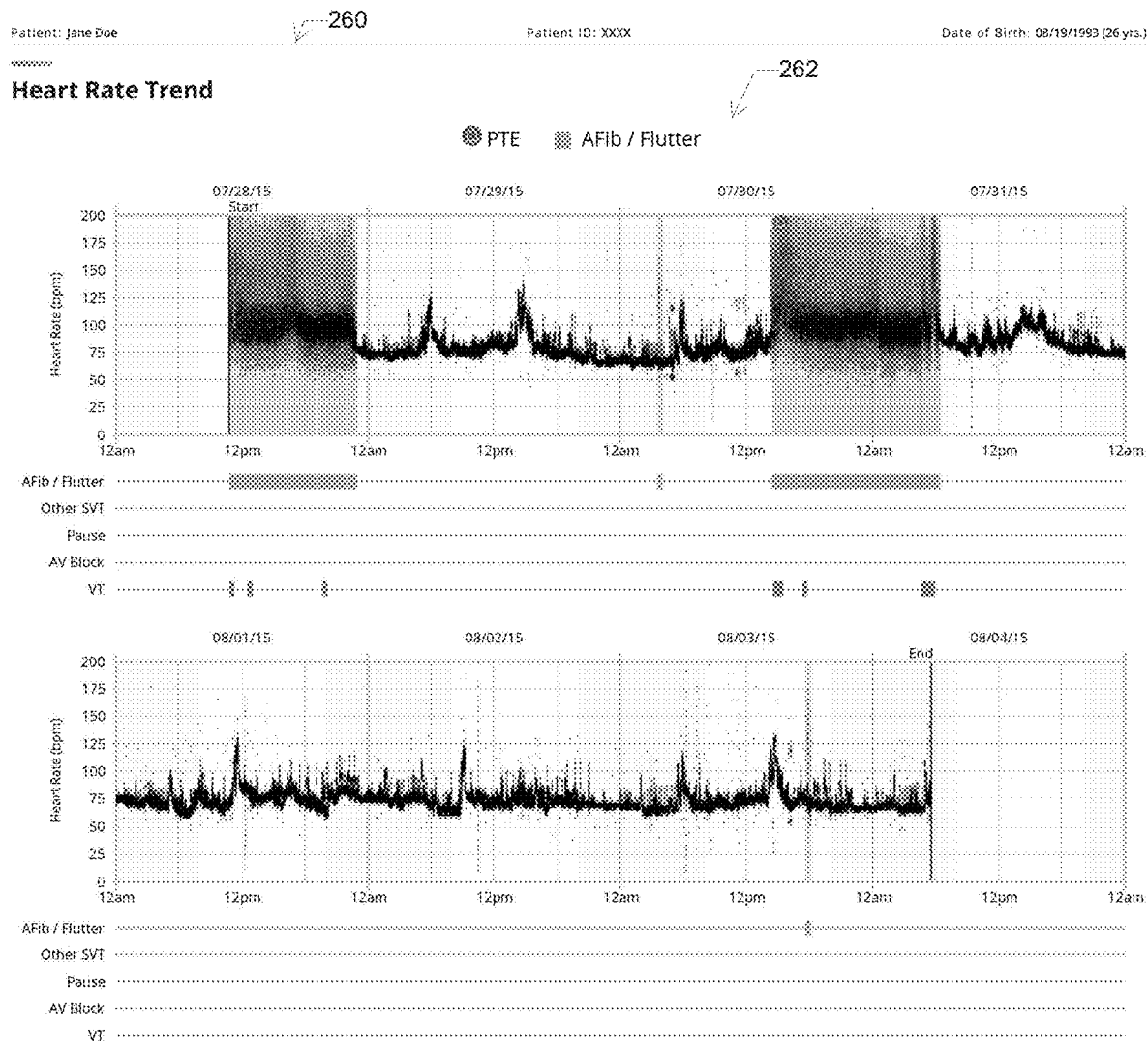
FIGS. 22A-22P is an exemplary report generated by the ECG processing system.
Figure 22C:
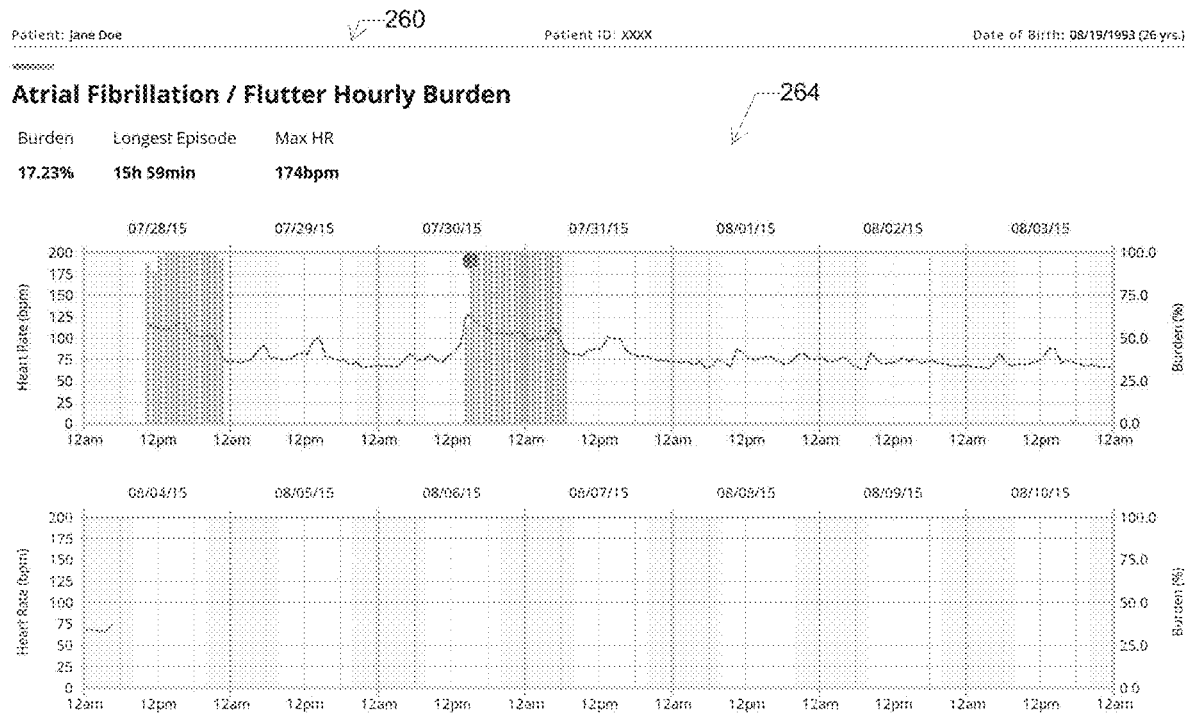

Referring now to FIG. 22B, report 260 may include heart rate trend display 262 which may illustrate the patient's heart beat over a certain time period (e.g., several hours). Heart rate trend display 261 may also include one or more abnormality identifiers 263 for identifying abnormalities in the displayed beats over time. Heart rate trend display may also identify PTE and/or Afib/flutter. Referring now to FIG. 22C, report 260 may include Afib/flutter display 264 which may display the patient's heart rate over a certain time period (e.g., several hours). Afib/flutter display 264 may be used to display times at which the patient is experiencing atrial fibrillation and/or flutter. Afib/flutter display 264 may further display a burden percentage, length of time of the longest episode, and max heart.

Figure 22D:
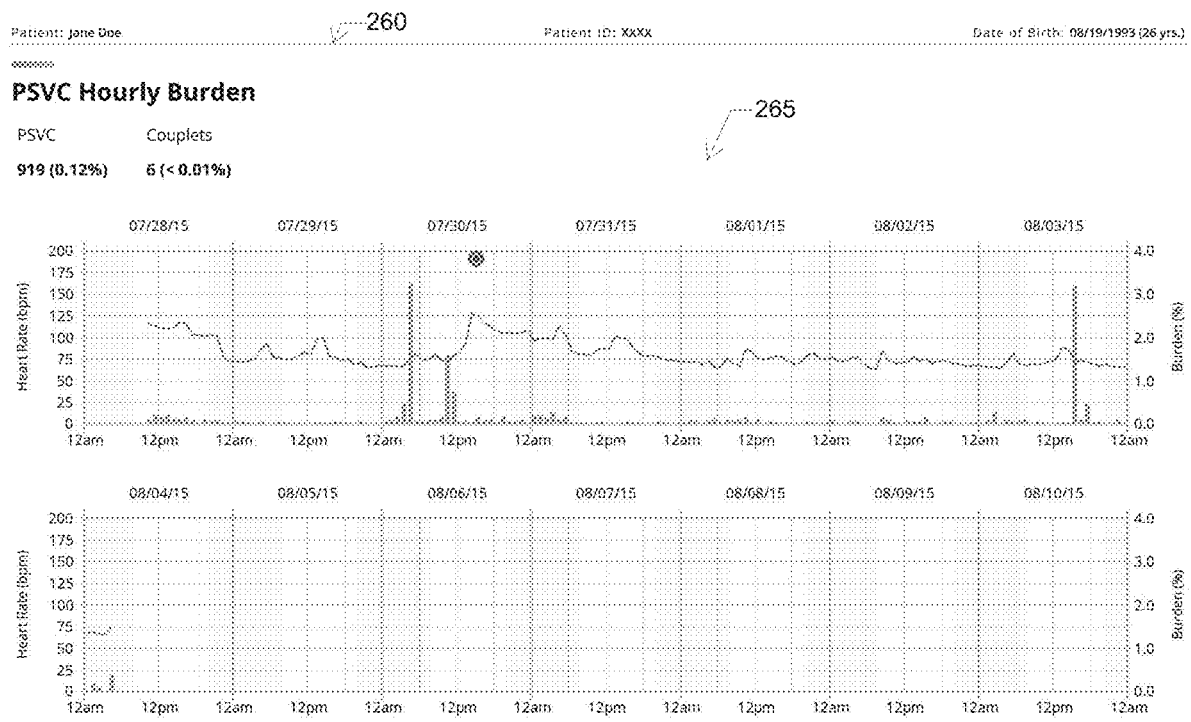
Figure 22E:
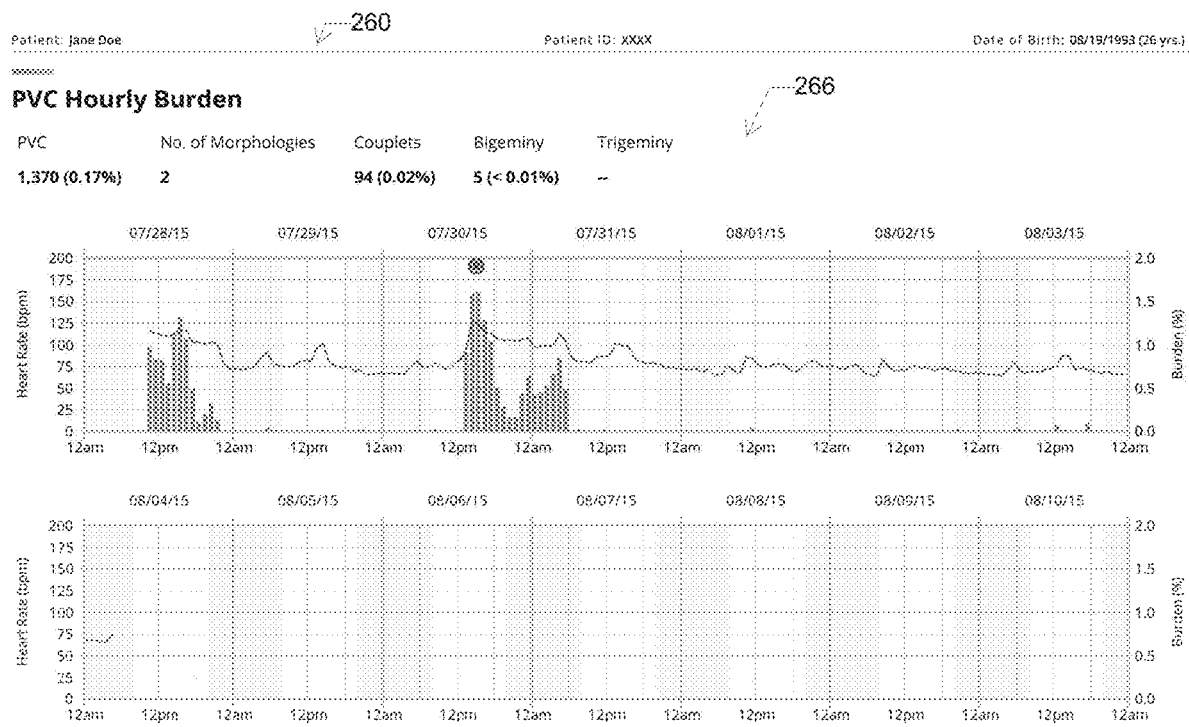

Referring now to FIG. 22D, report 260 may include PSVC display 265 which may display the patient's heart rate over a certain time period (e.g., several hours) and may be used to display times at which the patient is experiencing PSVC. PSVC display 265 may further display a PSVC value and a couplet number and/or percentage. Referring now to FIG. 22E, report 260 may include PVC display 266 which may display the patient's heart rate over a certain time period (e.g., several hours) and may be used to display times at which the patient is experiencing PVC. PVC display 266 may further display a PVC value and/or percentage, a number of morphologies relevant to PVC, a number and/or percentage of couplets, a bigeminy number and/or percentage and a trigeminy number and/or percentage.

Figure 22F:
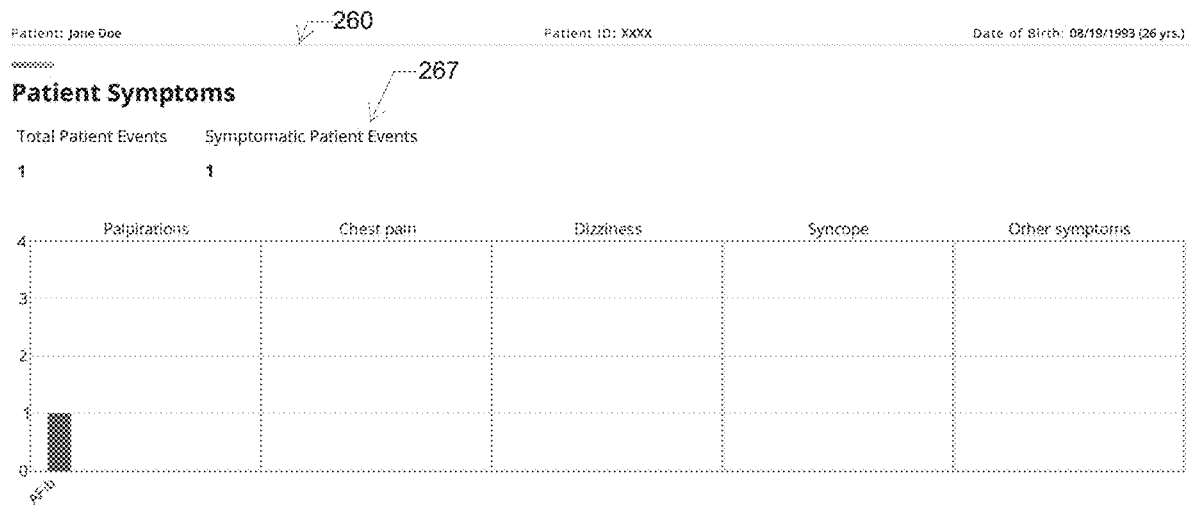
Figure 22G:
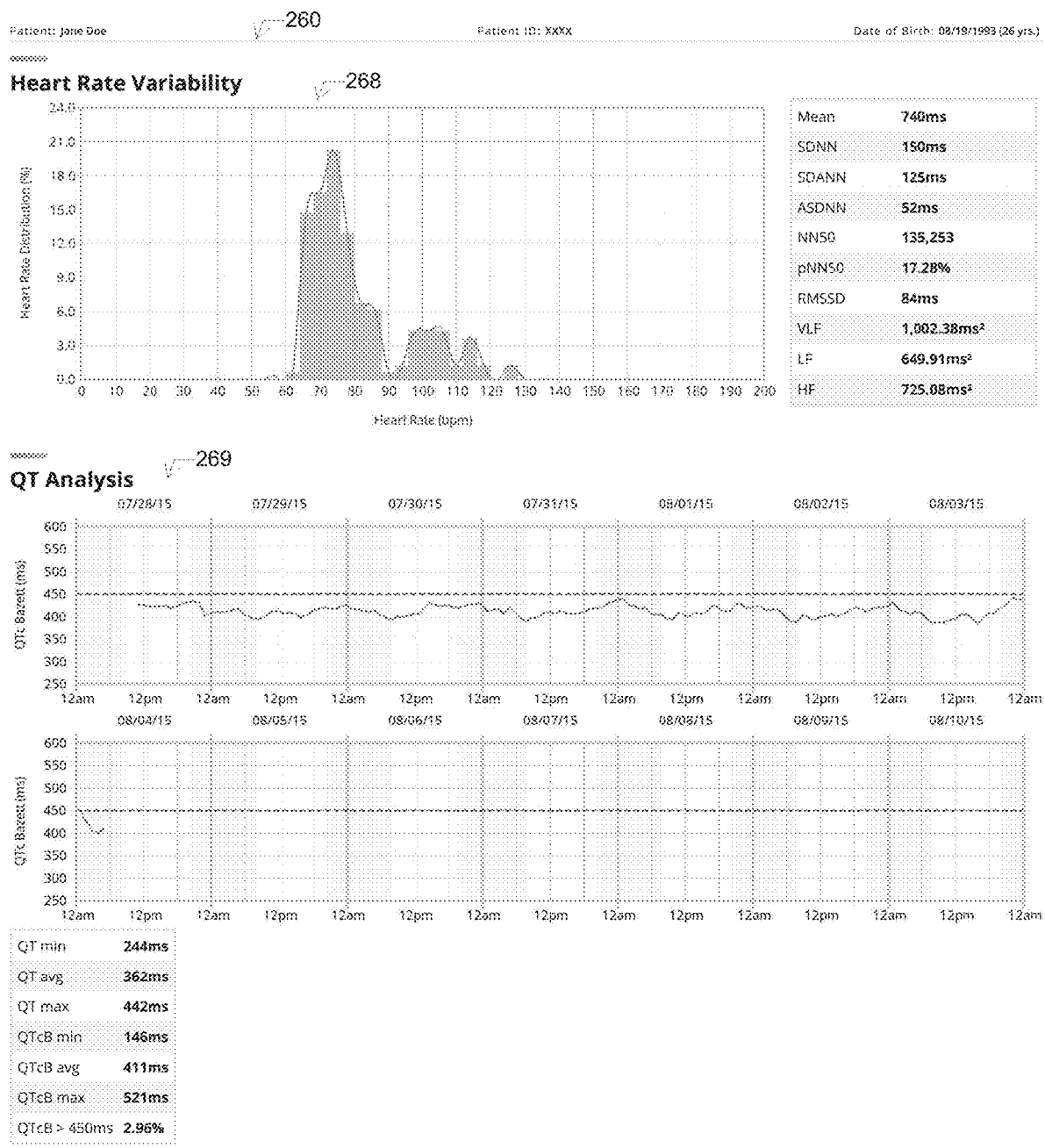

Referring now to FIG. 22F, report 260 may include patient symptom display 267 which may identify patient systems that are detected and may include the total number of patient events and the number of symptomatic patient events. Patient symptom display 267 may be broken up into palpitations, chest pain, dizziness, syncope, and other symptoms. Referring now to FIG. 22G, report 260 may include heart rate variability display 268 and QT analysis display 269. Heart rate variability display 268 may identify heart rate distribution and variability and display heart rate parameters such as mean, SDNN, SDANN, ASDNN, NN50, pNN50, RMSSD, VLF, LF, and HF. QT analysis display 269 may analyze and display QT analysis over time and identify parameters such as QT min, QT avg, QT max, QTcB min, QTcB avg, QTcB max, and QTcB>450 ms.

Referring now to FIG. 22H, report 260 may include strip index 271. Strip index 271 may include parameters like ID, date and time, category, heart rate, patient event, comments, and page. Category may include items such as Max HR, Min HR, Sinus, AFib/Flutter, VT, Patient Event, PVC, Ventricular Couplet, Ventricular Bigeminy, PSVC, Supraventricular Couplet. Index strip 271 may be used to find the report page number at which a beat strip displaying a certain category may be found.

Figure 22I:
Figure 22J:
Figure 22K:
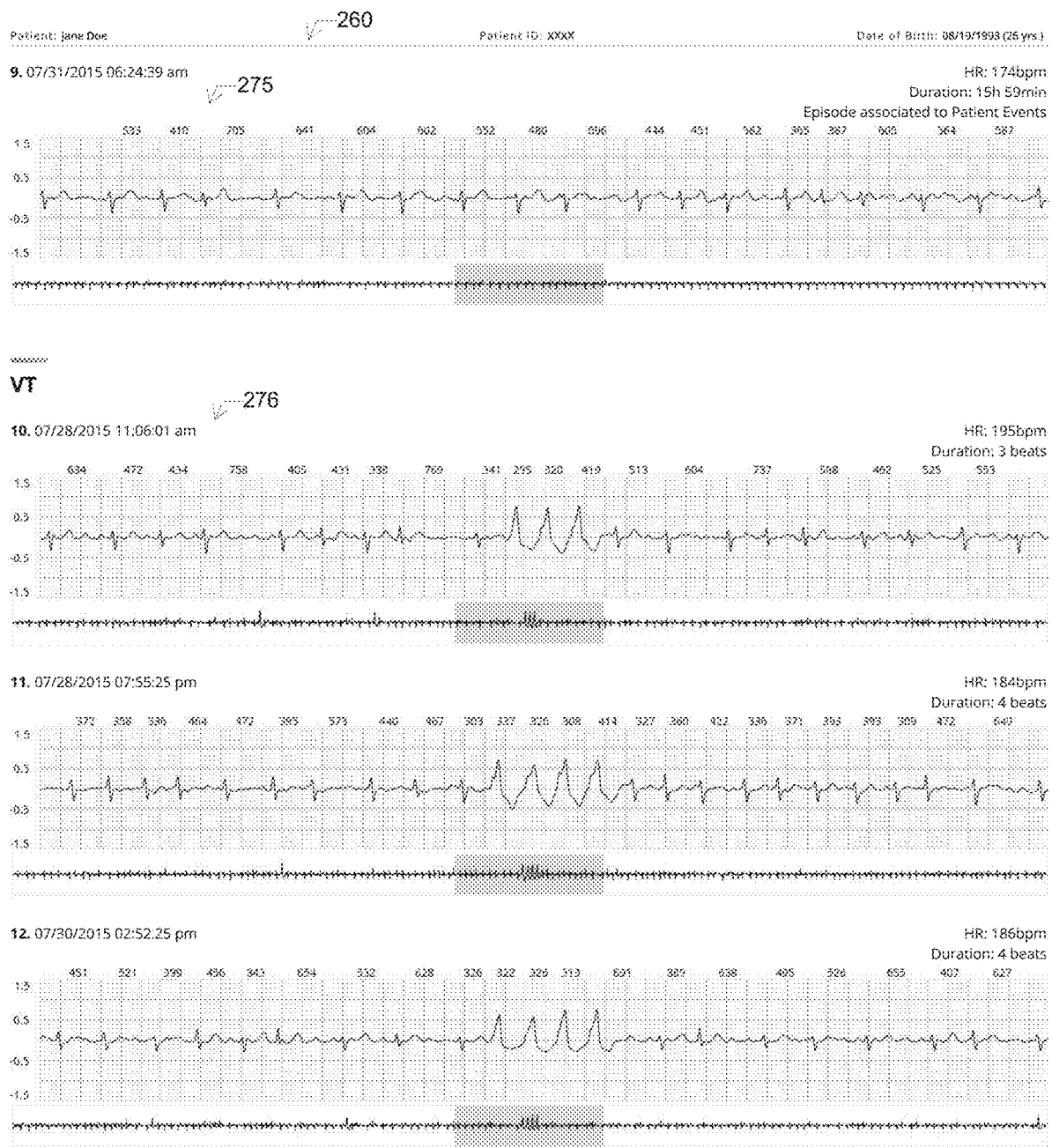
Figure 22L:
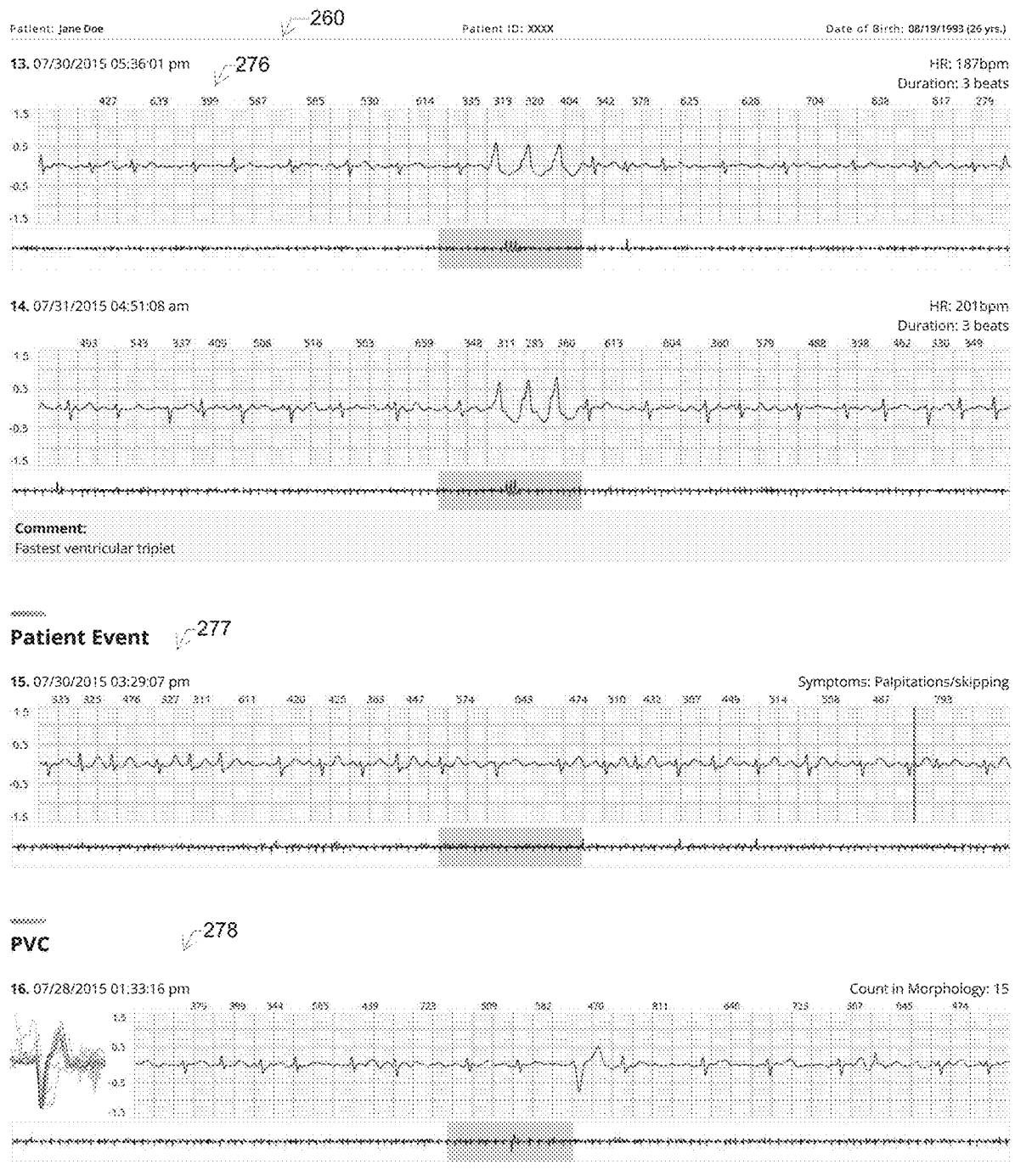
Figure 22M:
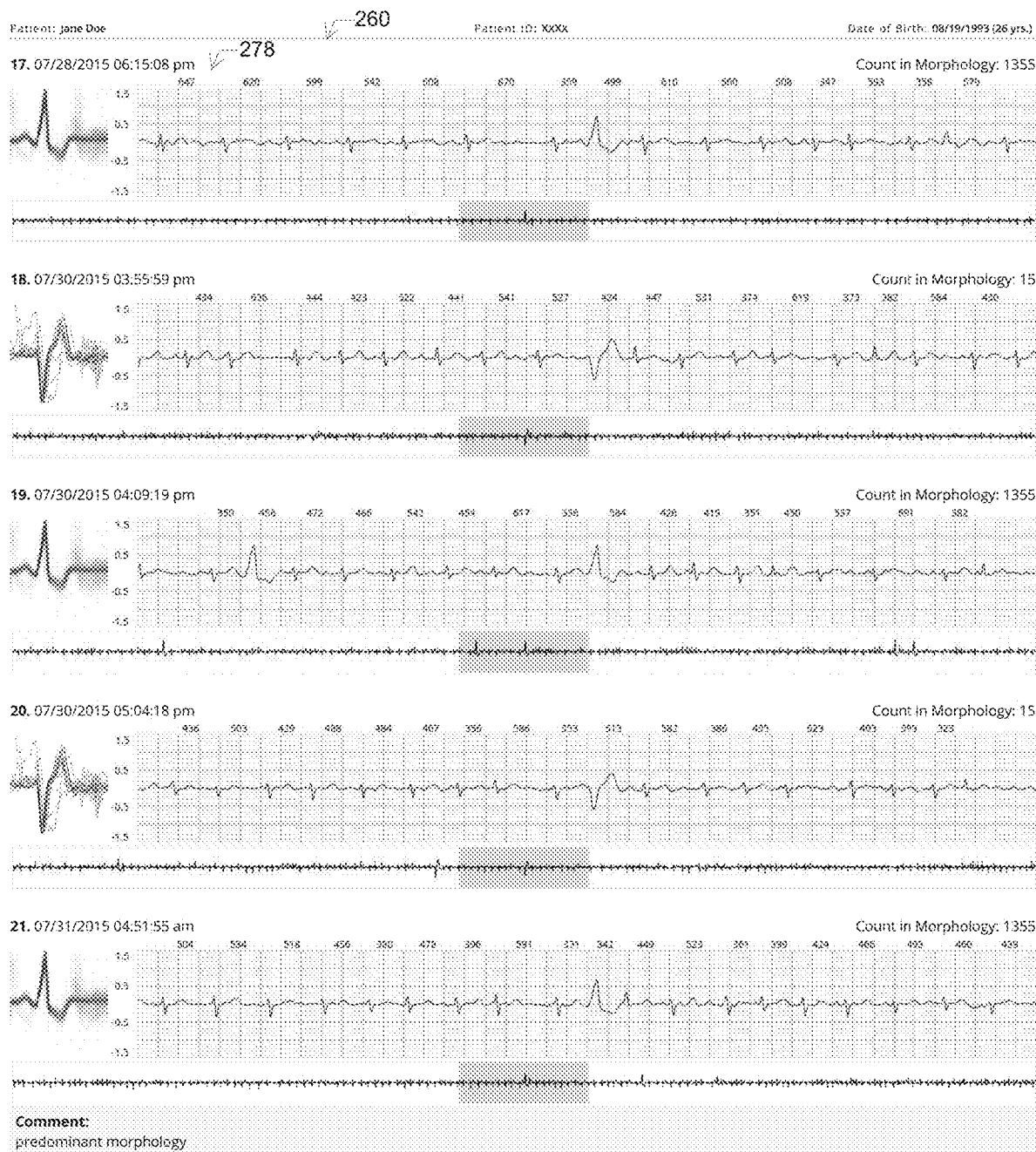
Figure 22N:
Figure 22O:
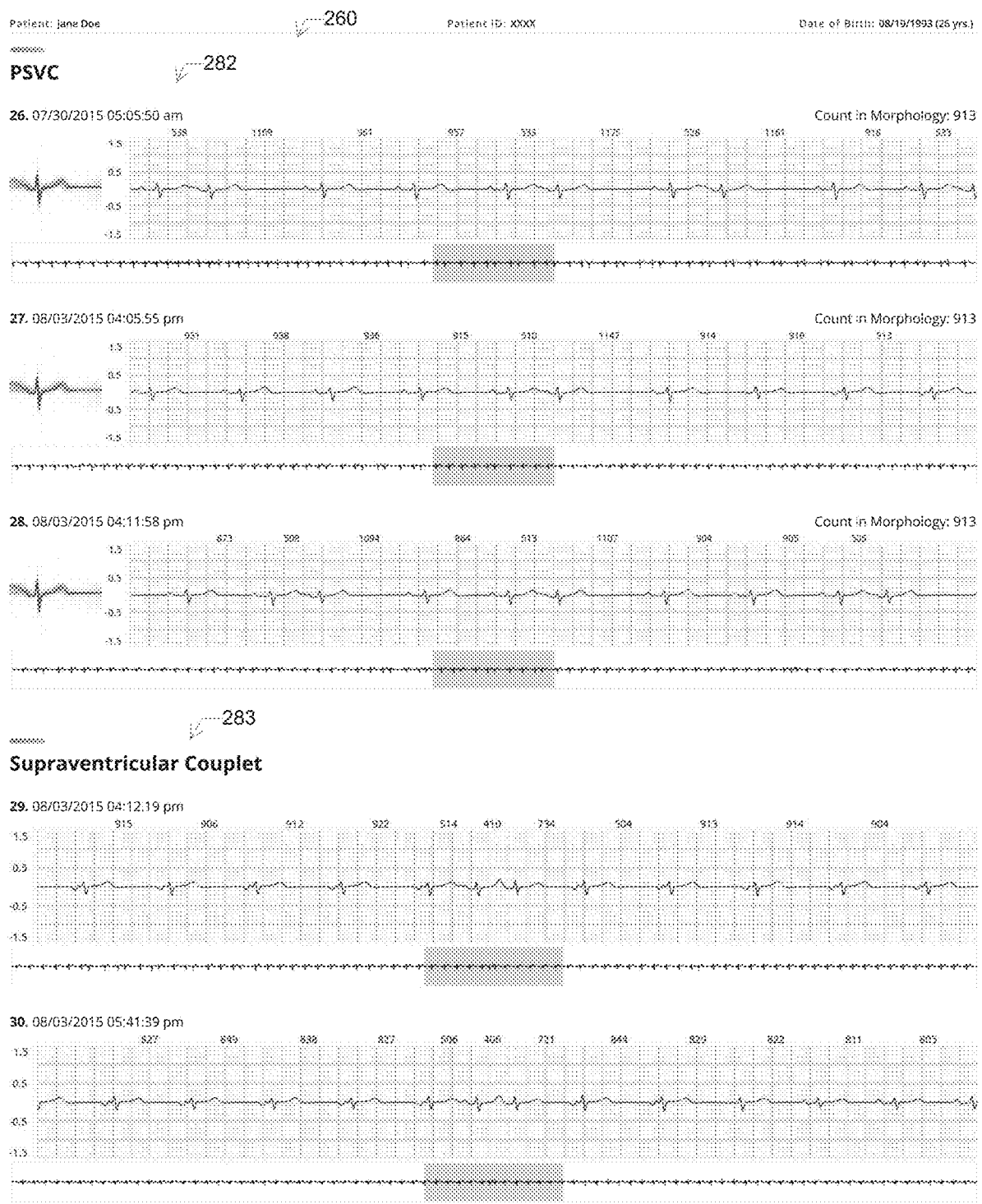
Figure 22P:
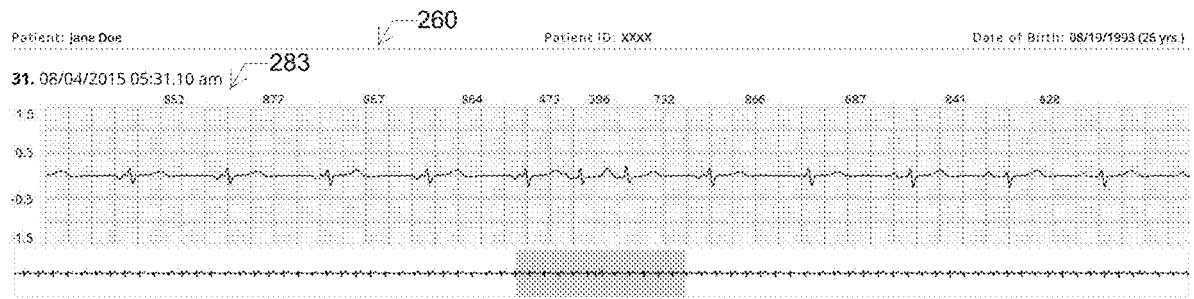

Referring now to FIG. 22I, report 260 may include beat strip displays such as max HR display 272, min HR display 273, and sinus display 274. Max HR display 272 may display beat strips with a maximum heart rate. Minimum HR display 273 may display beat strips with a minimum heart rate. Sinus display 274 may display beat strips with a sinus abnormality. Referring now to FIG. 22J, report 260 may include beat strip displays such as sinus display 274 and afib/flutter display 275. Afib/flutter display 275 may display beat strips showing atrial fibrillation and/or flutter. Referring now to FIG. 22K, report 260 may include beat strips such as afib/flutter display 275 and VT display 276. VT display 276 may display beat strips showing VT. Referring now to FIG. 22L, report 260 may include beat strips such as VT display 276, patient event display 277, and PVC display 278. Patient event display 277 may display beat strips showing a patient event. PVC display 278 may display beat strips showing PVC. FIG. 22M illustrates additional PVC displays 278. Referring now to FIG. 22N, report 260 may include beat strips such as ventricular couplet 279 and ventricular bigeminy 281. Ventricular couplet 279 may display beat strips showing one or more ventricular couplets. Ventricular bigeminy 281 may display beat strips showing ventricular bigeminy. Referring now to FIG. 22O, report 260 may include beat strips such as PSVC display 282 and supraventricular couplet display 283. PSVC display 272 may display beat strips showing PSVC. Supraventricular couplet display 283 may display beat strips showing one or more supraventricular couplets. FIG. 22P also illustrates supraventricular couplet display 283.

Referring now to FIGS. 23A-23D, exemplary processes and user interfaces are illustrated for assigning analyzed ECG data for review. For example, FIGS. 23A-23D illustrate exemplary interfaces and processes for assigning, un-assigning, and/or reassigning review responsibilities of ECG data sets and/or analyzed ECG data to one or more healthcare professionals.

Figure 23A:
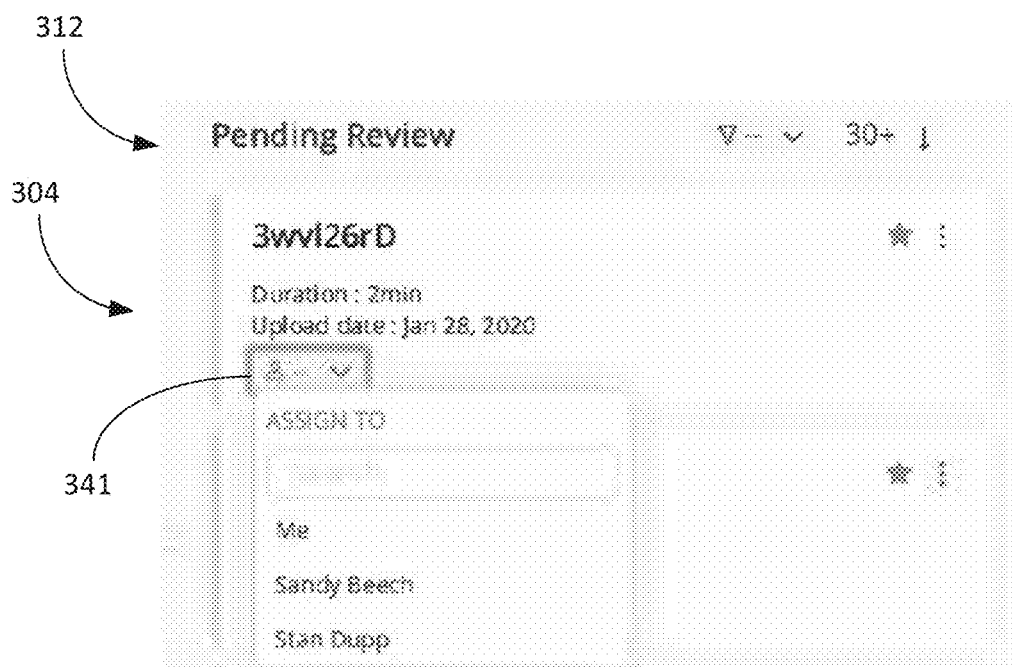
FIGS. 23A-23D illustrate user interfaces for assigning ECG data and information based on ECG data to healthcare professionals.
Figure 23B:
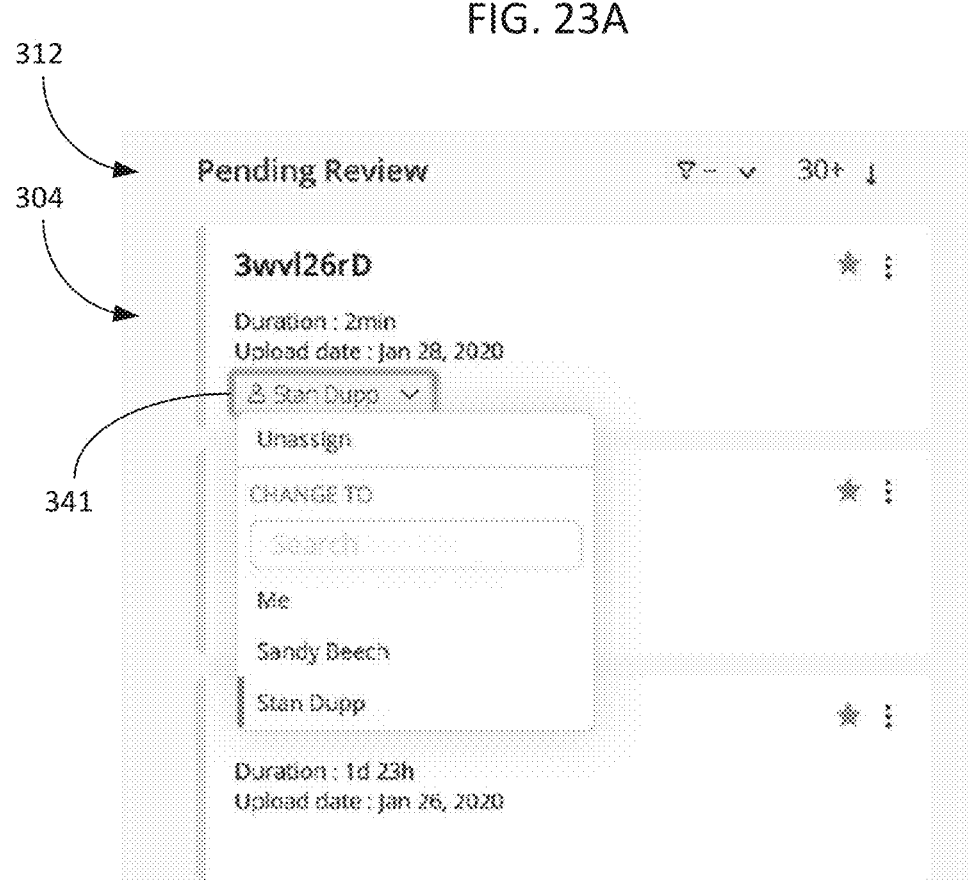

Referring now to FIGS. 23A-B, the graphic user interface displayed via ECG application 29 (e.g. on system device 14) may display pending review window 312 which may be used to assign ECG data (e.g., files) to one or more healthcare professionals. Pending review window 312 may include data status identifiers 304 which may correspond to ECG data and/or wave information, labels, group data, embedding data, classification data, delineation data, clusters, analyzed data, and/or any other data based on or corresponding ECG data. Data status identifiers 304 may indicate whether the corresponding data has been reviewed and by who. Data status identifiers 304 may also indicate which healthcare professional the data has been assigned to, if any. For example, data status identifiers 304 may include a user or data identifier, a duration value (e.g., 1 day) corresponding to a duration of ECG data, an upload date (e.g., corresponding to the date the data was uploaded to ECG platform 37), a review status corresponding to the status of the review (e.g., returned for analysis, completed, pending quality control), and/or information about who submitted the corresponding data for quality control or review and/or when the data was last modified. If there is no status, the data and/or analysis may be uploaded and ready to be analyzed. If the status is "pending quality control," the data and/or analysis may be submitted for quality control and may be ready to be reviewed. If the status is "returned for analysis," the data and/or analysis may have been reviewed but still needs further review. If the status is "completed," the data and/or analysis may have been reviewed and deemed to be acceptable.

Data status identifiers 304 may include assignment menu 341 to assign and un-assign data status identifiers 304 to one or more user accounts associated with healthcare professionals. As shown in FIGS. 23A-B, assignment menu 341 may permit a user to enter a healthcare professional's name for assigning that data status identifier 304, and thus the corresponding data, to the healthcare professional identified. Alternatively, or in addition, assignment menu 341 may list one or more names of healthcare professionals that may be selected to assign that healthcare professional to the ECG data corresponding to the data status identifier 304. Assignment menu 341 may also be used to un-assign an assigned data status identifier 304. Assignment menu 341 may also list healthcare professionals for which the data status identifier may be reassigned.

Figure 23C:
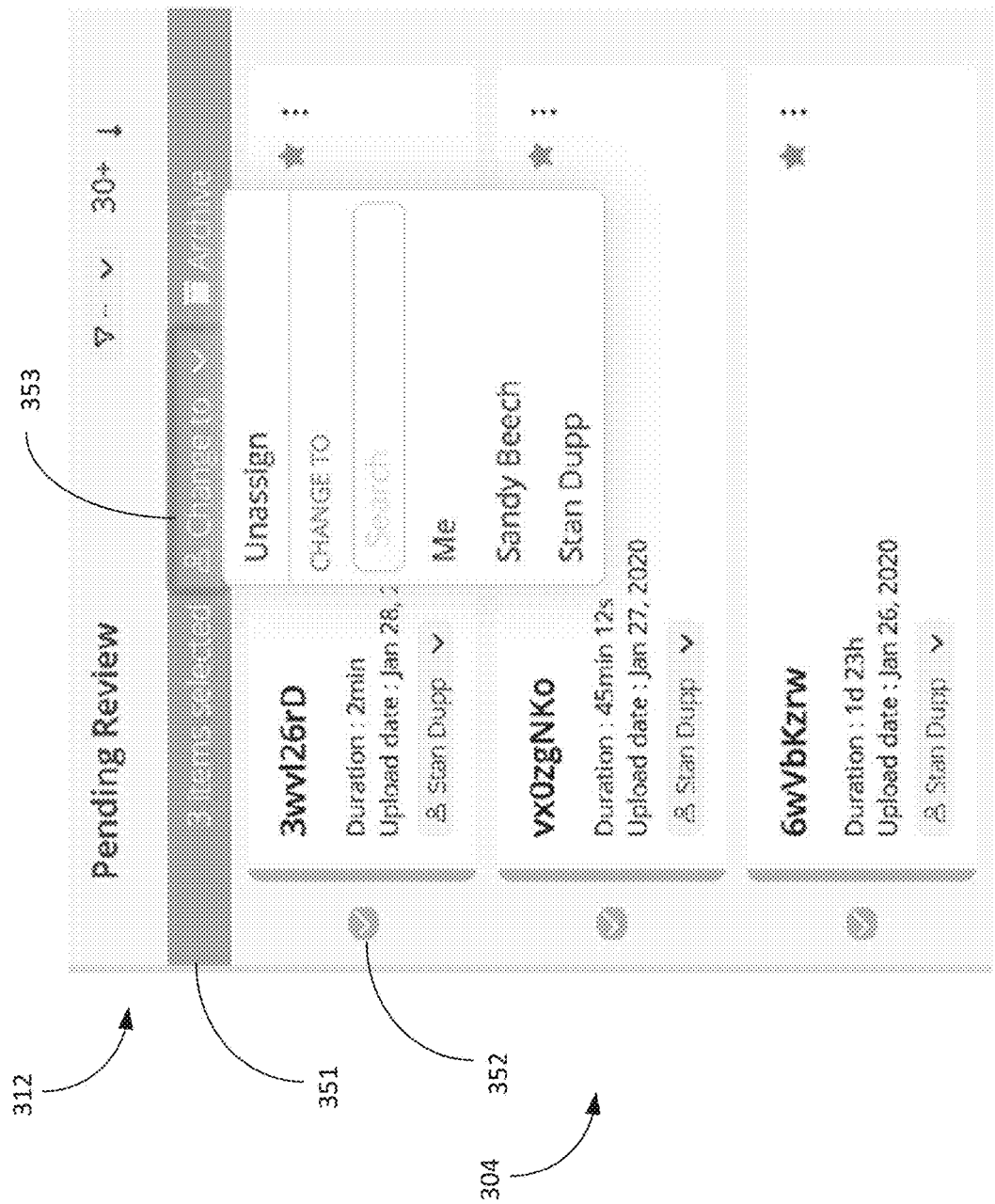

Referring now to FIG. 23C, pending review window 312 may include organization bar 351 and data selectors 352. Data selectors 352 may be engaged to select one or more data status identifiers 304. Organization bar 351 may be used to organize and/or assign data status identifiers 304. For example, change button 353 on organization bar 351 may be engaged to assign, un-assign and/or reassign all selected data status identifiers to a certain healthcare professional. In this manner, multiple data status identifiers 304 may be assigned, unassigned, and/or reassigned at the same time.

Figure 23D:
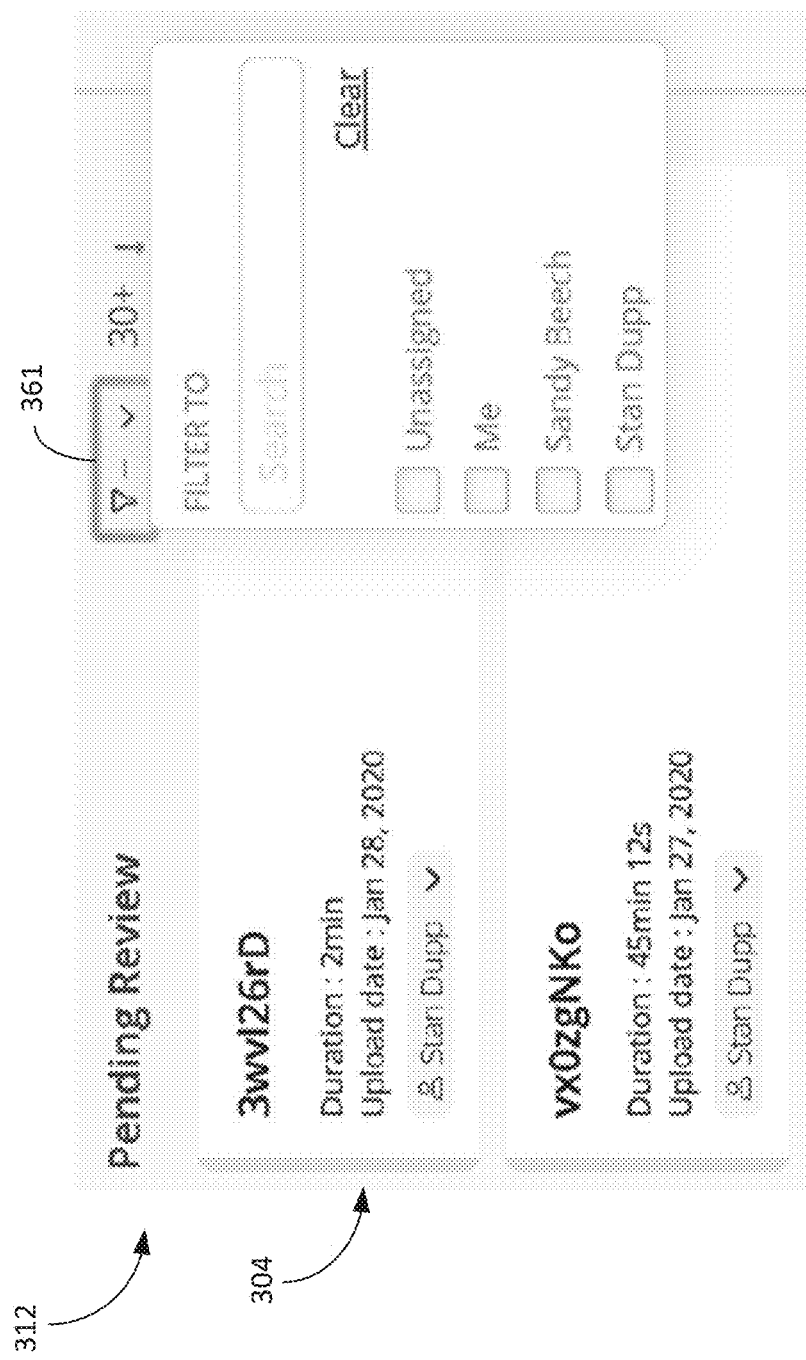

Referring now to FIG. 23D, pending review window 312 may include filter button 361. Filter button 361 may be used to filter one or more data status identifiers 304. As shown in FIG. 23D, filter button 361 may be engaged to filter data status identifiers 304 in pending review window 312 by the healthcare professional. For example, if the healthcare professional "Stan Dupp" is selected, only data status identifiers 304 assigned to Stan Dupp will be shown in pending review window 312. It is understood that other filters may be selected (date, patient, quality review status, etc.).

Figure 24A:
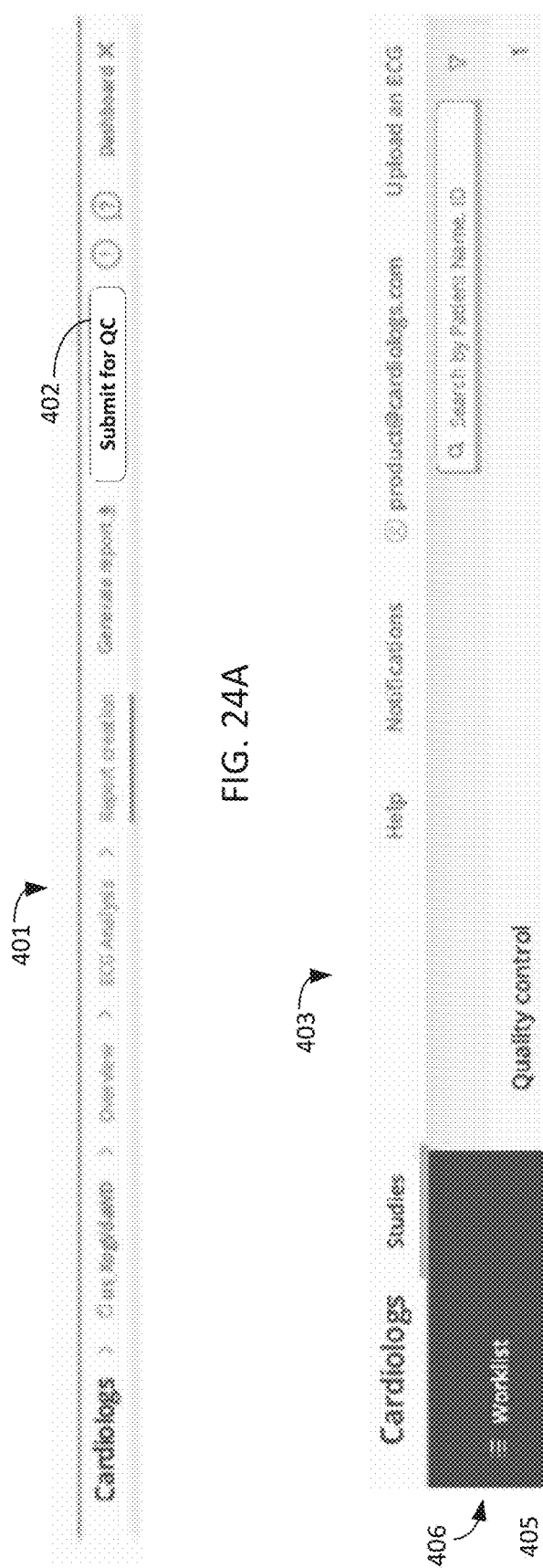
FIGS. 24A-24F illustrate user interfaces for quality control and quality review of ECG data and information based on ECG data.
Figure 24B:
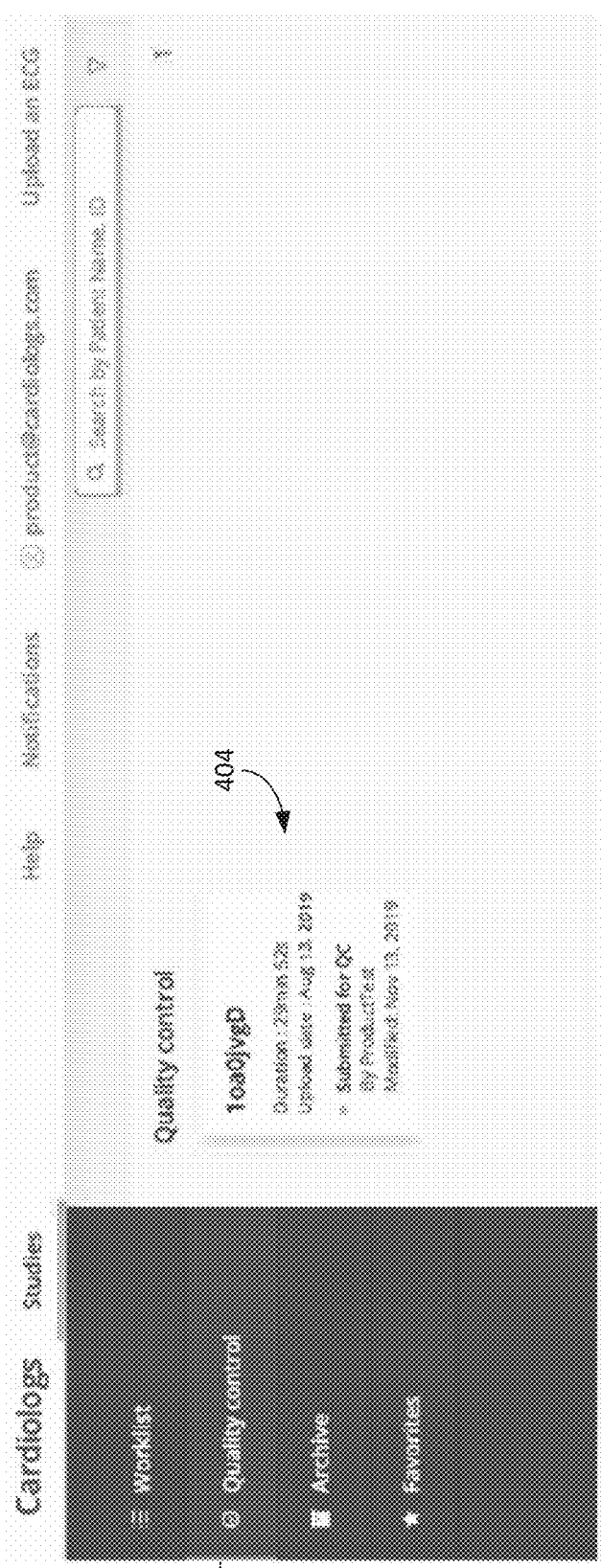

Referring now to FIGS. 24A-F, exemplary processes and user interfaces are illustrated for submitting ECG data and/or analyzed ECG data for quality review by one or more quality reviewers (e.g., technicians). As shown in FIGS. 24A-B, tool bar 401 may be incorporated into a user interface generated by ECG application 29 and/or ECG platform 37 and may be used to submit ECG data and/or analysis of ECG data for quality control (QC) (e.g., using quality control button 402). For example ECG platform 37 may generate group data, embedding data, classification data, delineation data, and/or analyzed ECG data and quality control button 402 may be engaged to submit the foregoing data for quality control.

Referring now to FIG. 24B, interface 403 is illustrated. Interface 403 displays a navigation column 406 which may include a worklist interface tab, quality control tab 405, an archive and a favorites tab, for example. Interface 403 may be used by a quality control reviewer, for example. When quality control tab 405 is engaged, one or more data status identifiers 404 may be displayed. Data status identifiers 404 may be the same as data status identifiers 304 and/or may include information about quality control (e.g., who submitted for quality control, date of submission, date of last modification, quality control status, etc.).

Figure 24C:
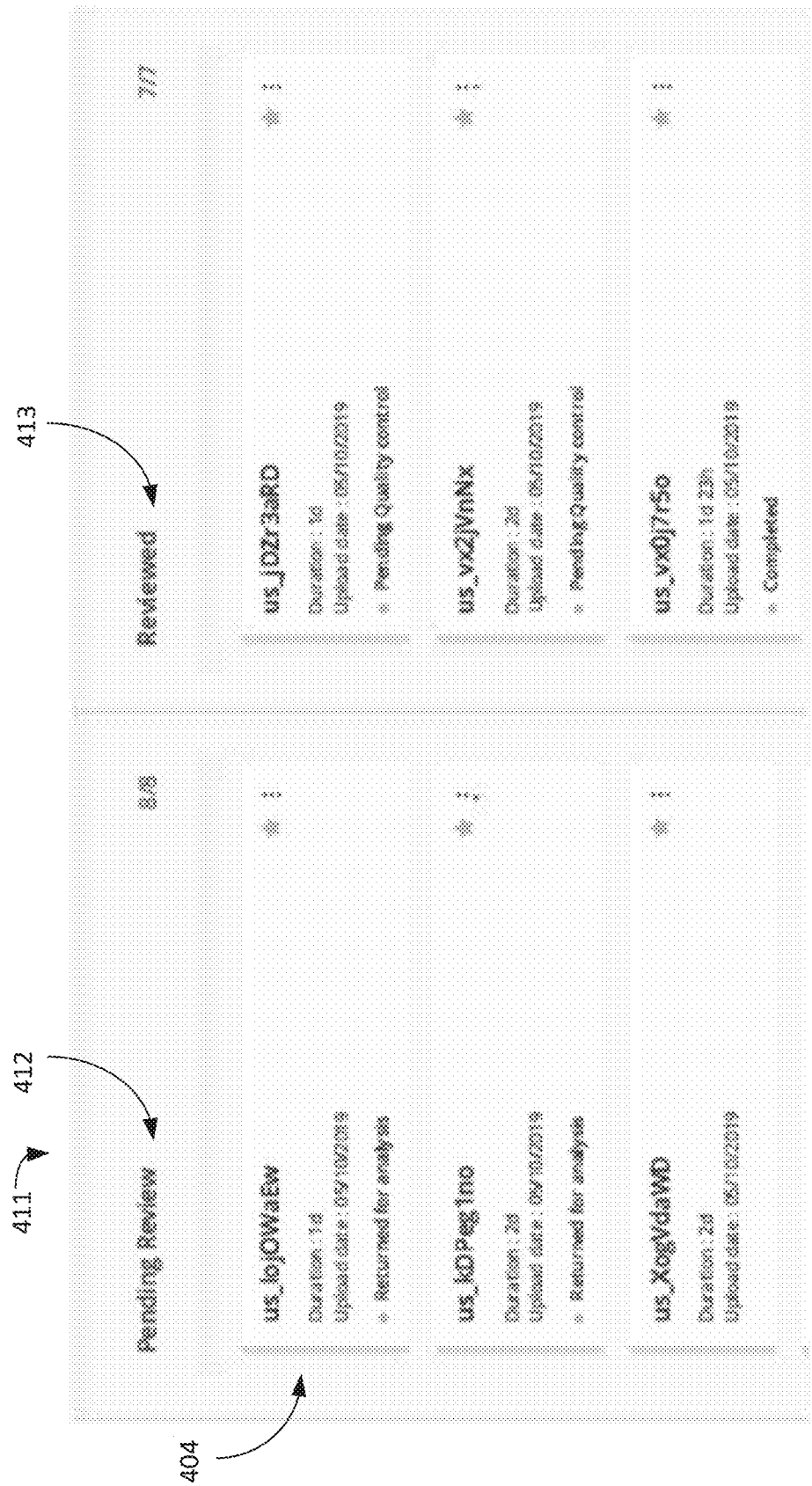

Referring now to FIG. 24C, ECG application 29 may cause system device 14 to display interface 411 for quality control review. Interface 411 may display pending window 412 and review window 413. Each of pending window 412 and review window 413 may include one or more data status identifiers 404. Pending window 412 may include one or more data status identifiers corresponding to uploaded data that is pending quality control review. Reviewed window 413 may include one or more data status identifiers 404 corresponding to uploaded data that has been reviewed. Quality control reviewers (e.g., an initial reviewer, a secondary reviewer, etc.) may use interface 411 to determine which data still needs to be reviewed and/or otherwise determine whether certain data should be reviewed or has been reviewed.

Figure 24D:
Figure 24E:
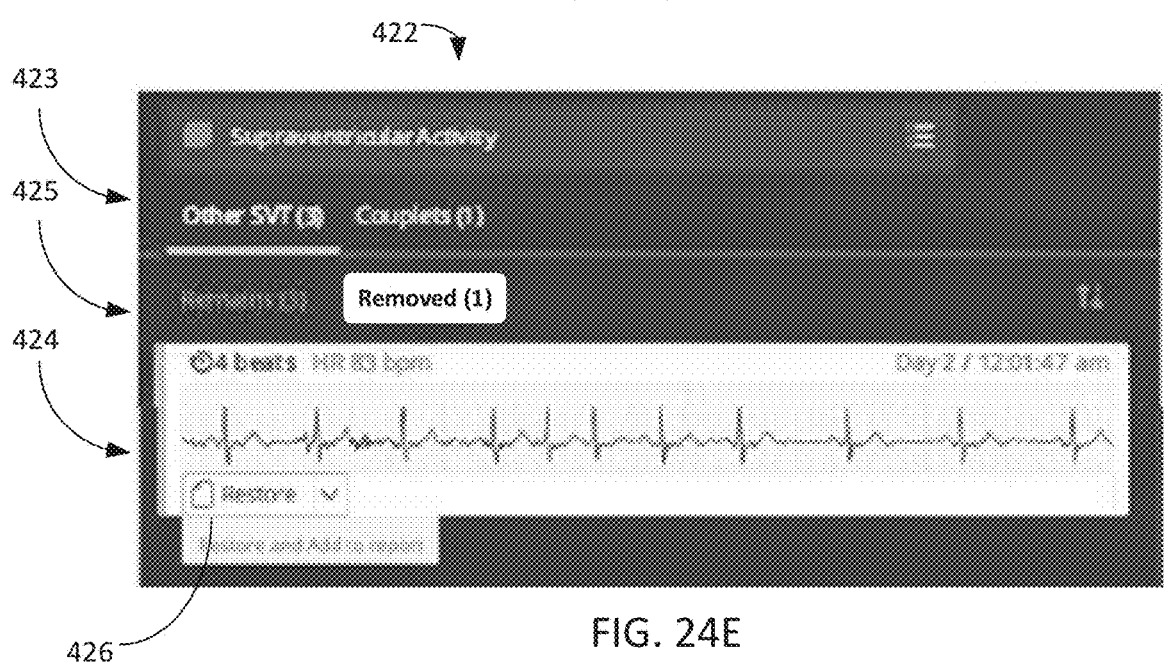

Data status identifier 404 may be selected for further quality control analysis of the data associated with the selected data status identifier 404. Upon selecting data status identifier 404, ECG application 29 may cause system device 14 to display FIGS. 24D-E. FIGS. 24D-E illustrate analysis interface 421 and analysis interface 422 which each illustrate ECG data strips 424 corresponding to data status identifier 404. ECG data strips 424 may be organized according to tabs 423 which may identify groups of ECG data strips (e.g., SVT, couplets, etc.). Analysis interface 421 and analysis interface 422 may be used to view ECG data strips that have been removed during quality control review as well as the ECG data strips that remain (i.e., have not been removed). Remove status 425 indicates whether the ECG data strips have been removed or if the ECG data strips are those that remain. For example, user interface 421 illustrates ECG data strips that remain and user interface 422 illustrates ECG data strips that have been removed. In this manner, the changes made during quality review may be archived and reviewed. Restore button 426 may be engaged to undo a removal of an ECG data strip such that it is re-categorized as a remaining ECG data strip.

Figure 24F:
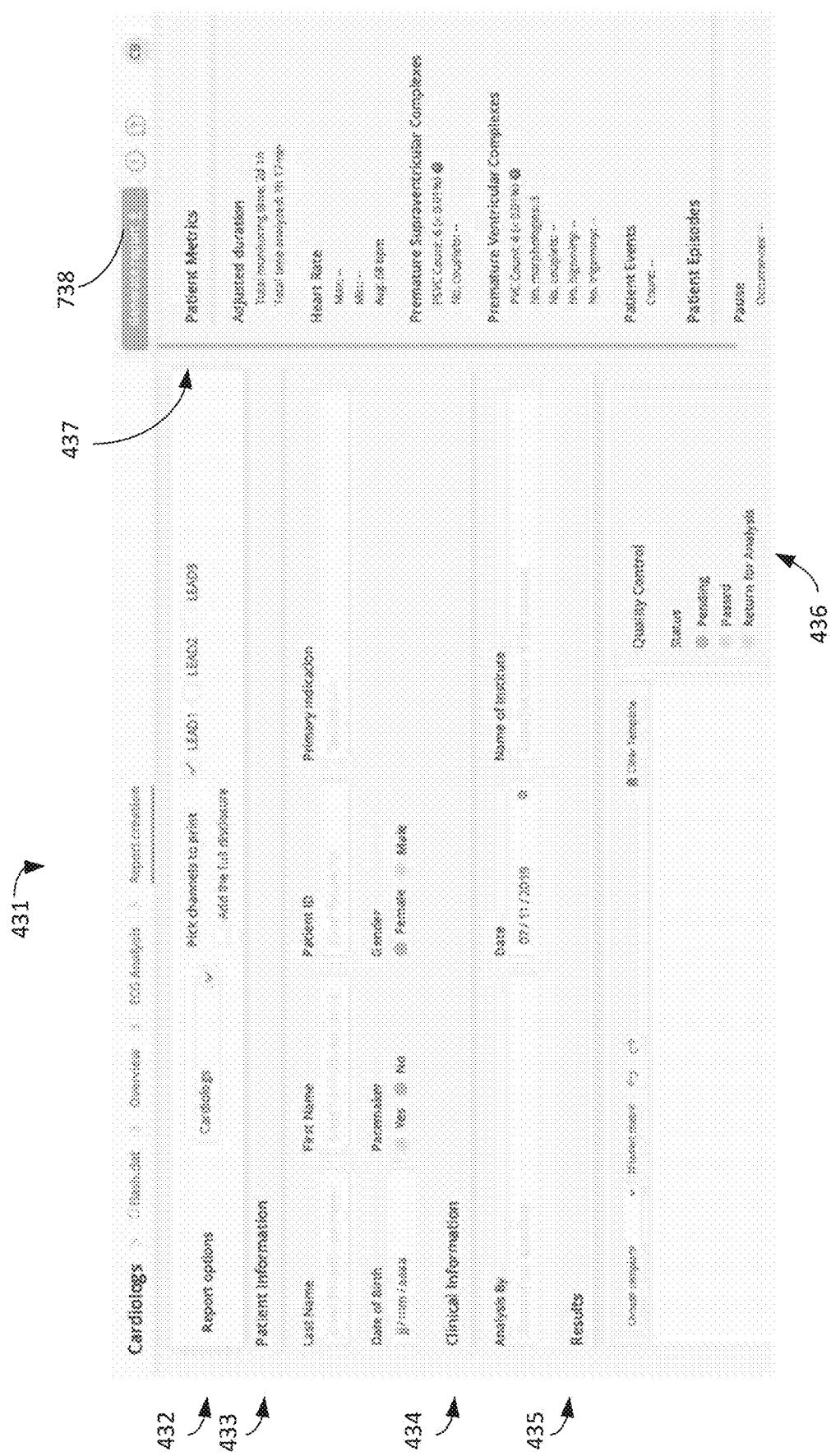

Referring now to FIG. 24F, interface 431 is illustrated and may be used to generate a report including quality control information (e.g., pending, passed, return for analysis). Interface 431 may include report options window 432, patient information window 433, clinical information window 434, results window 435, quality control window 436, patient metrics window 437, and/or generate report window 438. Report options window 432 may include several options for generating the report and may further permit selection of one or more leads for selecting ECG data to be included in the report. Patient information 433 may include identification and other information corresponding to the patient from which ECG data was generated (e.g., Name, patient identifier, primary indication, date of birth, presence of pacemaker, gender, etc.). Clinical information window 434 may include certain clinical information such as the name of the healthcare professional that conducted the analysis, the date, and/or the name of the institution. Results window 435 may be used to select results templates and/or or metrics. Quality control window 436 may be used to select the status of the quality control (e.g., pending, passed, return for analysis). Patient metrics window 437 may display certain patient metrics such as duration of monitoring and/or time analyzed, heart rate information, information about complexes (e.g., premature supraventricular complexes, premature ventricular complexes), patient events, patient episodes, and/or pause occurrences.

It should be understood that any of the operations described herein above may be implemented at least in part as computer-readable instructions stored on a computer-readable memory. Upon execution of the computer-readable instructions by a processor, the computer-readable instructions may cause a node to perform the operations. It will of course be understood that the embodiments described herein are illustrative, and components may be arranged, substituted, combined, and designed in a wide variety of different configurations, all of which are contemplated and fall within the scope of this disclosure.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims.

What is claimed is:

1. A computerized-system for analyzing electrocardiogram (ECG) data of a patient, the ECG data generated by one or more electrodes across a plurality of time points and comprising a plurality of beats, the computerized-system configured to:
    analyze the ECG data using a delineation algorithm to generate wave information corresponding to a likelihood of a presence of at least one wave at the plurality of time points;
    determine beat onset information and beat offset information for beats of the plurality of beats where at least one wave is determined to be present to generate a plurality of beat onsets and beat offsets;
    extract a plurality of beat portions of ECG data based on the plurality of beat onsets and beat offsets, each beat portion of the plurality of beat portions of ECG data corresponding to a beat of the plurality of beats;
    process the plurality of beat portions using an embedding algorithm to determine a plurality of embedding vectors representative of each beat of the plurality of beats;
    process the plurality of embedding vectors using a grouping algorithm to determine a plurality of group data corresponding to distances between embedding vectors indicative of similarities between two or more beats of the plurality of beats;
    determine that at least two beats of the plurality of beats should be grouped together based on group data of the plurality of group data, the at least two beats forming a cluster;
    transmit information indicative of the cluster to a computer for display on a graphic user interface;
    receive user input data from an input device regarding an inaccuracy corresponding to the ECG data, wherein the user input data corresponds to adding, deleting, or splitting one or more QRS clusters, PVC clusters, or PAC clusters;
    modify, based on the received user input data, the information indicative of the cluster displayed on the graphic user interface; and
    adjust, based on the received user input data, one or more of the delineation algorithm, embedding algorithm, or grouping algorithm.

2. The computerized-system of claim 1, wherein the computerized-system is further configured to:
    wherein the at least two beats of the plurality of beats are determined to be grouped together based on the grouping algorithm.

3. The computerized-system of claim 2, wherein a distance between embedding vectors corresponding to the at least two beats is indicative of a similarity of beat features of the at least two beats.

4. The computerized-system of claim 1, wherein the delineation algorithm utilizes a first neural network and an embedding algorithm associated with determining the plurality of embedding vectors utilizes a second neural network.

5. The computerized-system of claim 4, wherein the grouping algorithm utilizes a third neural network.

6. The computerized-system of claim 1, wherein the plurality of embedding vectors comprises a vector for each beat of the plurality of beats.

7. The computerized-system of claim 1, wherein determining that at least two beats of the plurality of beats should be grouped together further comprises determining that the group data satisfies a threshold value.

8. The computerized-system of claim 1, wherein the computerized-system is further configured to generate information to display at least one overlay comprising at least two beats of the plurality of beats overlaid over one another.

9. The computerized-system of claim 1, wherein the computerized-system is further configured to analyze the beats in the cluster using a classification algorithm to determine a likelihood of a presence of the one or more abnormalities, conditions, or descriptors associated with cardiac events for the patient.

10. The computerized-system of claim 1, wherein the computerized-system is further configured to analyze the wave information from the delineation algorithm using a classification algorithm to determine a likelihood of a presence of the one or more abnormalities, conditions, or descriptors associated with cardiac events for the patient.

11. The computerized-system of claim 10, wherein the wave information is inputted into the classification algorithm and separately used to determine that at least two beats of the plurality of beats should be grouped together.

12. The computerized-system of claim 1, wherein the computerized-system is further configured to, prior to analyzing the ECG data using the delineation algorithm, preprocess the ECG data to remove noise from the ECG data.

13. The computerized-system of claim 1, wherein the computerized-system is further configured to assign the ECG data and information based on the ECG data to a user account for review.

14. The computerized-system of claim 13, wherein the computerized-system is further configured to receive user input data regarding the ECG data and information based on the ECG data from the user account based on the review.

15. A method for analyzing electrocardiogram (ECG) data of a patient, the ECG data generated by one or more electrodes across a plurality of time points and comprising a plurality of beats, the method comprising:
    receiving ECG data comprising an identified cluster displayed on a graphic user interface, wherein the ECG data comprises the identified cluster is generated by:
        analyzing the ECG data using a delineation algorithm to generate wave information corresponding to a likelihood of a presence of at least one wave at the plurality of time points;
        determining beat onset information and beat offset information for beats of the plurality of beats where at least one wave is determined to be present to generate a plurality of beat onsets and beat offsets;
        extracting a plurality of beat portions of ECG data based on the plurality of beat onsets and beat offsets, each beat portion of the plurality of beat portions of ECG data corresponding to a beat of the plurality of beats;
        processing the plurality of beat portions using an embedding algorithm to determine a plurality of embedding vectors representative of each beat of the plurality of beats;
        processing the plurality of embedding vectors using a grouping algorithm to determine a plurality of group data corresponding to distances between embedding vectors indicative of similarities between beats of the plurality of beats;
        determining that at least two beats of the plurality of beats should be grouped together based on the plurality of group data, the at least two beats forming an identified cluster;
        transmitting the identified cluster to the graphic user interface;

providing, via the graphic user interface, user input data regarding an inaccuracy corresponding to the displayed ECG data, wherein the user input data corresponds to adding, deleting, or splitting one or more QRS clusters, PVC clusters, or PAC clusters; and receiving, via the graphic user interface, modified ECG data, wherein the modified ECG data is generated by modifying the displayed ECG data based on the provided user input data.

16. The method of claim 15, further comprising:

wherein the at least two beats of the plurality of beats are determined to be grouped together based on the grouping algorithm.

17. The method of claim 15, further comprising assigning the ECG data and information based on the ECG data to a user account for review of the ECG data.

18. The method of claim 15, further comprising submitting the ECG data and information based on the ECG data for quality review by one or more reviewers.

19. The method of claim 18, further comprising receiving quality control input generated by the one or more reviewers.

20. The method of claim 19, further comprising causing display of the quality control input for additional quality control review.

21. A system configured to improve automated patient diagnosis using electrocardiogram (ECG) data, comprising:

an ECG device obtaining ECG data of a patient, the ECG data generated by one or more electrodes across a plurality of time points and comprising a plurality of beats;

a system device in communication with the ECG device and configured to receive the ECG data, the system device comprising a processor with: (i) a trained delineation model configured to analyze the ECG data to generate wave information corresponding to a likelihood of a presence of at least one wave at the plurality of time points; (ii) a trained embedding model configured to determine a plurality of embedding vectors representative of each beat of the plurality of beats; and (iii) a trained grouping model configured to determine a plurality of group data corresponding to distances between embedding vectors indicative of similarities between beats of the plurality of beats, wherein the system device is configured to automatically generate a cluster comprising at least two beats of the plurality of beats grouped together via the steps of:

generating, using the trained delineation model, wave information corresponding to a likelihood of a presence of at least one wave at the plurality of time points;

determining beat onset information and beat offset information for beats of the plurality of beats where at least one wave is determined to be present to generate a plurality of beat onsets and beat offsets;

extracting a plurality of beat portions of ECG data based on the plurality of beat onsets and beat offsets, each beat portion of the plurality of beat portions of ECG data corresponding to a beat of the plurality of beats;

processing, using the trained embedding model, the plurality of beat portions to determine a plurality of embedding vectors representative of each beat of the plurality of beats;

processing, using the trained grouping model, the plurality of embedding vectors to determine a plurality of group data corresponding to distances between embedding vectors indicative of similarities between beats of the plurality of beats; and determining that at least two beats of the plurality of beats should be grouped together based on the plurality of group data, the at least two beats forming a cluster;

a user interface configured to display information to a user and to receive information from the user, wherein the system device transmits information indicative of the cluster to a computer for display on the graphic user interface, and wherein the user interface receives, in response to the displayed cluster, user input data regarding an inaccuracy corresponding to the ECG data, wherein the user input data corresponds to adding, deleting, or splitting one or more QRS clusters, PVC clusters, or PAC clusters;

wherein the system device is further configured to adjust, based on the received user input data, one or more of the trained delineation model, the trained embedding model, and the trained grouping model;

wherein the system device is further configured to: (i) automatically generate a new cluster comprising at least two beats of the plurality of beats grouped together using the adjusted one or more of the trained delineation model, the trained embedding model, and the trained grouping model, wherein generation of the new cluster is more accurate than generation of a previous cluster as a result of the adjusted one or more of the trained delineation model, the trained embedding model, and the trained grouping model; and (ii) cause the user interface to display the generated new cluster.

* * * * *